(12) United States Patent
Wrasidlo et al.

(10) Patent No.: US 11,708,338 B2
(45) Date of Patent: *Jul. 25, 2023

(54) SUBSTITUTED PHENYL SULFONYL PHENYL TRIAZOLE THIONES AND USES THEREOF

(71) Applicant: Neuropore Therapies, Inc., San Diego, CA (US)

(72) Inventors: Wolfgang J. Wrasidlo, La Jolla, CA (US); Emily M. Stocking, Encinitas, CA (US); Srinivasa Reddy Natala, San Diego, CA (US); Diana Luz Price, Escondido, CA (US)

(73) Assignee: Neuropore Therapies, Inc., San Diego, CA (US)

( * ) Notice: Subject to any disclaimer, the term of this patent is extended or adjusted under 35 U.S.C. 154(b) by 130 days.

This patent is subject to a terminal disclaimer.

(21) Appl. No.: 17/223,989

(22) Filed: Apr. 6, 2021

(65) Prior Publication Data
US 2021/0300881 A1 Sep. 30, 2021

Related U.S. Application Data

(60) Division of application No. 16/663,054, filed on Oct. 24, 2019, now Pat. No. 11,008,294, which is a continuation of application No. 16/366,793, filed on Mar. 27, 2019, now Pat. No. 10,501,423, which is a continuation of application No. PCT/US2018/058050, filed on Oct. 29, 2018.

(60) Provisional application No. 62/584,630, filed on Nov. 10, 2017, provisional application No. 62/579,070, filed on Oct. 30, 2017.

(51) Int. Cl.
| | | |
|---|---|---|
| C07D 249/12 | (2006.01) | |
| A61P 25/28 | (2006.01) | |
| A61K 9/10 | (2006.01) | |
| A61P 3/00 | (2006.01) | |
| C07D 243/10 | (2006.01) | |
| A61K 31/18 | (2006.01) | |

(52) U.S. Cl.
CPC ............. *C07D 249/12* (2013.01); *A61K 9/10* (2013.01); *A61K 31/18* (2013.01); *A61P 3/00* (2018.01); *A61P 25/28* (2018.01); *C07D 243/10* (2013.01)

(58) Field of Classification Search
CPC ................................ C07D 249/12; A61K 9/10
See application file for complete search history.

(56) References Cited

U.S. PATENT DOCUMENTS

| | | | |
|---|---|---|---|
| 4,163,015 A | 7/1979 | Johnson | |
| 4,279,637 A | 7/1981 | Wu | |
| 10,501,423 B2 | 12/2019 | Wrasidlo | |
| 11,008,294 B2 * | 5/2021 | Wrasidlo | ............. C07D 249/12 |
| 2002/0183306 A1 | 12/2002 | Howard, Jr. | |
| 2004/0110785 A1 | 6/2004 | Wang et al. | |
| 2004/0186288 A1 | 9/2004 | Kruger et al. | |
| 2004/0235877 A1 | 11/2004 | Ishizuka et al. | |
| 2005/0228031 A1 | 10/2005 | Bilodeau et al. | |
| 2006/0194802 A1 | 8/2006 | Abdellaoui et al. | |
| 2006/0217390 A1 | 9/2006 | Gunic et al. | |
| 2006/0281762 A1 | 12/2006 | Staehle et al. | |
| 2007/0093483 A1 | 4/2007 | Svensson et al. | |
| 2011/0166138 A1 | 7/2011 | Makriyannis et al. | |
| 2012/0077401 A1 | 3/2012 | Kotake et al. | |
| 2012/0196839 A1 | 8/2012 | Hutchinson et al. | |
| 2015/0197513 A1 | 7/2015 | Wrasidlo et al. | |

FOREIGN PATENT DOCUMENTS

| | | |
|---|---|---|
| CN | 102548984 A | 7/2012 |
| CN | 102574822 A | 7/2012 |
| DE | 3307506 | 9/1984 |
| WO | WO-2002/098851 | 12/2002 |
| WO | WO-2004/096781 | 11/2004 |
| WO | WO-2005/005394 | 1/2005 |
| WO | WO-2005/037829 | 4/2005 |
| WO | WO-2006/122011 | 11/2006 |
| WO | WO-2006/124875 | 11/2006 |
| WO | WO-2007/005785 | 1/2007 |
| WO | WO-2007/117381 | 10/2007 |
| WO | WO-2008/078100 | 7/2008 |
| WO | WO-2008/118718 | 10/2008 |
| WO | WO-2009/042435 | 4/2009 |
| WO | WO-2009/089454 | 7/2009 |
| WO | WO-2009/117444 | 9/2009 |
| WO | WO-2010/095031 | 8/2010 |
| WO | WO-2010/110433 | 9/2010 |
| WO | WO-2010/126895 | 11/2010 |
| WO | WO-2011/017350 | 2/2011 |
| WO | WO-2011/143419 | 11/2011 |
| WO | WO-2013/123061 | 8/2013 |
| WO | WO-2013/175215 | 11/2013 |

(Continued)

OTHER PUBLICATIONS

Ackerman et al., "Palladium- and nickel-catalyzed aminations of aryl imidazolylsulfonates and sulfamates," Org. Lett. (2011) 13(7):1784-1786.
Ahad et al., "Development of sulfonamide AKT PH domain inhibitors," Bioorg. Med. Chem. (2011) 19(6):2046-2054.
Amstutz, Journal of American Chemical Society (1947) 69:1922-1925.
Bagshawe, "Antibody-Directed Enzyme Prodrug Therapy: A Review," Drug Dev. Res. (1995) 34:220-230.
Bregman et al., "The discovery of aminopyrazines as novel, potent Na_v1.7 antagonists: Hit-to-lead identification and SAR," *Bioorg. Med. Chem. Lett.* 2012; 22(5): 2033-2042.

(Continued)

*Primary Examiner* — Golam M Shameem
(74) *Attorney, Agent, or Firm* — Morrison & Foerster LLP

(57) ABSTRACT

The present disclosure relates to substituted phenyl sulfonyl phenyl triazole thiones, pharmaceutical compositions containing them, and methods of using them.

24 Claims, 36 Drawing Sheets

(56) References Cited

FOREIGN PATENT DOCUMENTS

| WO | WO-2014/153270 | 9/2014 |
|----|----------------|--------|
| WO | WO-2019/089478 | 5/2019 |

OTHER PUBLICATIONS

Bertolini et al., "A new rational hypothesis for the pharmacophore of the active metabolite of leflunomide, a potent immunosuppressive drug," J. Med. Chem. (1997) 40(13):2011-2016.

Bhaskar et al. "The PI3K-Akt-mTOR pathway regulates Abeta oligomer induced neuronal cell cycle events," Molecular Neurodegeneration (2009) 4(14): 18 pages.

Bodor, "Novel Approaches to the Design of Safer Drugs: Soft Drugs and Site-Specific Chemical Delivery Systems," Adv. Drug Res. (1984) 13:255-331.

Boechat et al. "Simple Reduction of Heteroaromatic Esters to Alcohols Using a Sodium Borohydride-Methanol System," Syn. Comm. (2005) 35(24):3187-3190.

Brooks, D.J., "Positron Emission Tomography and Single-Photon Emission Computed Tomography in Central Nervous System Drug Development," *NeuroRx* 2005, 2(2), 226-236.

Chemical Abstracts Service, STN Registry, RN Nos. 73927-11-4, 112464-63-8, 112464-64-9, 749810-12-6, 859478-05-0, 859479-08-6, 918793-35-8, 923946-88-7, 1028302-85-3, 1144109-15-8, 1144109-16-9, 1144109-13-6, 1144109-17-0, 1144109-11-4, 1366234-25-4, 1375644-52-2, 1375644-55-5.

Cherra and Chu, "Autophagy in neuroprotection and neurodegeneration: A question of balance," Future Neurol. (2008) 3(3):309-323.

Codogno and Meijer, "Autophagy and signaling: their role in cell survival and cell death," Cell Death Differ. (2005) 12(S2):1509-1518.

Cretu et al., "Synthesis and characterization of some 1,2,4-triazole-3-thiones obtained from intramolecular cyclization of new 1-(4-(4-X-phe-nylsulfonyl)benzoyl)-4-(4-iodophenyl)-3-thiosemicarbazides", J. Serb. Chem. Soc. (2010) 75(11):1463-1471.

Database WPI Week 200316 Thomson Scientific, London, GB; AN 2003-167311. XP002794579.

De Kimpe and De Smaele, "Synthesis of aziridines and azetidines from N-(ω-haloalkyl) imines," Tetrahedron (1994) 35(43):8023-8026.

Deng et. al., "Discovery of 3,5-Diamino-1,2,4-triazole Ureas as Potent Anaplastic Lymphoma Kinase Inhibitors," ACS Med. Chem. Lett. (2011) 2:379-384.

Dong et al., "Theoretical studies on the interaction of biphenyl inhibitors with *Mycobacterium tuberculosis* protein tyrosine phosphatase MptpB," J. Mol. Model. (2012) 18:3847-3856.

Dorbec et al., "1-Aryltetralin privileged structure-based libraries: parallel synthesis of N-aryl and N-biaryl γ-lactam lignans," Tetrahedron 2006, 62(50), 11766-11781.

Extended European Search Report for EP 13828347.8; dated Mar. 3, 2016; 10 pages.

Ezabadi et al., "Sulfonamide-1,2,4-triazole Derivatives as Antifungal and Antibacterial Agents: Synthesis, Biological Evaluation, Lipophilicity, and Conformational Studies," Bioorg Med Chem. (2008) 16(3): 1150-1161.

Habibi et al., "Efficient synthesis of arylaminotetrazoles," Tetrahedron 2010, 66(21), 3866-3870.

Huang et al., "A series of alpha-heterocyclic carboxaldehyde thiosemicarbazones inhibit topoisomerase IIalpha catalytic activity," J. Med. Chem. (2010) 53(8):3048-3064.

International Search Report and Written Opinion for PCT/US18/58050, dated Jan. 15, 2019, 8 pages.

International Search Report and Written Opinion for PCT/US2013/054200, dated Apr. 29, 2014, 11 pages.

Jena et al., "Chimeric antigen receptor (CAR)-specific monoclonal antibody to detect CD19-specific T cells in clinical trials," PLoS One. (2013);8(3):e57838.

Letavic et al., "Benzylamine histamine $H_3$ antagonists and serotonin reuptake inhibitors," Bioorg. Med. Chem. Lett. (2007) 17(17):4799-4803.

Lucienne, "CD3-specific antibodies as promising tools to aim at immune tolerance in the clinic," Int Rev Immunol. (2006) 25(3-4): 215-33.

Maiti and Buchwald, "Cu-catalyzed arylation of phenols: synthesis of sterically hindered and heteroaryl diaryl ethers," J. Org. Chem. (2010) 75:1791-1794.

Maloney et al., "A practical, one-pot synthesis of sulfonylated pyridines," Org. Lett. (2011) 13(1):102-105.

Martinelli et al., "Palladium-catalyzed carbonylation reactions of aryl bromides at atmospheric pressure: a general system based on Xantphos," J. Org. Chem. (2008) 73(18):7102-7107.

Martinez-Vicente et al., "Cargo recognition failure is responsible for inefficient autophagy in Huntington's disease," Nat. Neurosci. (2010) 13(5):567-576.

Patani, "Bioisosterism: A Rational Approach in Drug Design", Chem. Rev. (1996) 96:3147-3176.

PubChem-CID-25147300, Create Date; Feb. 9, 2009 (Feb. 9, 2009), p. 3, Fig.

Ram et al., "Synthesis of Potential Antifilarial Agents 2 [1]. Methyl 2-Substituted Purine 8-Carbamates and Related Compounds," J. Het. Chem., 1989, 26 (4), 1053-1059.

Shaffer et al., "Foreign or Domestic CARs: Receptor Ligands as Antigen-Binding Domains," Med. Sci. (2014), 2(1), 23-36.

Shaban et al., "Oxidative cyclization of D-fructose thiosemicarbazones to 2-amino-5-(D-arabino-1,2,3,4-tetrahydroxybut-1-yl)-1,3,4-thiadiazoles through carbon-carbon bond cleavage of the sugar chain," Die Pharmazie (2003) 58(6):367-371.

Shan et al., "Prodrug strategies based on intramolecular cyclization reactions," J. Pharm. Sci. (1997) 86(7):765-767.

Stanovnik and Tisler, "The Structure of 2-Substituted Amino-1,3,4-thiadiazoles," J. Org. Chem., 1960, 25 (12), 2234-2236.

Trankle and Kopach, "Green Chemical Synthesis of 2-Benzenesulfonyl-pyridine and Related Derivatives," Org. Process Res. Dev., 2007, 11 (5), 913-917.

Tsvelikhovsky and Buchwald, "Concise Palladium-Catalyzed Synthesis of Dibenzodiazepines and Structural Analogues," J. Am. Chem. Soc. (2011) 133(36):14228-14231.

Vamos et al., "Neuroprotective Effects of Probenecid in a Transgenic Animal Model of Huntington's Disease," J Neural Transm (Vienna) (2009) 116(9): 1079-1086.

Yang et al., "Discovery of orally active pyrazoloquinolines as potent PDE10 inhibitors for the management of schizophrenia," Bioorg. Med. Chem. Lett. (2012) 22(1):235-239.

Li et al. "Synthesis of substituted-phenyl-1, 2, 4-triazol-3-thione analogues with modified d-glucopyranosyl residues and their antiproliferative activities." European journal of medicinal chemistry 44.11 (2009): 4716-4720.

* cited by examiner

**p<0.01 vs. non-tg/vehicle control
p<0.05 ASYN tg/treatment group vs. vs. ASYN tg/vehicle control

*p<0.05 vs. non-tg/vehicle control
p<0.05 ASYN tg/treatment group vs. vs. ASYN tg/vehicle control

SUBSTITUTED PHENYL SULFONYL PHENYL TRIAZOLE THIONES AND USES THEREOF

CROSS-REFERENCE TO RELATED APPLICATIONS

This application is a divisional of U.S. application Ser. No. 16/663,054, filed Oct. 24, 2019, which is a continuation of U.S. application Ser. No. 16/366,793, filed Mar. 27, 2019, now U.S. Pat. No. 10,501,423, which is a continuation of International Application Number PCT/US2018/058050, filed Oct. 29, 2018, which claims priority to U.S. Provisional Application No. 62/579,070, filed Oct. 30, 2017, entitled "SUBSTITUTED PHENYL SULFONYL PHENYL TRIAZOLE THIONES AND USES THEREOF" and U.S. Provisional Application No. 62/584,630, filed Nov. 10, 2017, entitled "SUBSTITUTED PHENYL SULFONYL PHENYL TRIAZOLE THIONES AND USES THEREOF" the contents of which are hereby incorporated by reference in their entirety for all purposes.

TECHNICAL FIELD

The present disclosure relates to substituted phenyl sulfonyl phenyl triazole thiones, pharmaceutical compositions containing such compounds, and methods of using them. These methods include, but are not limited to, the prevention of the aggregation or accumulation of neurotoxic proteins, the enhanced clearance of these proteins, decreased neuroinflammation, neuroprotective actions, and treatment of conditions associated with the progressive accumulation of toxic protein species and/or neuroinflammation. These conditions include neurodegenerative diseases such as Parkinson's disease, Alzheimer's disease, Lewy body disease, Parkinson's disease with dementia, fronto-temporal dementia, Huntington's disease, amyotrophic lateral sclerosis, multiple system atrophy, and progressive supranuclear palsy. In some embodiments, the condition is cancer, infection, Crohn's disease, heart disease, aging, traumatic brain injury (TBI), or a disease or condition associated with neuroinflammation.

BACKGROUND

Neurodegenerative disorders of the aging population such as Parkinson's or Alzheimer's disease are estimated to affect over 30 million people worldwide and rank among the top causes of death in the elderly. (*Alzheimer Europe* (2010), *European Parkinson's Disease Association* (2011)) A common feature among these neurological disorders is the chronic aggregation or accumulation of neurotoxic proteins and accompanying neuroinflammation. Compounds that prevent the overall progressive build-up of these proteins and/or decrease neuroinflammation may provide useful therapeutic benefit for these disorders.

SUMMARY

In one aspect, the present disclosure provides a compound of Formula (I):

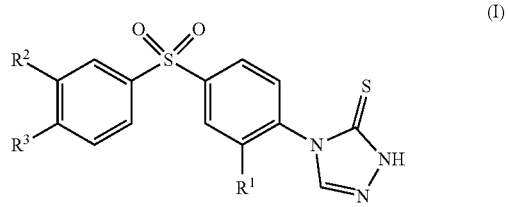

wherein
$R^1$, $R^2$, and $R^3$ are each independently hydrogen, hydroxy, halogen, optionally substituted $C_{1-4}$ alkyl, optionally substituted $C_{1-4}$ alkoxy, —CN, —C(O)$R^x$, —C(O)O$R^x$, —S(O)$_2R^x$, or —N$R^yR^z$;
$R^x$, $R^y$, and $R^z$ are each independently H or optionally substituted $C_{1-4}$alkyl, or $R^y$ and $R^z$ taken together with the nitrogen to which they are attached form an optionally substituted monocyclic heterocycloalkyl ring;
or a pharmaceutically acceptable salt thereof.

In some embodiments of Formula (I), $R^1$ is hydrogen, optionally substituted $C_{1-4}$ alkoxy, or —N$R^yR^z$. In some embodiments of Formula (I), $R^1$ is hydrogen. In some embodiments, $R^1$ is $C_{1-4}$ alkoxy, which is unsubstituted or substituted with one or more substituents selected from the group consisting of $C_1$-$C_6$ alkyl, $C_2$-$C_6$ alkenyl, $C_2$-$C_6$ alkynyl, hydroxyl, halogen, —N$R^fR^g$, cyano, nitro, $C_{1-4}$ alkoxy, $C_{1-4}$ haloalkoxy, —C(O)$R^4$, —OC(O)$R^4$, —C(O)O$R^4$, —C(O)N$R^fR^g$, and —OC(O)N$R^fR^g$, wherein $R^4$ is H or $C_{1-4}$alkyl and $R^f$ and $R^g$ are each independently H, $C_{1-4}$alkyl, —C(O)$C_{1-4}$alkyl, —C(O)O$C_{1-4}$alkyl, or —S(O)$_2C_{1-4}$alkyl. In some embodiments, $R^1$ is —(OCH$_2$CH$_2$)$_p$—O—CH$_2$CH$_3$ or —(OCH$_2$CH$_2$)$_p$—O—CH$_3$, wherein p is 0-10. In certain embodiments, $R^1$ is —OCH$_2$CH$_2$—O—CH$_2$CH$_3$ or —OCH$_2$CH$_2$OCH$_3$. In some embodiments, $R^1$ is —N$R^yR^z$, wherein $R^y$ and $R^z$ are each independently H or $C_{1-4}$alkyl, wherein the $C_{1-4}$alkyl is unsubstituted or substituted with one or more substituents selected from the group consisting of $C_1$-$C_6$ alkyl, $C_2$-$C_6$ alkenyl, $C_2$-$C_6$ alkynyl, hydroxyl, halogen, —N$R^fR^g$, cyano, nitro, $C_{1-4}$ alkoxy, $C_{1-4}$ haloalkoxy, —C(O)$R^4$, —OC(O)$R^4$, —C(O)O$R^4$, —C(O)N$R^fR^g$, and —OC(O)N$R^fR^g$, wherein $R^4$ is H or $C_{1-4}$alkyl and $R^f$ and $R^g$ are each independently H, $C_{1-4}$alkyl, —C(O)$C_{1-4}$alkyl, —C(O)O$C_{1-4}$alkyl, or —S(O)$_2C_{1-4}$alkyl. In some embodiments, $R^1$ is —NHCH$_2$CH$_2$OH or —N(CH$_2$CH$_3$)$_2$. In some embodiments, $R^1$ is —N$R^yR^z$, and $R^y$ and $R^z$ taken together with the nitrogen to which they are attached form an optionally substituted monocyclic heterocycloalkyl ring. In some embodiments, $R^1$ is —N$R^yR^z$, and $R^y$ and $R^z$ taken together with the nitrogen to which they are attached form a monocyclic heterocycloalkyl ring selected from morpholinyl, piperazinyl, piperidinyl, and pyrrolidinyl, wherein the morpholinyl, piperazinyl, piperidinyl, and pyrrolidinyl are each unsubstituted or substituted with one or more substituents selected from the group consisting of $C_1$-$C_6$ alkyl, $C_2$-$C_6$ alkenyl, $C_2$-$C_6$ alkynyl, hydroxyl, halogen, —N$R^fR^g$, cyano, nitro, $C_{1-4}$ alkoxy, $C_{1-4}$ haloalkoxy, —C(O)$R^4$, —C(O)O$R^4$, —C(O)N$R^fR^g$, and —OC(O)N$R^fR^g$, wherein $R^4$ is H or $C_{1-4}$alkyl and $R^f$ and $R^g$ are each independently H, $C_{1-4}$alkyl, —C(O)$C_{1-4}$alkyl, —C(O)O$C_{1-}$ 4alkyl, or —S(O)$_2$C$_{1-4}$alkyl. In certain embodiments, R$^1$ is morpholinyl, 4-methyl-piperazin-1-yl, piperidinyl, or pyrrolidinyl.

In some embodiments of Formula (I), R$^2$ is hydrogen, C$_{1-4}$ alkyl, or substituted C$_{1-4}$ alkyl. In some embodiments, R$^2$ is C$_{1-4}$ alkyl substituted with halogen. In some embodiments, R$^2$ is CF$_3$. In some embodiments, R$^2$ is methyl. In some embodiments, R$^2$ is optionally substituted C$_{1-4}$ alkoxy, —CN, or —NR$^y$R$^z$. In some embodiments, R$^2$ is —NR$^y$R$^z$, wherein R$^y$ and R$^z$ are each independently H or C$_{1-4}$alkyl, wherein the C$_{1-4}$alkyl is unsubstituted or substituted with one or more substituents selected from the group consisting of C$_1$-C$_6$ alkyl, C$_2$-C$_6$ alkenyl, C$_2$-C$_6$ alkynyl, hydroxyl, halogen, —NR$^f$R$^g$, cyano, nitro, C$_{1-4}$ alkoxy, C$_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or C$_{1-4}$alkyl and R$^f$ and R$^g$ are each independently H, C$_{1-4}$alkyl, —C(O)C$_{1-4}$alkyl, —C(O)OC$_{1-4}$alkyl, or —S(O)$_2$C$_{1-4}$alkyl. In certain embodiments, R$^2$ is —N(CH$_3$)$_2$. In some embodiments, R$^2$ is —NR$^y$R$^z$, and R$^y$ and R$^z$ taken together with the nitrogen to which they are attached form an optionally substituted monocyclic heterocycloalkyl ring. In some embodiments, R$^2$ is —NR$^y$R$^z$, and R$^y$ and R$^z$ taken together with the nitrogen to which they are attached form a monocyclic heterocycloalkyl ring selected from morpholinyl, piperazinyl, piperidinyl, and pyrrolidinyl, wherein the morpholinyl, piperazinyl, piperidinyl, and pyrrolidinyl are each unsubstituted or substituted with one or more substituents selected from the group consisting of C$_1$-C$_6$ alkyl, C$_2$-C$_6$ alkenyl, C$_2$-C$_6$ alkynyl, hydroxyl, halogen, —NR$^f$R$^g$, cyano, nitro, C$_{1-4}$ alkoxy, C$_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or C$_{1-4}$alkyl and R$^f$ and R$^g$ are each independently H, C$_{1-4}$alkyl, —C(O)$_{1-4}$ alkyl, —C(O)OC$_{1-4}$alkyl, or —S(O)$_2$C$_{1-4}$alkyl. In certain embodiments, R$^2$ is morpholinyl. In some embodiments, R$^2$ is —CN. In some embodiments, R$^2$ is C$_{1-4}$ alkoxy, unsubstituted or substituted with one or more substituents selected from the group consisting of C$_1$-C$_6$ alkyl, C$_2$-C$_6$ alkenyl, C$_2$-C$_6$ alkynyl, hydroxyl, halogen, —NR$^f$R$^g$, cyano, nitro, C$_{1-4}$ alkoxy, C$_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or C$_{1-4}$alkyl and R$^f$ and R$^g$ are each independently H, C$_{1-4}$alkyl, —C(O)C$_{1-4}$alkyl, —C(O)OC$_{1-4}$alkyl, or —S(O)$_2$C$_{1-4}$alkyl. In some embodiments, R$^2$ is —(OCH$_2$CH$_2$)$_p$—O—CH$_2$CH$_3$ or —(OCH$_2$CH$_2$)$_p$—O—CH$_3$, wherein p is 0-10. In certain embodiments, R$^2$ is methoxy, —OCH$_2$CH$_2$—O—CH$_2$CH$_3$, or —OCH$_2$CH$_2$OCH$_3$.

In some embodiments of Formula (I), R$^3$ is halogen. In some embodiments, R$^3$ is chloro. In some embodiments, R$^3$ is hydrogen. In some embodiments, R$^3$ is C$_{1-4}$ alkyl or substituted C$_{1-4}$ alkyl. In some embodiments, R$^3$ is methyl. In some embodiments, R$^3$ is C$_{1-4}$ alkyl substituted with one or more halogen. In some embodiments, R$^3$ is CF$_3$. In some embodiments, R$^3$ is —CN. In some embodiments, R$^3$ is —NR$^y$R$^z$, wherein R$^y$ and R$^z$ are each independently H or C$_{1-4}$alkyl, wherein the C$_{1-4}$alkyl is unsubstituted or substituted with one or more substituents selected from the group consisting of C$_1$-C$_6$ alkyl, C$_2$-C$_6$ alkenyl, C$_2$-C$_6$ alkynyl, hydroxyl, halogen, —NR$^f$R$^g$, cyano, nitro, C$_{1-4}$ alkoxy, C$_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or C$_{1-4}$alkyl and R$^f$ and R$^g$ are each independently H, C$_{1-4}$alkyl, —C(O)C$_{1-4}$alkyl, —C(O)OC$_{1-4}$alkyl, or —S(O)$_2$C$_{1-4}$alkyl. In some embodiments, R$^3$ is —NR$^y$R$^z$, and R$^y$ and R$^z$ taken together with the nitrogen to which they are attached form an optionally substituted monocyclic heterocycloalkyl ring. In some embodiments, R$^3$ is —NR$^y$R$^z$, and R$^y$ and R$^z$ taken together with the nitrogen to which they are attached form a monocyclic heterocycloalkyl ring selected from morpholinyl, piperazinyl, piperidinyl, and pyrrolidinyl, wherein the morpholinyl, piperazinyl, piperidinyl, and pyrrolidinyl are each unsubstituted or substituted with one or more substituents selected from the group consisting of C$_1$-C$_6$ alkyl, C$_2$-C$_6$ alkenyl, C$_2$-C$_6$ alkynyl, hydroxyl, halogen, —NR$^f$R$^g$, cyano, nitro, C$_{1-4}$ alkoxy, C$_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or C$_{1-4}$alkyl and R$^f$ and R$^g$ are each independently H, C$_{1-4}$alkyl, —C(O)C$_{1-4}$alkyl, —C(O)OC$_{1-4}$alkyl, or —S(O)$_2$C$_{1-4}$alkyl. In certain embodiments, R$^3$ is morpholinyl. In some embodiments, R$^3$ is C$_{1-4}$ alkoxy, unsubstituted or substituted with one or more substituents selected from the group consisting of C$_1$-C$_6$ alkyl, C$_2$-C$_6$ alkenyl, C$_2$-C$_6$ alkynyl, hydroxyl, halogen, —NR$^f$R$^g$, cyano, nitro, C$_{1-4}$ alkoxy, C$_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or C$_{1-4}$alkyl and R$^f$ and R$^g$ are each independently H, C$_{1-4}$alkyl, —C(O)C$_{1-4}$alkyl, —C(O)OC$_{1-4}$alkyl, or —S(O)$_2$C$_{1-4}$alkyl. In some embodiments, R$^3$ is —(OCH$_2$CH$_2$)$_p$—O—CH$_2$CH$_3$ or —(OCH$_2$CH$_2$)$_p$—O—CH$_3$, wherein p is 0-10.

In some embodiments, the compound of Formula (I) is a compound of Table 1, or a pharmaceutically acceptable salt thereof.

In some embodiments, the compound of Formula (I) is

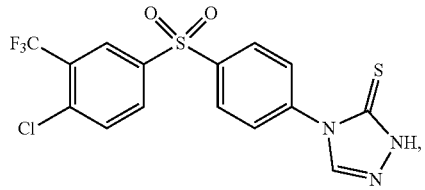 [SMILES: O=S(=O)(c1ccc(-n2cn[nH]c2=S)cc1)c1ccc(Cl)c(C(F)(F)F)c1]

or a pharmaceutically acceptable salt thereof. In some embodiments, the compound of Formula (I) is

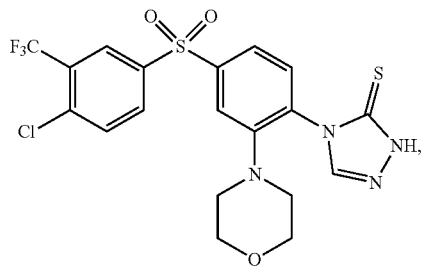 [SMILES: O=S(=O)(c1ccc(-n2cn[nH]c2=S)c(N2CCOCC2)c1)c1ccc(Cl)c(C(F)(F)F)c1]

or a pharmaceutically acceptable salt thereof.

In a further aspect, the present disclosure provides a pharmaceutical composition comprising (a) at least one compound of Formula (I) or a pharmaceutically acceptable salt thereof, and (b) a pharmaceutically acceptable excipient. In some embodiments, the pharmaceutically acceptable excipient is a polymeric agent. In some embodiments, the pharmaceutically acceptable excipient is selected from the group consisting of carboxymethyl cellulose (CMC), hydroxypropyl cellulose (HPC), hydroxyethyl cellulose (HEC), hydroxypropylmethyl cellulose (HPMC), gelatin, gelatin hydrolysate, sucrose, dextrose, polyvinylpyrrolidone (PVP), polyethyleneglycol (PEG), vinyl pyrrolidone copolymers, pregelatinized starch, sorbitol, and glucose; and polyacrylates. In some embodiments, the pharmaceutically acceptable excipient is selected from the group consisting of hydroxypropylmethyl cellulose (HPMC), polyvinylpyrrolidone (PVP), and Kollidon. In some embodiments, the pharmaceutical composition is in the form of a spray dry dispersion (SDD).

The present disclosure also provides a compound of Formula I or a pharmaceutically acceptable salt thereof for use as a medicament.

In some aspects, the compound of Formula (I), or a pharmaceutically acceptable salt thereof, or a pharmaceutical composition containing the compound of Formula (I), is used in treating a condition associated with neurodegeneration or aggregation/accumulation of proteins such as alpha synuclein, a-beta, tau, Huntingtin, or TAR DNA binding protein 43 (TDP43). In some embodiments, the condition is a neurodegenerative disease or condition. In some embodiments, the condition is Alzheimer's Disease, Parkinson's Disease, fronto-temporal dementia, dementia with Lewy Bodies, PD dementia, multiple system atrophy, Huntington's disease, Amyotrophic lateral sclerosis, progressive supranuclear palsy, cancer, infection, Crohn's disease, heart disease, aging, or traumatic brain injury (TBI). In another aspect, the compound of Formula (I), or a pharmaceutically acceptable salt thereof, or a pharmaceutical composition containing the compound of Formula (I), has neuroprotective actions.

In some aspects, provided are methods of treating a condition associated with neurodegeneration or aggregation/accumulation of proteins such as alpha synuclein, a-beta, tau, Huntingtin, or TDP43, comprising administering to a subject in need of such treatment an effective amount of at least one compound of Formula (I) or a pharmaceutically acceptable salt thereof, or a pharmaceutical composition comprising a compound of Formula (I). In some embodiments, the condition is a neurodegenerative disease or condition. In some embodiments, the condition is Alzheimer's Disease, Parkinson's Disease, fronto-temporal dementia, dementia with Lewy Bodies, PD dementia, multiple system atrophy, Huntington's disease, Amyotrophic lateral sclerosis, progressive supranuclear palsy, cancer, infection, Crohn's disease, heart disease, aging, or traumatic brain injury (TBI).

In some aspects, the present disclosure provides use of at least one compound of Formula (I), or a pharmaceutically acceptable salt thereof, in the manufacture of a medicament for the treatment of a condition associated with neurodegeneration or accumulation of proteins. In some embodiments, the condition is Alzheimer's Disease, Parkinson's Disease, fronto-temporal dementia, dementia with Lewy Bodies, PD dementia, multiple system atrophy, Huntington's disease, Amyotrophic lateral sclerosis, progressive supranuclear palsy, cancer, infection, Crohn's disease, heart disease, aging, or traumatic brain injury (TBI).

In another aspect, the present disclosure provides a method of preventing aggregation or accumulation or enhancing clearance of protease-resistant protein, comprising contacting the protease-resistant protein with an effective amount of at least one compound of Formula (I), or a salt thereof, or a pharmaceutical composition provided herein, wherein the contacting is in vitro, ex vivo, or in vivo. In some embodiments, the protease-resistant protein is alpha synuclein, a-beta, tau, Huntingtin, or TDP43 proteins.

In yet another aspect, the compound of Formula (I), or a pharmaceutically acceptable salt thereof, or a pharmaceutical composition containing the compound of Formula (I), is used in decreasing neuroinflammation in a subject. In some embodiments, the compound of Formula (I), or a pharmaceutically acceptable salt thereof, or a pharmaceutical composition containing the compound of Formula (I), is used in treating a disease or condition associated with neuroinflammation. In some embodiments, the present disclosure provides a method of decreasing neuroinflammation in a subject, comprising administering to the subject an effective amount of at least one compound of Formula (I), or a pharmaceutically acceptable salt thereof, or a pharmaceutical composition provided herein. In some embodiments, the present disclosure provides a method of treating a disease or condition associated with neuroinflammation, comprising administering to the subject an effective amount of at least one compound of Formula (I), or a pharmaceutically acceptable salt thereof, or a pharmaceutical composition provided herein. In some embodiments, the present disclosure provides use of at least one compound of Formula (I), or a pharmaceutically acceptable salt thereof, in the manufacture of a medicament for decreasing neuroinflammation. In other embodiments, the present disclosure provides use of at least one compound of Formula (I), or a pharmaceutically acceptable salt thereof, in the manufacture of a medicament for the treatment of a disease or condition associated with neuroinflammation.

Additional embodiments, features, and advantages of the compounds, compositions, methods, and uses described herein will be apparent from the following detailed description.

BRIEF DESCRIPTION OF THE DRAWINGS

FIG. 3H and FIG. 3I show the TGA and DSC thermograms, respectively, for spray dry dispersion (SDD) #4.

DETAILED DESCRIPTION

Figure 1A:
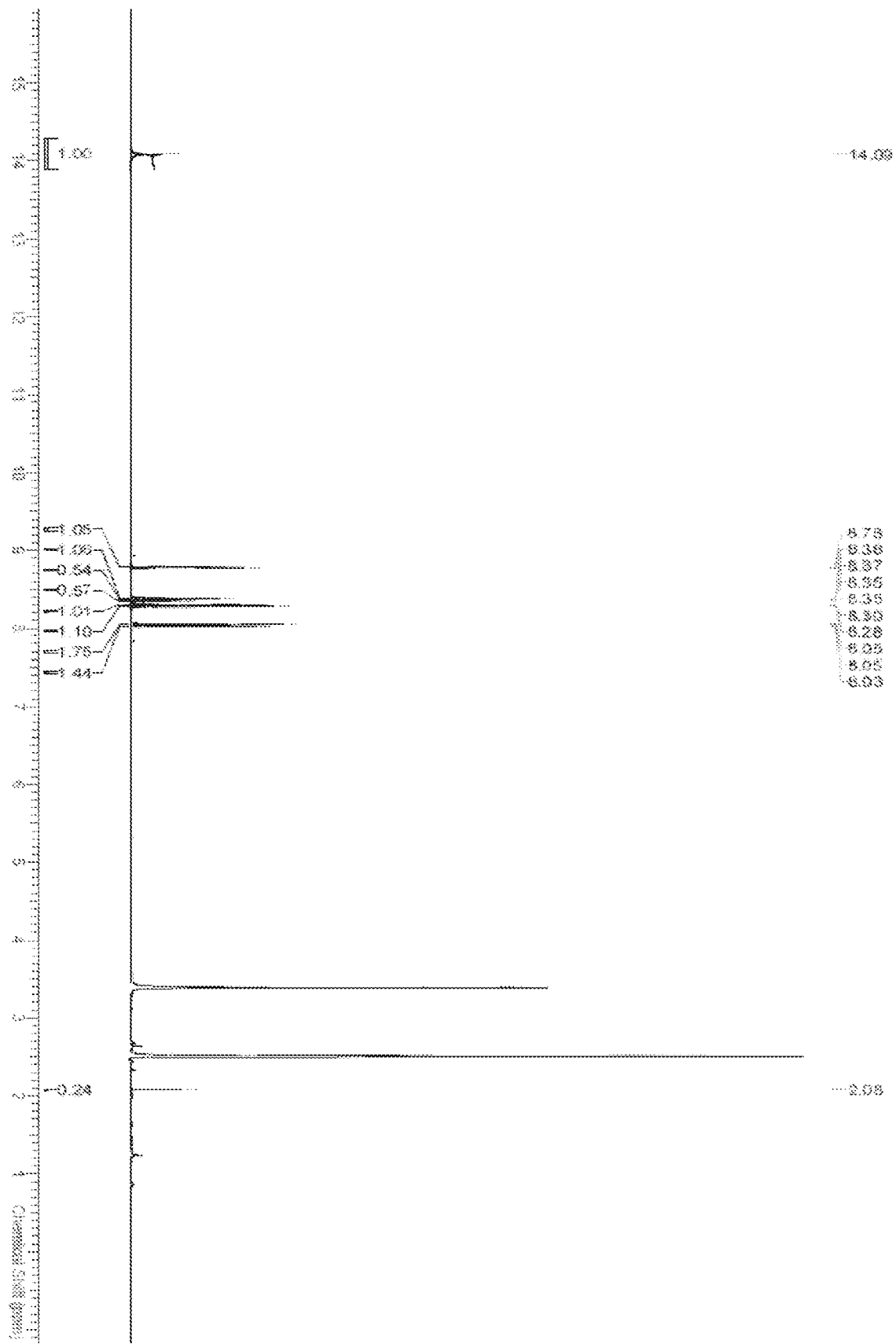
FIG. 1A shows a $^1$H NMR spectrum of Compound 1 in DMSO-d6 (400 MHz).

The present disclosure relates to substituted sulfonyl phenyl-2,4-dihydro-3H-1,2,4-triazole-3-thiones, pharmaceutical compositions containing them, and methods of using them, including methods for treating neurodegenerative diseases and other disorders where there is an associated accumulation of toxic protein aggregates.

Terms

It is to be understood that the compounds, compositions, methods, and uses described herein are not limited to particular embodiments described, as such may, of course, vary. It is also to be understood that the terminology used herein is for the purpose of describing particular embodiments only, and is not intended to be limiting, since the scope of the compounds, compositions, methods, and uses described herein will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

The following terms have the following meanings unless otherwise indicated. Any undefined terms have their art recognized meanings.

The term "alkyl" refers to a straight- or branched-chain alkyl (hydrocarbon) group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. In some instances, alkyl groups are $C_{1-4}$alkyl.

"Alkenyl" refers to an unsaturated branched or straight-chain hydrocarbon group having the indicated number of carbon atoms (e.g., 2 to 8, or 2 to 6 carbon atoms) and at least one site of olefinic unsaturation (having at least one carbon-carbon double bond). The alkenyl group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl).

"Alkynyl" refers to an unsaturated branched or straight-chain hydrocarbon group having the indicated number of carbon atoms (e.g., 2 to 8 or 2 to 6 carbon atoms) and at least one site of acetylenic unsaturation (having at least one carbon-carbon triple bond). Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Aryl" or "Ar" as used herein refers to an unsaturated aromatic carbocyclic group having a single ring (e.g., phenyl) or multiple condensed rings (e.g., naphthyl or anthryl), which condensed rings are carbocyclic and may or may not be aromatic, provided at least one ring in the multiple condensed ring structure is aromatic. Particular aryl groups are those having from 6 to 14 annular carbon atoms (a "$C_6$-$C_{14}$ aryl"). An aryl group having more than one ring where at least one ring is non-aromatic is connected to the parent structure at either an aromatic ring position or at a non-aromatic ring position. In one variation, an aryl group having more than one ring where at least one ring is non-aromatic is connected to the parent structure at an aromatic ring position.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

"Cycloalkyl" as used herein refers to and includes, unless otherwise stated, saturated or partially unsaturated nonaromatic cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 annular carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cyano" or "nitrile" refers to the group —CN.

"Halo" or "halogen" refers to fluoro, chloro, bromo, and iodo.

"Hydroxy" or "hydroxyl" refers to the group —OH.

"Heterocycloalkyl" or "heterocyclyl" refers to a saturated or partially unsaturated group having a single ring or multiple condensed rings, including fused, bridged, or spiro ring systems, and having from 3 to 20 ring atoms, including 1 to 10 hetero atoms. These ring atoms are selected from the group consisting of carbon, nitrogen, sulfur, and oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for N-oxide, —S(O)—, or —S(O)$_2$— moieties. Examples of heterocycloalkyls include, but are not limited to, azetidine, oxetane, tetrahydrofuran, pyrrolidine, piperazine, piperidine, morpholine, thiomorpholine, 1,1-dioxothiomorpholinyl, dihydroindole, indazole, quinolizine, imidazolidine, imidazoline, indoline, 1,2,3,4-tetrahydroisoquinoline, thiazolidine, and the like. In some instances, heterocycloalkyl groups are 4-, 5-, or 6-membered rings. In some instances, the heterocycloalkyl comprises a fused phenyl ring.

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl), which condensed rings may be carbocyclic or may contain one or more annular heteroatom and which may or may not be aromatic, provided at least one ring in the multiple condensed ring structure is both aromatic and contains at least one annular heteroatom, and provided that the point of attachment is through the aromatic ring containing at least one annular heteroatom. A heteroaryl group may be connected to the parent structure at a ring carbon atom or a ring heteroatom. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur.

"Oxo" refers to the group (=O) or (O).

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —S(O)$R^{70}$, —S(O)$_2R^{70}$, —S(O)$_2O^-M^+$, —S(O)$_2OR^{70}$, —OS(O)$_2R^{70}$, —OS(O)$_2O^-$ $M^+$, —OS(O)$_2OR^{70}$, —P(O)($O^-$)$_2$($M^+$)$_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —C(O)$O^-$ $M^+$, —C(O)$OR^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —OC(O)$O^-$ $M^+$, —OC(O)$OR^{70}$, —OC(S)$OR^{70}$, —$NR^{70}$C(O)$R^{70}$, —$NR^{70}$C(S)$R^{70}$, —$NR^{70}$C(O)$O^-M^+$, —$NR^{70}$C(O)$OR^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$ is selected from the group consisting of optionally substituted alkyl, cycloalkyl, heterocycloalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 3-, 4-, 5-, 6-, or 7-membered heterocycloalkyl which may optionally include from 1 to 4 of the same or different additional heteroatoms selected from the group consisting of O, N and S, of which N may have —H, $C_1$-$C_4$ alkyl, —C(O)$C_{1-4}$alkyl, —C(O)O$C_{1-4}$alkyl, or —S(O)$_2C_{1-4}$alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as [$Ca^{2+}$]$_{0.5}$, [$Mg^{2+}$]$_{0.5}$, or [$Ba^{2+}$]$_{0.5}$ ("subscript 0.5 means that one of the counter ions for such divalent alkali earth ions can be an ionized form of a compound provided herein and the other a typical counter ion such as chloride, or two ionized compounds disclosed herein can serve as counter ions for such divalent alkali earth ions, or a doubly ionized compound provided herein can serve as the counter ion for such divalent alkali earth ions). As specific examples, —$NR^{80}R^{80}$ is meant to include —$NH_2$, —NH-alkyl, N-pyrrolidinyl, N-piperazinyl, 4-N-methyl-piperazin-1-yl and N-morpholinyl.

In addition to the substituent groups disclosed with respect to the individual terms herein, substituent groups for hydrogens on nitrogen atoms in "substituted" heterocycloalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —S(O)$R^{70}$, —S(O)$_2R^{70}$, —S(O)$_2O^-M^+$, —S(O)$_2OR^{70}$, —OS(O)$_2R^{70}$, —OS(O)$_2O^-$ $M^+$, —OS(O)$_2OR^{70}$, —P(O)($O^-$)$_2$($M^+$)$_2$, —P(O)($OR^{70}$)$O^-$ $M^+$, —P(O)($OR^{70}$)($OR^{70}$), —C(O)$R^{70}$, —C(S)$R^{70}$, —C($NR^{70}$)$R^{70}$, —C(O)$OR^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —OC(O)$OR^{70}$, —OC(S)$OR^{70}$, —$NR^{70}$C(O)$R^{70}$, —$NR^{70}$C(S)$R^{70}$, —$NR^{70}$C(O)$OR^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined. Where a heterocycloalkyl group is "substituted," unless otherwise constrained by the definition for the heterocycloalkyl substituent, such groups can be substituted with 1 to 5, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, azido, cyano, halogen, hydroxyl, oxo, thioketo, carboxyl, carboxyl ester, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, sulfonylamino, —S(O)-alkyl, —S(O)-substituted alkyl, —S(O)-aryl, —S(O)-heteroaryl, —S(O)-heterocyclyl, —S(O)$_2$-alkyl, —S(O)$_2$-substituted alkyl, —S(O)$_2$-aryl, —S(O)$_2$-heteroaryl, and —S(O)$_2$-heterocyclyl.

It is understood that when a group is indicated as "substituted", it may be substituted with 1 or more substituents, and that the substituents may be present at any or all of the valency-allowed position(s) on the system. In some embodiments, a group that is substituted has 1, 2, 3, or 4 substituents, 1, 2, or 3 substituents, 1 or 2 substituents, or 1 substituent.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents. In one embodiment, the "optionally substituted" group is not substituted.

Unless indicated otherwise, the nomenclature of substituents that are not explicitly defined herein are arrived at by naming the terminal portion of the functionality followed by the adjacent functionality toward the point of attachment.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt"

refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers. Compounds that have asymmetric centers can exist as one or more enantiomeric forms, one or more diastereomeric forms, one or more atropisomeric forms, and mixtures thereof in any ratio.

Any formula given herein is intended to refer also to any one of hydrates, solvates, and amorphous and polymorphic forms of such compounds, and mixtures thereof, even if such forms are not listed explicitly.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into the compounds described herein include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labeled compounds are useful in metabolic studies (e.g., with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In some embodiments, $^{18}F$ or $^{11}C$ labeled compounds are used for PET or SPECT studies. PET and SPECT studies may be performed as described, for example, by Brooks, D. J., "Positron Emission Tomography and Single-Photon Emission Computed Tomography in Central Nervous System Drug Development," NeuroRx 2005, 2(2), 226-236, and references cited therein. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds and prodrugs thereof can generally be prepared by carrying out the procedures disclosed in the schemes or in the examples and preparations described below by substituting a readily available isotopically labeled reagent for a non-isotopically labeled reagent.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art. The methods and materials are now described; however, any methods and materials similar or equivalent to those described herein can also be used in the practice or testing of the compounds of compositions described herein. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, 4$^{th}$ edition, New York: Oxford University Press, 2002, pp. 360-361, 1084-1085; Smith and March, March's Advanced Organic Chemistry: Reactions, Mechanisms, and Structure, 5$^{th}$ edition, Wiley-Interscience, 2001.

The nomenclature used herein to name the subject compounds is illustrated in the Examples herein. This nomenclature has generally been derived using the commercially-available ChemBioDraw Ultra 13.0.2.3021 (CambridgeSoft, Cambridge, Mass.).

It is appreciated that certain features of the compounds, compositions, methods, and uses described herein, which are, for clarity, described in the context of separate embodiments, may also be provided in combination in a single embodiment. Conversely, various features of the compounds, compositions, methods, and uses described herein which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Compounds

Compounds and salts thereof (such as pharmaceutically acceptable salts) are detailed herein, including in the Summary and in the appended claims. Also provided are the use of all of the compounds described herein, including salts and solvates of the compounds described herein, as well as methods of making such compounds. Any compound described herein may also be referred to as a drug.

In one aspect, provided are compounds of Formula (I):

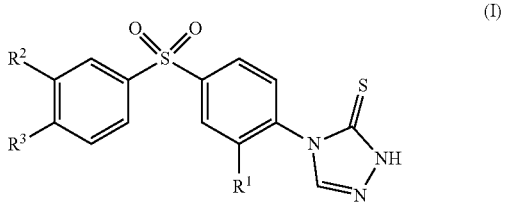

wherein $R^1$, $R^2$, and $R^3$ are each independently hydrogen, hydroxy, halogen, optionally substituted $C_{1-4}$ alkyl, optionally substituted $C_{1-4}$ alkoxy, —CN, —C(O)$R^x$, —C(O)O$R^x$, —S(O)$_2$$R^x$, or —N$R^y$$R^z$;

$R^x$, $R^y$, and $R^z$ are each independently H or optionally substituted $C_{1-4}$alkyl, or $R^y$ and $R^z$ taken together with the nitrogen to which they are attached form an optionally substituted monocyclic heterocycloalkyl ring;

or a pharmaceutically acceptable salt thereof.

In some embodiments, when a group is described as being optionally substituted, the indicated group is unsubstituted or substituted by one or more substituents selected from the group consisting of oxo, $C_1$-$C_6$ alkyl, $C_2$-$C_6$ alkenyl, $C_2$-$C_6$ alkynyl, halogen, —CN, —O$R^4$, —S$R^4$, —N$R^5$$R^6$, —NO$_2$, —C=NH(O$R^4$), —C(O)$R^4$, —OC(O)$R^4$, —C(O)O$R^4$, —C(O)N$R^5$$R^6$, —OC(O)N$R^5$$R^6$, —N$R^4$C(O)$R^5$, —N$R^4$C(O)O$R^5$, —N$R^4$C(O)N$R^5$$R^6$, —S(O)$R^4$, —S(O)$_2$$R^4$, —N$R^4$S(O)$R^5$, —C(O)N$R^4$S(O)$R^5$, —N$R^4$S(O)$_2$$R^5$, —C(O)N$R^4$S(O)$_2$$R^5$, —S(O)N$R^5$$R^6$, —S(O)$_2$N$R^5$$R^6$, —P(O)(O$R^5$)(O$R^6$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)O$R^4$, —($C_1$-$C_3$ alkylene)S$R^4$, —($C_1$-$C_3$ alkylene)N$R^5$$R^6$, —($C_1$-$C_3$ alkylene)CF$_3$, —($C_1$-$C_3$ alkylene)NO$_2$, —C=NH(O$R^4$), —($C_1$-$C_3$ alkylene)C(O)$R^4$, —($C_1$-$C_3$ alkylene)OC(O)$R^4$, —($C_1$-$C_3$ alkylene)C(O)O$R^4$, —($C_1$-$C_3$ alkylene)C(O)N$R^5$$R^6$, —($C_1$-$C_3$ alkylene)OC(O)N$R^5$$R^6$, —($C_1$-$C_3$ alkylene)N$R^4$C(O)$R^5$, —($C_1$-$C_3$ alkylene)N$R^4$C(O)O$R^5$, —($C_1$-$C_3$ alkylene)N$R^4$C(O)N$R^5$$R^6$, —($C_1$-$C_3$ alkylene)S(O)$R^4$, —($C_1$-$C_3$ alkylene)S(O)$_2$$R^4$, —($C_1$-$C_3$ alkylene)N$R^4$S(O)$R^5$, —C(O)($C_1$-$C_3$ alkylene)N$R^4$S(O)$R^5$, —($C_1$-$C_3$ alkylene)N$R^4$S(O)$_2$$R^5$, —($C_1$-$C_3$ alkylene)C(O)N$R^4$S(O)$_2$$R^5$, —($C_1$-$C_3$ alkylene)S(O)N$R^5$$R^6$, —($C_1$-$C_3$ alkylene)S(O)$_2$N$R^5$$R^6$, —($C_1$-$C_3$ alkylene)P(O)(O$R^5$)(O$R^6$), —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) and —($C_1$-$C_3$ alkylene)($C_6$-$C_{14}$ aryl), wherein the one or more substituents are each independently unsubstituted or substituted with one or more further substituents selected from the group consisting of halogen, oxo, —O$R^7$, —N$R^7$$R^8$, —C(O)$R^7$, —CN, —S(O)$R^7$, —S(O)$_2$$R^7$, —P(O)(O$R^7$)(O$R^8$), —($C_1$-$C_3$ alkylene)O$R^7$, —($C_1$-$C_3$ alkylene)N$R^7$$R^8$, —($C_1$-$C_3$ alkylene)C(O)$R^7$, —($C_1$-$C_3$ alkylene)S(O)$R^7$, —($C_1$-$C_3$ alkylene)S(O)$_2$$R^7$, —($C_1$-$C_3$ alkylene)P(O)(O$R^7$)(O$R^8$), $C_3$-$C_8$ cycloalkyl, $C_1$-$C_6$ alkyl, and $C_1$-$C_6$ alkyl substituted by oxo, —OH or halogen; wherein each $R^4$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6-membered heterocyclyl are independently unsubstituted or substituted by halogen, oxo, —CN, —O$R^9$, —N$R^9$$R^{10}$, —P(O)(O$R^9$)(O$R^{10}$), phenyl, phenyl substituted by halogen, $C_1$-$C_6$ alkyl, or $C_1$-$C_6$ alkyl substituted by halogen, —OH or oxo; $R^5$ and $R^6$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6 membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6 membered heterocyclyl are each independently unsubstituted or substituted by halogen, oxo, —CN, —O$R^9$, —N$R^9$$R^{10}$, $C_1$-$C_6$ alkyl, or $C_1$-$C_6$ alkyl substituted by halogen, —OH or oxo; and $R^7$, $R^8$, $R^9$ and $R^{10}$ are each independently hydrogen, $C_1$-$C_6$ alkyl, $C_2$-$C_6$ alkenyl, $C_2$-$C_6$ alkynyl, $C_1$-$C_6$ alkyl substituted by one or more halogen, $C_2$-$C_6$ alkenyl substituted by one or more halogen, or $C_2$-$C_6$ alkynyl substituted by one or more halogen.

In some embodiments of Formula (I), $R^1$, $R^2$, and $R^3$ are each independently hydrogen, hydroxy, halogen, optionally substituted $C_{1-4}$ alkyl, optionally substituted $C_{1-4}$ alkoxy, or —N$R^y$$R^z$. In certain instances, for each of $R^1$, $R^2$, and $R^3$, the $C_{1-4}$ alkyl or $C_{1-4}$ alkoxy groups are substituted with one or more substituents selected from the group consisting of hydroxyl, halogen, —N$R^f$$R^g$, cyano, nitro, $C_{1-4}$ alkoxy, and $C_{1-4}$ haloalkoxy, wherein $R^f$ and $R^g$ are each independently H, $C_{1-4}$alkyl, —C(O)$C_{1-4}$alkyl, —C(O)O$C_{1-4}$alkyl, or —S(O)$_2$$C_{1-4}$alkyl.

In some embodiments, one or more of $R^1$, $R^2$, or $R^3$ is $C_{1-4}$ alkyl, which is unsubstituted or substituted with one or more substituents selected from the group consisting of halogen, —CN, —O$R^4$, —S$R^4$, —N$R^5$$R^6$, —NO$_2$, —C=NH(O$R^4$), —C(O)$R^4$, —OC(O)$R^4$, —C(O)O$R^4$, —C(O)N$R^5$$R^6$, —OC(O)N$R^5$$R^6$, —N$R^4$C(O)$R^5$, —N$R^4$C(O)O$R^5$, —N$R^4$C(O)N$R^5$$R^6$, —S(O)$R^4$, —S(O)$_2$$R^4$, —N$R^4$S(O)$R^5$, —C(O)N$R^4$S(O)$R^5$, —N$R^4$S(O)$_2$$R^5$, —C(O)N$R^4$S(O)$_2$$R^5$, —S(O)N$R^5$$R^6$, —S(O)$_2$N$R^5$$R^6$, —P(O)(O$R^5$) (O$R^6$), $C_3$-$C_6$ cycloalkyl, 3-12-membered heterocyclyl, 5- to 10-membered heteroaryl, and $C_6$-$C_{14}$ aryl; wherein $R^4$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6-membered heterocyclyl are independently optionally substituted by halogen, oxo, —CN, —O$R^9$, —N$R^9$$R^{10}$, —P(O)(O$R^9$)(O$R^{10}$), phenyl optionally substituted by halogen, or $C_1$-$C_6$ alkyl optionally substituted by halogen, —OH or oxo; $R^5$ and $R^6$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6 membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6 membered heterocyclyl are independently optionally substituted by halogen, oxo, —CN, —O$R^9$, —N$R^9$$R^{10}$ or $C_1$-$C_6$ alkyl optionally substituted by halogen, —OH or oxo; and $R^9$ and $R^{10}$ are each independently hydrogen, $C_1$-$C_6$ alkyl, $C_2$-$C_6$ alkenyl, $C_2$-$C_6$ alkynyl, $C_1$-$C_6$ alkyl substituted by one or more halogen, $C_2$-$C_6$ alkenyl substituted by one or more halogen, or $C_2$-$C_6$ alkynyl substituted by one or more halogen.

In some embodiments, one or more of $R^1$, $R^2$, or $R^3$ is $C_{1-4}$ alkoxy, which is unsubstituted or substituted with one or more substituents selected from the group consisting of $C_1$-$C_6$ alkyl, $C_2$-$C_6$ alkenyl, $C_2$-$C_6$ alkynyl, halogen, —CN, —O$R^4$, —S$R^4$, —N$R^5$$R^6$, —NO$_2$, —C=NH(O$R^4$), —C(O)$R^4$, —OC(O)$R^4$, —C(O)O$R^4$, —C(O)N$R^5$$R^6$, —OC(O)N$R^5$$R^6$, —N$R^4$C(O)$R^5$, —N$R^4$C(O)O$R^5$, —N$R^4$C(O)N$R^5$$R^6$, —S(O)$R^4$, —S(O)$_2$$R^4$, —N$R^4$S(O)$R^5$, —C(O)N$R^4$S(O)$R^5$, —N$R^4$S(O)$_2$$R^5$, —C(O)N$R^4$S(O)$_2$$R^5$, —S(O)

$NR^5R^6$, $-S(O)_2NR^5R^6$, $-P(O)(OR^5)(OR^6)$, $C_3$-$C_6$ cycloalkyl, 3-12-membered heterocyclyl, 5- to 10-membered heteroaryl, and $C_6$-$C_{14}$ aryl; wherein $R^4$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6-membered heterocyclyl are independently optionally substituted by halogen, oxo, —CN, —$OR^9$, —$NR^9R^{10}$, —$P(O)(OR^9)(OR^{10})$, phenyl optionally substituted by halogen, or $C_1$-$C_6$ alkyl optionally substituted by halogen, —OH or oxo; and $R^5$ and $R^6$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6 membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6 membered heterocyclyl are independently optionally substituted by halogen, oxo, —CN, —$OR^9$, —$NR^9R^{10}$ or $C_1$-$C_6$ alkyl optionally substituted by halogen, —OH or oxo; and $R^9$ and $R^{10}$ are each independently hydrogen, $C_1$-$C_6$ alkyl, $C_2$-$C_6$ alkenyl, $C_2$-$C_6$ alkynyl, $C_1$-$C_6$ alkyl substituted by one or more halogen, $C_2$-$C_6$ alkenyl substituted by one or more halogen, or $C_2$-$C_6$ alkynyl substituted by one or more halogen.

In some embodiments, $R^1$ is hydrogen, hydroxy, halogen, optionally substituted $C_{1-4}$ alkyl, optionally substituted $C_{1-4}$ alkoxy, or —$NR^yR^z$. In some embodiments, $R^1$ is hydrogen. In some embodiments, $R^1$ is hydroxyl. In some embodiments, $R^1$ is halogen. In some embodiments, $R^1$ is chloro. In some embodiments, $R^1$ is fluoro. In other embodiments, $R^1$ is bromo or iodo. In some embodiments, $R^1$ is optionally substituted $C_{1-4}$ alkyl. In some embodiments, $R^1$ is $C_{1-4}$ alkyl substituted with one or more substituents selected from the group consisting of hydroxyl, halogen, —$NR^fR^g$, cyano, nitro, $C_{1-4}$ alkoxy, and $C_{1-4}$ haloalkoxy, wherein $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^1$ is $C_{1-4}$ alkyl substituted with one or more halogen groups. In some embodiments, $R^1$ is —$CF_3$, —$(CH_2)F$, —$CHF_2$, $CH_2Br$, —$CH_2CF_3$, —$CH_2CHF_2$, or —$CH_2CH_2F$. In some embodiments, $R^1$ is $CF_3$. In some embodiments, $R^1$ is unsubstituted $C_{1-4}$ alkyl. For instance, in some embodiments, $R^1$ is methyl, ethyl, propyl, isopropyl, butyl, isobutyl, secbutyl, or tertbutyl.

In other embodiments, $R^1$ is —$NR^yR^z$, wherein $R^y$ and $R^z$ taken together with the nitrogen to which they are attached form an optionally substituted monocyclic heterocycloalkyl ring. In some embodiments, $R^1$ is —$NR^yR^z$, wherein $R^y$ and $R^z$ taken together with the nitrogen to which they are attached form an optionally substituted 5- to 12-membered heterocycloalkyl ring. In some embodiments, $R^1$ is —$NR^yR^z$, wherein $R^y$ and $R^z$ taken together with the nitrogen to which they are attached form an optionally substituted 5- to 6-membered heterocycloalkyl ring. In some embodiments, $R^1$ is morpholinyl. In some embodiments, $R^1$ is morpholinyl substituted with one or more substituents selected from the group consisting of $C_1$-$C_6$ alkyl, $C_2$-$C_6$ alkenyl, $C_2$-$C_6$ alkynyl, hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^1$ is piperazinyl. In some embodiments, $R^1$ is piperazinyl substituted with one or more substituents selected from the group consisting of $C_1$-$C_6$ alkyl, $C_2$-$C_6$ alkenyl, $C_2$-$C_6$ alkynyl, hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^1$ is piperadinyl. In some embodiments, $R^1$ is piperadinyl substituted with one or more substituents selected from the group consisting of $C_1$-$C_6$ alkyl, $C_2$-$C_6$ alkenyl, $C_2$-$C_6$ alkynyl, hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^1$ is pyrrolidinyl. In some embodiments, $R^1$ is pyrrolidinyl substituted with one or more substituents selected from the group consisting of $C_1$-$C_6$ alkyl, $C_2$-$C_6$ alkenyl, $C_2$-$C_6$ alkynyl, hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl.

In some embodiments, $R^1$ is —$NR^yR^z$, wherein $R^y$ and $R^z$ are each independently H or optionally substituted $C_{1-4}$alkyl. In some embodiments, $R^1$ is —$NR^yR^z$, wherein $R^y$ and $R^z$ are each H. In some embodiments, $R^1$ is —$NR^yR^z$, wherein $R^y$ and $R^z$ are each optionally substituted $C_{1-4}$alkyl. In some embodiments, $R^1$ is —$NR^yR^z$, wherein $R^y$ and $R^z$ are each optionally $C_{1-4}$alkyl substituted with one or more substituents selected from the group consisting of hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^1$ is —$NR^yR^z$, wherein $R^y$ and $R^z$ are each optionally unsubstituted $C_{1-4}$alkyl. In certain embodiments, $R^1$ is —$N(CH_2)_2$ or —$N(CH_2CH_3)_2$. In some embodiments, $R^1$ is —$NR^yR^z$, wherein $R^y$ and $R^z$ are each unsubstituted $C_{1-4}$alkyl or $C_{1-4}$alkyl substituted with one or more substituents selected from the group consisting of hydroxyl, halogen, —$NR^fR^g$, cyano, nitro, $C_{1-4}$ alkoxy, and $C_{1-4}$ haloalkoxy, wherein $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^1$ is —$NR^yR^z$, wherein one of $R^y$ and $R^z$ is H and the other is unsubstituted $C_{1-4}$alkyl. In other embodiments, $R^1$ is —$NR^yR^z$, wherein one of $R^y$ and $R^z$ is H and the other is $C_{1-4}$alkyl substituted with one or more substituents selected from the group consisting of hydroxyl, halogen, —$NR^fR^g$, cyano, nitro, $C_{1-4}$ alkoxy, and $C_{1-4}$ haloalkoxy, wherein $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^1$ is —$NR^yR^z$, wherein one or $R^y$ and $R^z$ is H and the other is $C_{1-4}$alkyl unsubstituted or substituted with hydroxyl. In certain embodiments, $R^1$ is —$NH(CH_2)_2OH$.

In some embodiments, $R^1$ is optionally substituted $C_{1-4}$ alkoxy. In some embodiments, $R^1$ is unsubstituted $C_{1-4}$ alkoxy. In other embodiments, $R^1$ is $C_{1-4}$ alkoxy substituted with one or more substituents selected from the group consisting of $C_1$-$C_6$ alkyl, $C_2$-$C_6$ alkenyl, $C_2$-$C_6$ alkynyl, hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In certain embodiments, $R^1$ is $C_{1-4}$ alkoxy further substituted with $C_{1-4}$ alkoxy. For instance, in some embodiments, $R^1$ is —OCH$_2$CH$_2$OCH$_2$CH$_3$ or —OCH$_2$CH$_2$OCH$_3$. In other embodiments, $R^1$ is $C_{1-4}$ alkoxy substituted with optionally substituted $C_{1-4}$ alkoxy. In some embodiments, $R^1$ is —(OCH$_2$CH$_2$)$_p$—O—CH$_2$CH$_3$, wherein p is 0-10. In other embodiments, $R^1$ is —(OCH$_2$CH$_2$)$_p$—O—CH$_3$, wherein p is 0-10.

In some embodiments, $R^2$ is hydrogen, hydroxy, halogen, optionally substituted $C_{1-4}$ alkyl, optionally substituted $C_{1-4}$ alkoxy, or —NR$^x$R$^y$. In some embodiments, $R^2$ is hydrogen. In some embodiments, $R^2$ is hydroxyl. In some embodiments, $R^2$ is halogen. In some embodiments, $R^2$ is chloro. In some embodiments, $R^2$ is fluoro. In other embodiments, $R^2$ is bromo or iodo. In some embodiments, $R^2$ is optionally substituted $C_{1-4}$ alkyl. In some embodiments, $R^2$ is $C_{1-4}$ alkyl substituted with one or more substituents selected from the group consisting of hydroxyl, halogen, —NR$^f$R$^g$, cyano, nitro, $C_{1-4}$ alkoxy, and $C_{1-4}$ haloalkoxy, wherein R$^f$ and R$^g$ are each independently H, $C_{1-4}$alkyl, —C(O)C$_{1-4}$alkyl, —C(O)OC$_{1-4}$alkyl, or —S(O)$_2$C$_{1-4}$alkyl. In some embodiments, $R^2$ is $C_{1-4}$ alkyl substituted with one or more halogen groups. In some embodiments, $R^2$ is —CF$_3$, —(CH$_2$)F, —CHF$_2$, CH$_2$Br, —CH$_2$CF$_3$, —CH$_2$CHF$_2$, or —CH$_2$CH$_2$F. In some embodiments, $R^2$ is CF$_3$. In some embodiments, $R^2$ is unsubstituted $C_{1-4}$ alkyl. For instance, in some embodiments, $R^2$ is methyl, ethyl, propyl, isopropyl, butyl, isobutyl, secbutyl, or tertbutyl.

In some embodiments, $R^2$ is —NR$^y$R$^z$, wherein R$^y$ and R$^z$ taken together with the nitrogen to which they are attached form an optionally substituted monocyclic heterocycloalkyl ring. In some embodiments, $R^2$ is —NR$^y$R$^z$, wherein R$^y$ and R$^z$ taken together with the nitrogen to which they are attached form an optionally substituted 5- to 12-membered heterocycloalkyl ring. In some embodiments, $R^2$ is —NR$^y$R$^z$, wherein R$^y$ and R$^z$ taken together with the nitrogen to which they are attached form an optionally substituted 5- to 6-membered heterocycloalkyl ring. In some embodiments, $R^2$ is morpholinyl. In some embodiments, $R^2$ is morpholinyl substituted with one or more substituents selected from the group consisting of $C_1$-$C_6$ alkyl, $C_2$-$C_6$ alkenyl, $C_2$-$C_6$ alkynyl, hydroxyl, halogen, —NR$^f$R$^g$, cyano, nitro, $C_{1-4}$ alkoxy, $C_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or $C_{1-4}$alkyl and R$^f$ and R$^g$ are each independently H, $C_{1-4}$alkyl, —C(O)C$_{1-4}$alkyl, —C(O)OC$_{1-4}$alkyl, or —S(O)$_2$C$_{1-4}$alkyl. In some embodiments, $R^2$ is piperazinyl. In some embodiments, $R^2$ is piperazinyl substituted with one or more substituents selected from the group consisting of $C_1$-$C_6$ alkyl, $C_2$-$C_6$ alkenyl, $C_2$-$C_6$ alkynyl, hydroxyl, halogen, —NR$^f$R$^g$, cyano, nitro, $C_{1-4}$ alkoxy, $C_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or $C_{1-4}$alkyl and R$^f$ and R$^g$ are each independently H, $C_{1-4}$alkyl, —C(O)C$_{1-4}$alkyl, —C(O)OC$_{1-4}$alkyl, or —S(O)$_2$C$_{1-4}$alkyl. In some embodiments, $R^2$ is piperadinyl. In some embodiments, $R^2$ is piperadinyl substituted with one or more substituents selected from the group consisting of $C_1$-$C_6$ alkyl, $C_2$-$C_6$ alkenyl, $C_2$-$C_6$ alkynyl, hydroxyl, halogen, —NR$^f$R$^g$, cyano, nitro, $C_{1-4}$ alkoxy, $C_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or $C_{1-4}$alkyl and R$^f$ and R$^g$ are each independently H, $C_{1-4}$alkyl, —C(O)C$_{1-4}$alkyl, —C(O)OC$_{1-4}$alkyl, or —S(O)$_2$C$_{1-4}$alkyl. In some embodiments, $R^2$ is pyrrolidinyl. In some embodiments, $R^2$ is pyrrolidinyl substituted with one or more substituents selected from the group consisting of $C_1$-$C_6$ alkyl, $C_2$-$C_6$ alkenyl, $C_2$-$C_6$ alkynyl, hydroxyl, halogen, —NR$^f$R$^g$, cyano, nitro, $C_{1-4}$ alkoxy, $C_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or $C_{1-4}$alkyl and R$^f$ and R$^g$ are each independently H, $C_{1-4}$alkyl, —C(O)C$_{1-4}$alkyl, —C(O)OC$_{1-4}$alkyl, or —S(O)$_2$C$_{1-4}$alkyl.

In some embodiments, $R^2$ is —NR$^y$R$^z$, wherein R$^y$ and R$^z$ are each independently H or optionally substituted $C_{1-4}$alkyl. In some embodiments, $R^2$ is —NR$^y$R$^z$, wherein R$^y$ and R$^z$ are each H. In some embodiments, $R^2$ is —NR$^y$R$^z$, wherein R$^y$ and R$^z$ are each optionally substituted $C_{1-4}$alkyl. In some embodiments, $R^2$ is —NR$^y$R$^z$, wherein R$^y$ and R$^z$ are each optionally $C_{1-4}$alkyl substituted with one or more substituents selected from the group consisting of hydroxyl, halogen, —NR$^f$R$^g$, cyano, nitro, $C_{1-4}$ alkoxy, $C_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or $C_{1-4}$alkyl and R$^f$ and R$^g$ are each independently H, $C_{1-4}$alkyl, —C(O)C$_{1-4}$alkyl, —C(O)OC$_{1-4}$alkyl, or —S(O)$_2$C$_{1-4}$alkyl. In some embodiments, $R^2$ is —NR$^y$R$^z$, wherein R$^y$ and R$^z$ are each optionally unsubstituted $C_{1-4}$alkyl. In certain embodiments, $R^2$ is —N(CH$_2$)$_2$ or —N(CH$_2$CH$_3$)$_2$. In some embodiments, $R^2$ is —NR$^y$R$^z$, wherein R$^y$ and R$^z$ are each unsubstituted $C_{1-4}$alkyl or $C_{1-4}$alkyl substituted with one or more substituents selected from the group consisting of hydroxyl, halogen, —NR$^f$R$^g$, cyano, nitro, $C_{1-4}$ alkoxy, and $C_{1-4}$ haloalkoxy, wherein R$^f$ and R are each independently H, $C_{1-4}$alkyl, —C(O)C$_{1-4}$alkyl, —C(O)OC$_{1-4}$alkyl, or —S(O)$_2$C$_{1-4}$alkyl. In some embodiments, $R^2$ is —NR$^y$R$^z$, wherein one of R$^y$ and R$^z$ is H and the other is unsubstituted $C_{1-4}$alkyl. In other embodiments, $R^2$ is —NR$^y$R$^z$, wherein one of R$^y$ and R$^z$ is H and the other is $C_{1-4}$alkyl substituted with one or more substituents selected from the group consisting of hydroxyl, halogen, —NR$^f$R$^g$, cyano, nitro, $C_{1-4}$ alkoxy, and $C_{1-4}$ haloalkoxy, wherein R$^f$ and R$^g$ are each independently H, $C_{1-4}$alkyl, —C(O)C$_{1-4}$alkyl, —C(O)OC$_{1-4}$alkyl, or —S(O)$_2$C$_{1-4}$alkyl. In some embodiments, $R^2$ is —NR$^y$R$^z$, wherein one or R$^y$ and R$^z$ is H and the other is $C_{1-4}$alkyl unsubstituted or substituted with hydroxyl. In certain embodiments, $R^2$ is —NH(CH$_2$)$_2$OH.

In some embodiments, $R^2$ is optionally substituted $C_{1-4}$ alkoxy. In some embodiments, $R^2$ is unsubstituted $C_{1-4}$ alkoxy. In other embodiments, $R^2$ is $C_{1-4}$ alkoxy substituted with one or more substituents selected from the group consisting of $C_1$-$C_6$ alkyl, $C_2$-$C_6$ alkenyl, $C_2$-$C_6$ alkynyl, hydroxyl, halogen, —NR$^f$R$^g$, cyano, nitro, $C_{1-4}$ alkoxy, $C_{1-4}$ haloalkoxy, —C(O)R$^4$, —OC(O)R$^4$, —C(O)OR$^4$, —C(O)NR$^f$R$^g$, and —OC(O)NR$^f$R$^g$, wherein R$^4$ is H or $C_{1-4}$alkyl and R$^f$ and R$^g$ are each independently H, $C_{1-4}$alkyl, —C(O)C$_{1-4}$alkyl, —C(O)OC$_{1-4}$alkyl, or —S(O)$_2$C$_{1-4}$alkyl. In certain embodiments, $R^2$ is $C_{1-4}$ alkoxy further substituted with $C_{1-4}$ alkoxy. For instance, in some embodiments, $R^2$ is —OCH$_2$CH$_2$OCH$_2$CH$_3$ or —OCH$_2$CH$_2$OCH$_3$. In other embodiments, $R^2$ is $C_{1-4}$ alkoxy substituted with optionally substituted $C_{1-4}$ alkoxy. In some embodiments, $R^2$ is —(OCH$_2$CH$_2$)$_p$—O—CH$_2$CH$_3$, wherein p is 0-10. In other embodiments, $R^2$ is —(OCH$_2$CH$_2$)$_p$—O—CH$_3$, wherein p is 0-10.

In some embodiments, $R^3$ is hydrogen, hydroxy, halogen, optionally substituted $C_{1-4}$ alkyl, optionally substituted $C_{1-4}$ alkoxy, or —NR$^x$R$^y$. In certain instances, the $C_{1-4}$ alkyl or $C_{1-4}$ alkoxy groups are substituted with one or more substituents selected from the group consisting of hydroxyl, halogen, —NR$^f$R$^g$, cyano, nitro, $C_{1-4}$ alkoxy, and $C_{1-4}$ haloalkoxy, wherein R$^f$ and R$^g$ are each independently H, $C_{1-4}$alkyl, —C(O)C$_{1-4}$alkyl, —C(O)OC$_{1-4}$alkyl, or —S(O)$_2$C$_{1-4}$alkyl. In some embodiments, $R^3$ is hydrogen. In some embodiments, $R^3$ is hydroxyl. In some embodiments, $R^3$ is halogen. In some embodiments, $R^3$ is chloro. In some embodiments, $R^3$ is fluoro. In other embodiments, $R^3$ is bromo or iodo. In some embodiments, $R^3$ is optionally substituted $C_{1-4}$ alkyl. In some embodiments, $R^3$ is $C_{1-4}$ alkyl substituted with one or more substituents selected from the group consisting of hydroxyl, halogen, —$NR^fR^g$, cyano, nitro, $C_{1-4}$ alkoxy, and $C_{1-4}$ haloalkoxy, wherein $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^3$ is $C_{1-4}$ alkyl substituted with one or more halogen groups. In some embodiments, $R^3$ is —$CF_3$, —$(CH_2)F$, —$CHF_2$, $CH_2Br$, —$CH_2CF_3$, —$CH_2CHF_2$, or —$CH_2CH_2F$. In some embodiments, $R^3$ is $CF_3$. In some embodiments, $R^3$ is unsubstituted $C_{1-4}$ alkyl. For instance, in some embodiments, $R^3$ is methyl, ethyl, propyl, isopropyl, butyl, isobutyl, secbutyl, or tertbutyl.

In some embodiments, $R^3$ is —$NR^yR^z$, wherein $R^y$ and $R^z$ taken together with the nitrogen to which they are attached form an optionally substituted monocyclic heterocycloalkyl ring. In some embodiments, $R^3$ is —$NR^yR^z$, wherein $R^y$ and $R^z$ taken together with the nitrogen to which they are attached form an optionally substituted 5- to 12-membered heterocycloalkyl ring. In some embodiments, $R^3$ is —$NR^yR^z$, wherein $R^y$ and $R^z$ taken together with the nitrogen to which they are attached form an optionally substituted 5- to 6-membered heterocycloalkyl ring. In some embodiments, $R^3$ is morpholinyl. In some embodiments, $R^3$ is morpholinyl substituted with one or more substituents selected from the group consisting of $C_1$-$C_6$ alkyl, $C_2$-$C_6$ alkenyl, $C_2$-$C_6$ alkynyl, hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^3$ is piperazinyl. In some embodiments, $R^3$ is piperazinyl substituted with one or more substituents selected from the group consisting of $C_1$-$C_6$ alkyl, $C_2$-$C_6$ alkenyl, $C_2$-$C_6$ alkynyl, hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^3$ is piperadinyl. In some embodiments, $R^3$ is piperadinyl substituted with one or more substituents selected from the group consisting of $C_1$-$C_6$ alkyl, $C_2$-$C_6$ alkenyl, $C_2$-$C_6$ alkynyl, hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^3$ is pyrrolidinyl. In some embodiments, $R^3$ is pyrrolidinyl substituted with one or more substituents selected from the group consisting of $C_1$-$C_6$ alkyl, $C_2$-$C_6$ alkenyl, $C_2$-$C_6$ alkynyl, hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl.

In some embodiments, $R^3$ is —$NR^yR^z$, wherein $R^y$ and $R^z$ are each independently H or optionally substituted $C_{1-4}$alkyl. In some embodiments, $R^3$ is —$NR^yR^z$, wherein $R^y$ and $R^z$ are each H. In some embodiments, $R^3$ is —$NR^yR^z$, wherein $R^y$ and $R^z$ are each optionally substituted $C_{1-4}$alkyl. In some embodiments, $R^3$ is —$NR^yR^z$, wherein $R^y$ and $R^z$ are each optionally $C_{1-4}$alkyl substituted with one or more substituents selected from the group consisting of hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^3$ is —$NR^yR^z$, wherein $R^y$ and $R^z$ are each optionally unsubstituted $C_{1-4}$alkyl. In certain embodiments, $R^3$ is —$N(CH_2)_2$ or —$N(CH_2CH_3)_2$. In some embodiments, $R^3$ is —$NR^yR^z$, wherein $R^y$ and $R^z$ are each unsubstituted $C_{1-4}$alkyl or $C_{1-4}$alkyl substituted with one or more substituents selected from the group consisting of hydroxyl, halogen, —$NR^fR^g$, cyano, nitro, $C_{1-4}$ alkoxy, and $C_{1-4}$ haloalkoxy, wherein $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^3$ is —$NR^yR^z$, wherein one of $R^y$ and $R^z$ is H and the other is unsubstituted $C_{1-4}$alkyl. In other embodiments, $R^3$ is —$NR^yR^z$, wherein one of $R^y$ and $R^z$ is H and the other is $C_{1-4}$alkyl substituted with one or more substituents selected from the group consisting of hydroxyl, halogen, —$NR^fR^g$, cyano, nitro, $C_{1-4}$ alkoxy, and $C_{1-4}$ haloalkoxy, wherein $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In some embodiments, $R^3$ is —$NR^yR^z$, wherein one or $R^y$ and $R^z$ is H and the other is $C_{1-4}$alkyl unsubstituted or substituted with hydroxyl. In certain embodiments, $R^3$ is —$NH(CH_2)_2OH$.

In some embodiments, $R^3$ is optionally substituted $C_{1-4}$ alkoxy. In some embodiments, $R^3$ is unsubstituted $C_{1-4}$ alkoxy. In other embodiments, $R^3$ is $C_{1-4}$ alkoxy substituted with one or more substituents selected from the group consisting of $C_1$-$C_6$ alkyl, $C_2$-$C_6$ alkenyl, $C_2$-$C_6$ alkynyl, hydroxyl, halogen, —$NR^fR^g$, cyano, nitro, $C_{1-4}$ alkoxy, $C_{1-4}$ haloalkoxy, —$C(O)R^4$, —$OC(O)R^4$, —$C(O)OR^4$, —$C(O)NR^fR^g$, and —$OC(O)NR^fR^g$, wherein $R^4$ is H or $C_{1-4}$alkyl and $R^f$ and $R^g$ are each independently H, $C_{1-4}$alkyl, —$C(O)C_{1-4}$alkyl, —$C(O)OC_{1-4}$alkyl, or —$S(O)_2C_{1-4}$alkyl. In certain embodiments, $R^3$ is $C_{1-4}$ alkoxy further substituted with $C_{1-4}$ alkoxy. For instance, in some embodiments, $R^3$ is —$OCH_2CH_2OCH_2CH_3$ or —$OCH_2CH_2OCH_3$. In other embodiments, $R^3$ is $C_{1-4}$ alkoxy substituted with optionally substituted $C_{1-4}$ alkoxy. In some embodiments, $R^3$ is —$(OCH_2CH_2)_p$—$O$—$CH_2CH_3$, wherein p is 0-10. In other embodiments, $R^3$ is —$(OCH_2CH_2)_p$—$O$—$CH_3$, wherein p is 0-10.

In some embodiments, $R^1$, $R^2$, and $R^3$ are independently selected from the group consisting of H, —Cl, —CN, —$CF_3$, methyl, methoxy, —$NHCH_2CH_2OH$, —$N(CH_2CH_3)_2$, —$N(CH_3)_2$, —$OCH_2CH_2$—$O$—$CH_2CH_3$, —$OCH_2CH_2OCH_3$, morpholinyl, 4-methyl-piperazin-1-yl, piperidinyl, and pyrrolidinyl. In some embodiments, $R^1$ is selected from the group consisting of H, —$NHCH_2CH_2OH$, —$N(CH_2CH_3)_2$, morpholinyl, 4-methyl-piperazin-1-yl, piperidinyl, pyrrolidinyl, —$OCH_2CH_2$—$O$—$CH_2CH_3$, and —$OCH_2CH_2OCH_3$. In some embodiments, $R^2$ is selected from the group consisting of H, —$CF_3$, —CN, methyl, methoxy, —$OCH_2CH_2$—$O$—$CH_2CH_3$, —$OCH_2CH_2OCH_3$, —$N(CH_3)_2$, and morpholinyl. In some embodiments, $R^3$ is selected from the group consisting of H, —Cl, —CN, methyl, methoxy, and morpholinyl.

It is understood that the descriptions of any variable of Formula (I) may, where applicable, be combined with one or more descriptions of any other variable, the same as if each and every combination of variables were specifically and individually listed. For example, every description of $R^1$ may be combined with every description of $R^2$ and $R^3$ the same as if each and every combination were specifically and individually listed. Likewise, every description of $R^2$ may be combined with every description of $R^1$ and $R^3$ the same as if each and every description were specifically and individually listed, and every description of $R^3$ may be combined with every description of $R^1$ and $R^2$ the same as if each and every description were specifically and individually listed.

In some embodiments, the compound of Formula (I) is a compound shown in the following table

| Compound No. | Structure | Name |
|---|---|---|
| 1 | 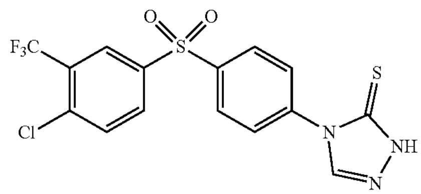 [SMILES: O=S(=O)(c1ccc(-n2cn[nH]c2=S)cc1)c1ccc(Cl)c(C(F)(F)F)c1] | 4-(4-((4-chloro-3-(trifluoromethyl)phenyl)sulfonyl)phenyl)-2,4-dihydro-3H-1,2,4-triazole-3-thione |
| 2 | 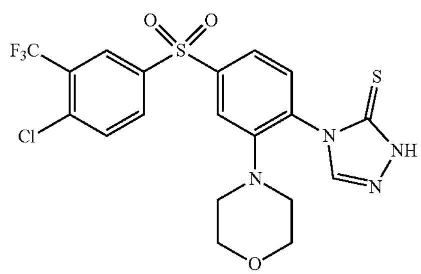 | 4-(4-((4-chloro-3-(trifluoromethyl)phenyl)sulfonyl)-2-morpholinophenyl)-2,4-dihydro-3H-1,2,4-triazole-3-thione |
| 3 | 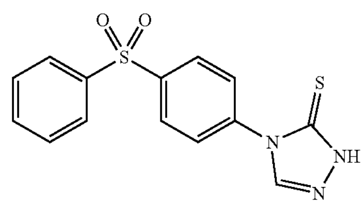 [SMILES: O=S(=O)(c1ccccc1)c1ccc(-n2cn[nH]c2=S)cc1] | 4-(4-(phenylsulfonyl)phenyl)-2,4-dihydro-3H-1,2,4-triazole-3-thione |
| 4 | 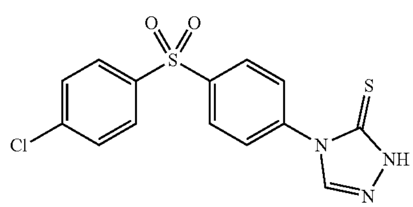 [SMILES: O=S(=O)(c1ccc(Cl)cc1)c1ccc(-n2cn[nH]c2=S)cc1] | 4-(4-((4-chlorophenyl)sulfonyl)phenyl)-2,4-dihydro-3H-1,2,4-triazole-3-thione |
| 5 | 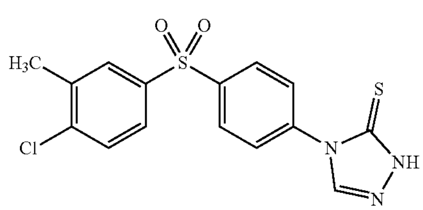 | 4-(4-((4-chloro-3-methylphenyl)sulfonyl)phenyl)-2,4-dihydro-3H-1,2,4-triazole-3-thione |
| 6 | 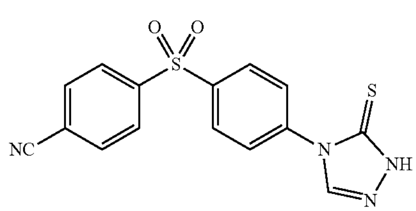 [SMILES: N#Cc1ccc(S(=O)(=O)c2ccc(-n3cn[nH]c3=S)cc2)cc1] | 4-((4-(5-thioxo-1,5-dihydro-4H-1,2,4-triazol-4-yl)phenyl)sulfonyl)benzonitrile |

-continued

| Compound No. | Structure | Name |
|---|---|---|
| 7 | 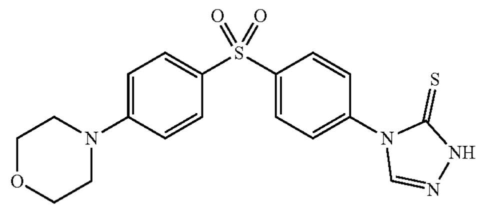 [SMILES: O=S(=O)(c1ccc(N2CCOCC2)cc1)c1ccc(-n2cn[nH]c2=S)cc1] | 4-(4-((4-morpholinophenyl)sulfonyl)phenyl)-2,4-dihydro-3H-1,2,4-triazole-3-thione |
| 8 | 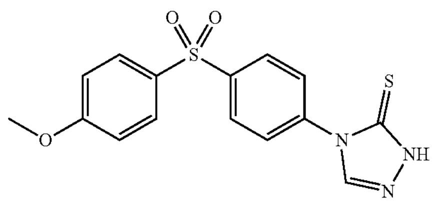 [SMILES: COc1ccc(S(=O)(=O)c2ccc(-n3cn[nH]c3=S)cc2)cc1] | 4-(4-((4-methoxyphenyl)sulfonyl)phenyl)-2,4-dihydro-3H-1,2,4-triazole-3-thione |
| 9 | 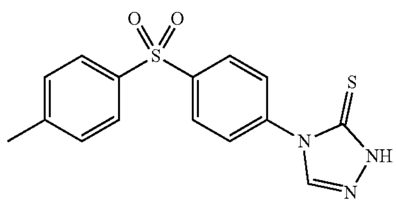 [SMILES: Cc1ccc(S(=O)(=O)c2ccc(-n3cn[nH]c3=S)cc2)cc1] | 4-(4-tosylphenyl)-2,4-dihydro-3H-1,2,4-triazole-3-thione |
| 10 | 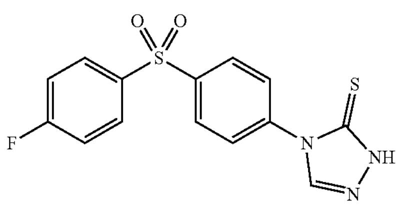 [SMILES: O=S(=O)(c1ccc(F)cc1)c1ccc(-n2cn[nH]c2=S)cc1] | 4-(4-((4-fluorophenyl)sulfonyl)phenyl)-2,4-dihydro-3H-1,2,4-triazole-3-thione |
| 11 | 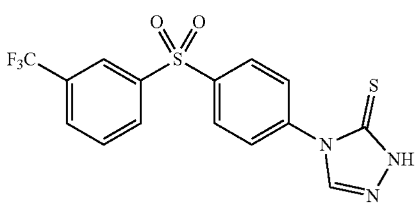 [SMILES: O=S(=O)(c1ccc(-n2cn[nH]c2=S)cc1)c1cccc(C(F)(F)F)c1] | 4-(4-((3-(trifluoromethyl)phenyl)sulfonyl)phenyl)-2,4-dihydro-3H-1,2,4-triazole-3-thione |
| 12 | 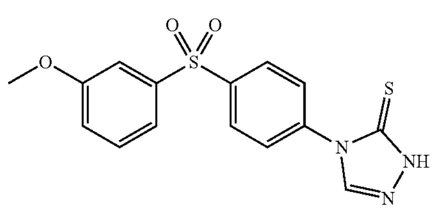 [SMILES: COc1cccc(S(=O)(=O)c2ccc(-n3cn[nH]c3=S)cc2)c1] | 4-(4-((3-methoxyphenyl)sulfonyl)phenyl)-2,4-dihydro-3H-1,2,4-triazole-3-thione |
| 13 | 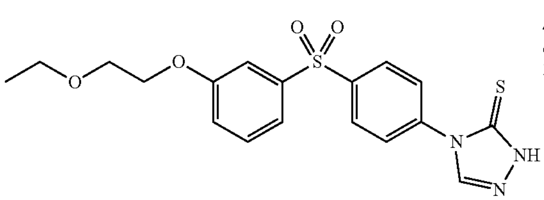 | 4-(4-((3-(2-ethoxyethoxy)phenyl)sulfonyl)phenyl)-2,4-dihydro-3H-1,2,4-triazole-3-thione |

-continued

| Compound No. | Structure | Name |
|---|---|---|
| 14 | 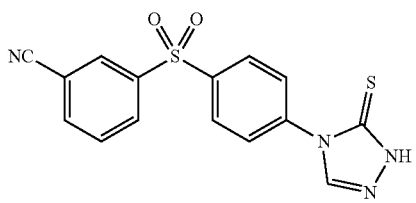 [SMILES: N#Cc1cccc(S(=O)(=O)c2ccc(-n3cn[nH]c3=S)cc2)c1] | 3-((4-(5-thioxo-1,5-dihydro-4H-1,2,4-triazol-4-yl)phenyl)sulfonyl)benzonitrile |
| 15 | 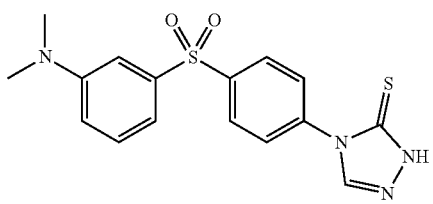 | 4-(4-((3-(dimethylamino)phenyl)sulfonyl)phenyl)-2,4-dihydro-3H-1,2,4-triazole-3-thione |
| 16 | 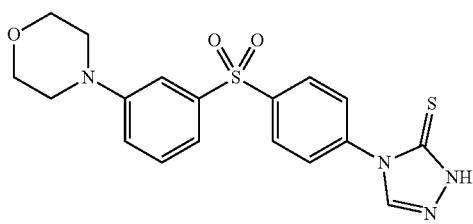 [SMILES: O=S(=O)(c1ccc(-n2cn[nH]c2=S)cc1)c1cccc(N2CCOCC2)c1] | 4-(4-((3-morpholinophenyl)sulfonyl)phenyl)-2,4-dihydro-3H-1,2,4-triazole-3-thione |
| 17 | 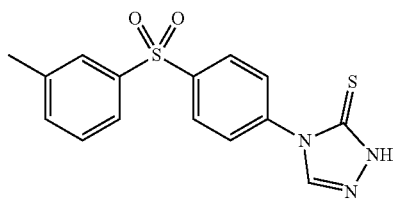 [SMILES: Cc1cccc(S(=O)(=O)c2ccc(-n3cn[nH]c3=S)cc2)c1] | 4-(4-(m-tolylsulfonyl)phenyl)-2,4-dihydro-3H-1,2,4-triazole-3-thione |
| 18 | 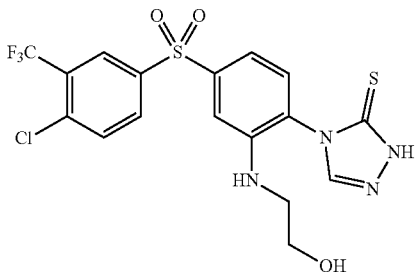 [SMILES: O=S(=O)(c1ccc(-n2cn[nH]c2=S)c(NCCO)c1)c1ccc(Cl)c(C(F)(F)F)c1] | 4-(4-((4-chloro-3-(trifluoromethyl)phenyl)sulfonyl)-2-((2-hydroxyethyl)amino)phenyl)-2,4-dihydro-3H-1,2,4-triazole-3-thione |
| 19 | 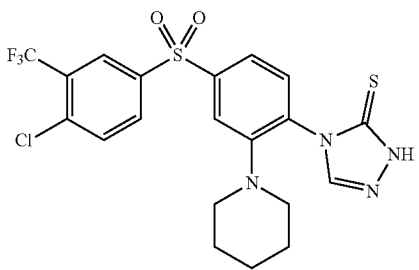 [SMILES: O=S(=O)(c1ccc(-n2cn[nH]c2=S)c(N2CCCCC2)c1)c1ccc(Cl)c(C(F)(F)F)c1] | 4-(4-((4-chloro-3-(trifluoromethyl)phenyl)sulfonyl)-2-(piperidin-1-yl)phenyl)-2,4-dihydro-3H-1,2,4-triazole-3-thione |

| Compound No. | Structure | Name |
|---|---|---|
| 20 | 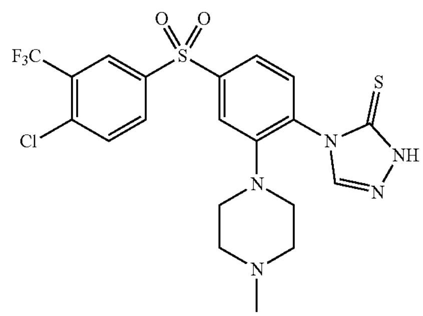 [SMILES: CN1CCN(c2cc(S(=O)(=O)c3ccc(Cl)c(C(F)(F)F)c3)ccc2-n2cn[nH]c2=S)CC1] | 4-(4-((4-chloro-3-(trifluoromethyl)phenyl)sulfonyl)-2-(4-methylpiperazin-1-yl)phenyl)-2,4-dihydro-3H-1,2,4-triazole-3-thione |
| 21 | 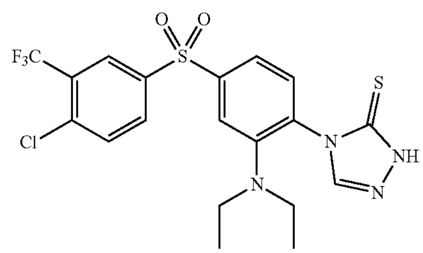 [SMILES: CCN(CC)c1cc(S(=O)(=O)c2ccc(Cl)c(C(F)(F)F)c2)ccc1-n1cn[nH]c1=S] | 4-(4-((4-chloro-3-(trifluoromethyl)phenyl)sulfonyl)-2-(diethylamino)phenyl)-2,4-dihydro-3H-1,2,4-triazole-3-thione |
| 22 | 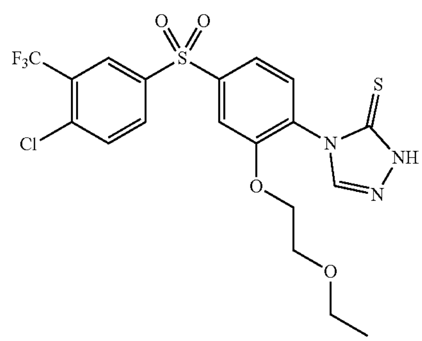 [SMILES: CCOCCOc1cc(S(=O)(=O)c2ccc(Cl)c(C(F)(F)F)c2)ccc1-n1cn[nH]c1=S] | 4-(4-((4-chloro-3-(trifluoromethyl)phenyl)sulfonyl)-2-(2-ethoxyethoxy)phenyl)-2,4-dihydro-3H-1,2,4-triazole-3-thione |
| 23 | 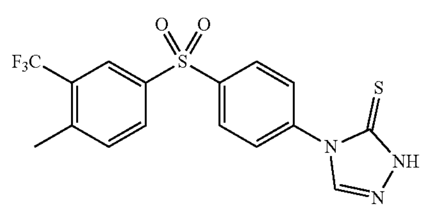 [SMILES: Cc1ccc(S(=O)(=O)c2ccc(-n3cn[nH]c3=S)cc2)cc1C(F)(F)F] | 4-(4-((4-methyl-3-(trifluoromethyl)phenyl)sulfonyl)phenyl)-2,4-dihydro-3H-1,2,4-triazole-3-thione |
| 24 | 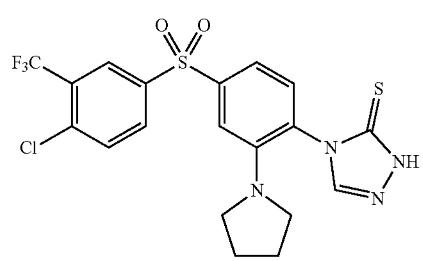 [SMILES: O=S(=O)(c1ccc(-n2cn[nH]c2=S)c(N2CCCC2)c1)c1ccc(Cl)c(C(F)(F)F)c1] | 4-(4-((4-chloro-3-(trifluoromethyl)phenyl)sulfonyl)-2-(pyrrolidin-1-yl)phenyl)-2,4-dihydro-3H-1,2,4-triazole-3-thione |

| Compound No. | Structure | Name |
|---|---|---|
| 25 | 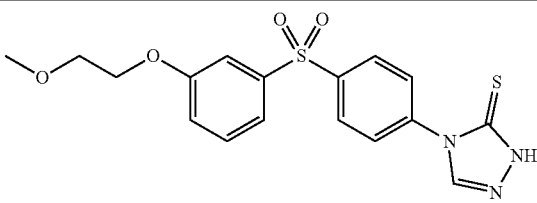 | 4-(4-((3-(2-methoxyethoxy)phenyl)sulfonyl)phenyl)-2,4-dihydro-3H-1,2,4-triazole-3-thione | or a pharmaceutically acceptable salt thereof.

The compounds of Formula (I) may be prepared and/or formulated as pharmaceutically acceptable salts. In some embodiments, pharmaceutically acceptable salts include acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like. These salts may be derived from inorganic or organic acids. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. In some embodiments, pharmaceutically acceptable salts are formed when an acidic proton present in the parent compound either is replaced by a metal ion, e.g., an alkali metal ion, an alkaline earth ion, or an aluminum ion; or coordinates with an organic base. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, trimetharnine, dicyclohexylamine, caffeine, procaine, hydrabamine, choline, betaine, ethylenediamine, glucosamine, N-ethylglucamine, N-methylglucamine, theobromine, purines, piperazine, piperidine, N-ethylpiperidine, polyamine resins, amino acids such as lysine, arginine, histidine, and the like. Examples of pharmaceutically acceptable base addition salts include those derived from inorganic bases such as sodium, potassium, lithium, ammonium, calcium, magnesium, iron, zinc, copper, manganese, aluminum salts and the like. In some embodiments, the organic non-toxic bases are L-amino acids, such as L-lysine and L-arginine, tromethamine, N-ethylglucamine and N-methylglucamine. Acceptable inorganic bases include aluminum hydroxide, calcium hydroxide, potassium hydroxide, sodium carbonate, sodium hydroxide, and the like. Lists of other suitable pharmaceutically acceptable salts are found in Remington's Pharmaceutical Sciences, 17th Edition, Mack Publishing Company, Easton, Pa., 1985.

For a compound described herein that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, benzenesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The embodiments also relate to pharmaceutically acceptable prodrugs of the compounds described herein, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The embodiments also relate to pharmaceutically active metabolites of compounds described herein, and uses of such metabolites in the methods provided herein. A "pharmaceutically active metabolite" means a pharmacologically active product of metabolism in the body of a compound described herein or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev.*

*Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Pharmaceutical Compositions

For treatment purposes, a pharmaceutical composition according to the present disclosure comprises at least one compound of Formula (I), or a pharmaceutically acceptable salt thereof. The pharmaceutical compositions may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In some embodiments, pharmaceutical compositions according to the embodiments are sterile compositions. Pharmaceutical compositions may be prepared using compounding techniques known or that become available to those skilled in the art.

Sterile compositions are also contemplated by the embodiments, including compositions that are in accord with national and local regulations governing such compositions.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions provided herein may be administered by a suitable route of delivery, such as oral, parenteral, rectal, nasal, topical, or ocular routes, or by inhalation. In some embodiments, the compositions are formulated for intravenous or oral administration.

For oral administration, the compounds the embodiments may be provided in a solid form, such as a tablet or capsule, or as a solution, emulsion, or suspension. To prepare the oral compositions, the compounds provided herein may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions described herein may be formulated for rectal administration as a suppository. For parenteral use, including intravenous, intramuscular, intraperitoneal, intranasal, or subcutaneous routes, the agents provided herein may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the compounds or pharmaceutical compositions described herein may be administered using, for example, a spray formulation also containing a suitable carrier.

In some embodiments, for topical applications, the compounds of the present embodiments are formulated as creams or ointments or a similar vehicle suitable for topical administration. For topical administration, the compounds or pharmaceutical compositions described herein may be mixed with a pharmaceutical carrier at a concentration of about 0.10% to about 10% of drug to vehicle. Another mode of administering the agents provided herein may utilize a patch formulation to effect transdermal delivery.

Spray Dry Formulations

In some embodiments, provided herein are pharmaceutical formulations containing the compounds of Formula (I) that optimize the bioavailability of the compound. In some embodiments, the pharmaceutical formulations are in the form of an amorphous dispersion. In some embodiments, the pharmaceutical formulations are spray dried to produce spray dried dispersions (SDDs). Spray drying is a process in which the compound and excipients are dissolved in a common solvent and the resulting solution is atomized into a drying chamber. Through this process, a liquid solution containing the compound is converted to a dried particulate form.

In some embodiments, spray drying involves contacting a liquid suspension or solution containing the one or more compounds of Formula (I) and one or more pharmaceutically acceptable excipients, and a sufficient volume of hot air to produce evaporation and drying of the liquid droplets. The preparation to be spray dried can be any solution, coarse suspension, slurry, colloidal dispersion, or paste that may be atomized using the selected spray drying apparatus. In some embodiments, the liquid suspension is sprayed into a current of warm filtered air that evaporates the solvent and conveys the dried product to a collector (e.g., a cyclone). The spent air is then exhausted with the solvent, or alternatively the spent air is sent to a condenser to capture and potentially recycle the solvent. Commercially available types of apparatus may be used to conduct the spray drying.

In some embodiments, the preparation to be spray dried contains about 3% to about 40% of the compound by weight, for example between about 3% and about 35%, between about 3% and about 30%, between about 3% and about 25%, between about 3% and about 20%, between about 3% and about 15%, between about 3% and about 10%, between about 3% and about 5%, between about 10% and about 35%, between about 10% and about 30%, between about 10% and about 25%, between about 10% and about 20%, between about 15% and about 35%, between about 15% and about 30%, between about 15% and about 25%, between about 15% and about 20%, between about 20% and about 35%, between about 20% and about 30%, between about 20% and about 25%, between about 25% and about 35%, between about 25% and about 30%, or between about 30% and about 40% by weight. In some embodiments, the spray dry formulation contains about 5% of the compound by weight. In some embodiments, the spray dry formulation contains about 10% of the compound by weight. In some embodiments, the spray dry formulation contains about 15% of the compound by weight. In some embodiments, the spray dry dispersion contains at least about 10% of the compound by weight. In general, the upper limit of solid loads is governed by the viscosity of (e.g., the ability to pump) the resulting solution and the solubility of the components in the solution. Generally, the viscosity of the solution can determine the size of the particle in the resulting powder product.

In some embodiments, the spray dry dispersion contains one or more compounds of Formula (I) and one or more pharmaceutically acceptable excipients. In some embodiments, the one or more pharmaceutically acceptable excipients include one or more binders. In some embodiments, the binder is polymeric. In some embodiments, the one or more binders is selected from the group consisting of polymeric cellulose derivatives, such as carboxymethyl cellulose (CMC), hydroxypropyl cellulose (HPC), hydroxyethyl cellulose (HEC) and hydroxypropylmethyl cellulose (HPMC); gelatin; gelatin hydrolysate; sucrose; dextrose; and non-cellulosic binders, such as polyvinylpyrrolidone (PVP), Polyvinylpyrrolidone/vinyl acetate (PVP/VA), polyethyleneglycol (PEG), vinyl pyrrolidone copolymers, pregelatinized starch, sorbitol, and glucose; methacrylate, and polyacrylates. In some embodiments, the one or more binders is selected from the group consisting of polyvinylpyrrolidone and its derivatives such as Kollidon; cellulose derivatives such as HPMC; and polyoxyethylene/polyethyleneglycol polymers such as PEG. In some embodiments, the one or more binders is selected from the group consisting of PVP, PVP/VA, and HPMC. In some embodiments, the one or more binders is selected from the group consisting of PVP-VA 64, HPMC E5, HPMC-AS, and Kollidon 30. In some embodiments, the binder includes PVP-VA 64. In some embodiments, the binder includes Kollidon 30. In some embodiments, the binder includes HMPC E5. In some embodiments, the binder includes HMPC-AS. In some embodiments, the spray dry dispersion contains at least one polymer and at least one compound of Formula (I). In some embodiments, the spray dry dispersion contains a polymer to compound ratio of from about 10:1 to about 1:1, such as from about 5:1 to about 2:1. In some embodiments, the spray dry solutions contain a polymer to compound ratio of about 3:1.

In some embodiments, the spray drying is conducted with an inlet temperature of from about 60° C. to about 200° C., for example, from about 95° C. to about 185° C., from about 110° C. to about 182° C., or from about 96° C. to about 180° C. In some embodiments, the spray drying is conducted with an inlet temperature of about 145° C. In some embodiments, the spray drying is conducted with an outlet temperature of from about 30° C. to about 90° C., such as from about 30° C. to about 80° C., about 30° C. to about 70° C., about 30° C. to about 60° C., or about 30° C. to about 50° C. In some embodiments, the spray drying is conducted with an outlet temperature of from about 35° C. to about 45° C. In some embodiments, the spray drying is conducted with an outlet temperature of from about 40° C. In some embodiments, the atomization flow rate is from about 1 g/min to about 50 g/min, such as from about 1 g/min to about 40 g/min, from about 1 g/min to about 30 g/min, from about 1 g/min to about 20 g/min, from about 1 g/min to about 10 g/min, from about 5 g/min to about 40 g/min, from about 5 g/min to about 30 g/min, from about 5 g/min to about 20 g/min, from about 5 g/min to about 10 g/min, from about 10 g/min to about 40 g/min, from about 10 g/min to about 30 g/min, from about 10 g/min to about 20 g/min, from about 20 g/min to about 40 g/min, from about 20 g/min to about 30 g/min, from about 30 g/min to about 40 g/min, or from about 40 g/min to about 50 g/min. In some embodiments, the atomization flow rate is from about 5 g/min to about 15 g/min, such as around 8 g/min or around 10 g/min.

In some embodiments, removal of the solvent may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.). In one embodiment, the solid dispersion is fluid bed dried.

In one embodiment of the spray dry process, the solvent includes a volatile solvent, for example a solvent having a boiling point of less than about 100° C. In some embodiments, the solvent includes a mixture of solvents, for example a mixture of volatile solvents or a mixture of volatile and non-volatile solvents. Where mixtures of solvents are used, the mixture can include one or more non-volatile solvents, for example, where the non-volatile solvent is present in the mixture at less than about 15%, e.g., less than about 12%, less than about 10%, less than about 8%, less than about 5%, less than about 3%, or less than about 2%.

In some embodiments, the compounds of Formula (I) have a solubility of at least about 10 mg/mL, (e.g., at least about 15 mg/mL, 20 mg/mL, 25 mg/mL, 30 mg/mL, 35 mg/mL, 40 mg/mL, 45 mg/mL, 50 mg/mL, or greater) in the solvent used for the spray drying procedure. In some embodiments, the compounds of Formula (I) have a solubility of at least about 20 mg/mL in the solvent used for the spray drying procedure.

Exemplary solvents that can be used in the spray dry procedure include acetone, cyclohexane, dichloromethane (DCM), N,N-dimethylacetamide (DMA), N,N-dimethylformamide (DMF), 1,3-dimethyl-2-imidazolidinone (DMI), dimethyl sulfoxide (DMSO), dioxane, ethyl acetate, ethyl ether, glacial acetic acid (HAc), methyl ethyl ketone (MEK), N-methyl-2-pyrrolidinone (NMP), methyl tert-butyl ether (MTBE), tetrahydrofuran (THF), pentane, acetonitrile, methanol, ethanol, isopropyl alcohol, isopropyl acetate, toluene, and water. Exemplary co-solvents include acetone/ THF, acetone/methanol, acetone/ethanol, acetone/ethyl acetate, acetone/DCM, acetone/DMSO, acetone/DMF, acetone/water, ethyl acetate/DCM, ethyl acetate/THF, ethyl acetate/methanol, ethyl acetate/ethanol, MEK/water, THF/ water, THF/methanol, THF/ethanol, dioxane/water, DCM/ methanol, DCM/ethanol, and DCM/THF. In a two solvent system, the solvents can be present in of from about 0.10% to about 99.9%. In some embodiments, DCM is used as a co-solvent with methanol at a ratio of about 90:10 to about 60:40, such as about 80:20. In some embodiments the solvent solution includes three solvents. For example, acetone and water can be mixed with a third solvent such as DMA, DMF, DMI, DMSO, or HAc. In some embodiments, the solvents used for the spray drying procedure dissolve both the compound and the polymer.

In some embodiments, the spray-dried dispersions (SDDs) contain about 10% to about 75% of the compound by weight, for example between about 10% and about 65%, between about 10% and about 55%, between about 10% and about 45%, between about 10% and about 35%, between about 10% and about 25%, between about 10% and about 15%, between about 25% and about 75%, between about 25% and about 65%, between about 25% and about 55%, between about 25% and about 45%, between about 25% and about 35%, between about 35% and about 75%, between about 35% and about 65%, between about 35% and about 55%, between about 35% and about 45%, between about 45% and about 75%, between about 45% and about 65%, between about 45% and about 55%, between about 55% and about 75%, or between about 65% and about 75% by weight. In some embodiments, the spray dry formulation contains about 25% of the compound by weight. In some embodiments, the spray dry formulation contains about 30% of the compound by weight. In some embodiments, the spray dry formulation contains about 50% of the compound by weight. In some embodiments, the spray dry dispersion contains at least about 20% of the compound by weight.

In some embodiments, the spray-dried dispersions (SDDs) are incorporated into a final dosage form. Examples of final dosage forms include, but are not limited to, capsules, tablets, and sachets.

As used herein, "treat", "treatment", or "treating" is an approach for obtaining beneficial or desired results including clinical results. For purposes of the compositions and methods provided herein, beneficial or desired clinical results include, but are not limited to, one or more of the following: decreasing one or more symptoms resulting from the condition, diminishing the extent of the condition, stabilizing the condition (e.g., preventing or delaying the worsening of the condition), ameliorating a disease state, providing a remission (whether partial or total) of a disease, decreasing the dose of one or more other medications required to treat the condition, enhancing the effect of another medication used to treat the condition, increasing the quality of life of an individual having the condition, and/or prolonging survival. A method of treating a disease or condition encompasses a reduction of the pathological consequence of the disease or condition. The methods described herein contemplate any one or more of these aspects of treatment.

As used herein, the term "prevent," "preventing" or "prevention" of a condition, disease, or disorder refers in one embodiment, to delay or avoidance of onset of the disease or disorder (i.e., slowing or preventing the onset of the disease or disorder in a patient susceptible to development of the disease or disorder). In some embodiments, "prevent," "preventing" or "prevention" refers in to delaying or slowing the progression of the condition, disease, or disorder.

The term "subject" refers to a mammalian patient in need of such treatment, such as a human.

Exemplary diseases that may be therapeutic targets for such compounds include, but are not limited to, central neurodegenerative disorders such as Alzheimer's Disease, Parkinson's Disease, Huntington Disease and other central neurodegenerative disorders and peripheral degenerative disorders where there is evidence of accumulated neurotoxic proteins.

In one aspect, the compounds and pharmaceutical compositions of the present disclosure specifically target the accumulation of neurotoxic proteins or their aggregated species. Thus, these compounds and pharmaceutical compositions can treat degenerative neurological diseases related to or caused by mis-regulation of protein homeostasis (proteostasis) e.g., such as inadequate clearance of protein aggregates and/or damaged organelles, insufficient activation of a survival pattern of gene expression, and/or deficiencies in cell energetics. In some embodiments, the methods of the present disclosure target neurodegenerative diseases associated with the accumulation of neurotoxic misfolded and aggregated proteins. In some embodiments, methods of treatment target Parkinson's disease, Alzheimer's disease, Lewy body disease, multiple system atrophy, or Huntington's disease. The compounds, compositions, and methods of the present disclosure are also used to mitigate deleterious effects of impaired protein homeostasis including impairments of various forms of macro autophagy and other protein clearance mechanisms. While the present disclosure is not limited by any particular mechanism of action, dysregulation of autophagy is thought to be caused by alpha synuclein beta amyloid and other proteins that accumulate and aggregate in neurodegenerative disorders.

In treatment methods according to the embodiments, an "effective amount" means an amount or dose sufficient to generally bring about the desired therapeutic benefit in subjects needing such treatment. Effective amounts or doses of the compounds provided herein may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 µg to 2 mg of active agent per kilogram of subject's body weight per day, such as about 0.05 to 100 mg/kg/day, or about 1 to 35 mg/kg/day, or about 0.1 to 10 mg/kg/day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The compounds described herein may be used in pharmaceutical compositions or methods in combination with one or more additional active ingredients in the treatment of neurodegenerative disorders. For example, additional active ingredients are those that are known or discovered to be effective in treating neurodegenerative disorders, including those active against another target associated with the disease, such as but not limited to, a) compounds that address protein misfolding (such as drugs which reduce the production of these proteins, which increase their clearance or which alter their aggregation and/or propagation); b) compounds that treat symptoms of such disorders (e.g., dopamine replacement therapies, cholinesterase inhibitors and precognitive glutamatergic drugs); and c) drugs that act as neuroprotectants by complementary mechanisms (e.g., those targeting autophagy, those that are anti-oxidants, and those acting by other mechanisms such as adenosine A2A antagonists).

For example, additional active ingredients are those that are known or discovered to be effective in treating neurodegenerative disorders, including those active against another target associated with the disease, such as but not limited to, a) compounds that target different mechanisms of protein misfolding (such as aggregation and/or propagation); b) compounds that treat symptoms of such disorders (e.g., dopamine replacement therapies); and c) drugs that act as neuroprotectants by complementary mechanisms (e.g., those targeting autophagy, anti-oxidants, and adenosine A2A antagonists).

For example, compositions and formulations provided herein, as well as methods of treatment, can further comprise other drugs or pharmaceuticals, e.g., other active agents useful for treating or palliative for a degenerative neurological disease related to or caused by protein aggregation, e.g., synuclein, beta-amyloid, tau, Huntingtin, or TDP43 protein aggregation, e.g., Parkinson's disease, Alzheimer's Disease (AD), Lewy body disease (LBD) and multiple system atrophy (MSA), or related symptoms or conditions. In this regard, compositions and formulations of the generic and specific compounds described herein are useful in methods of treatment for Alzheimer's Disease, Parkinson's Disease, fronto-temporal dementia, dementia with Lewy Bodies, PD dementia, multiple system atrophy, Huntington's disease, Amyotrophic lateral sclerosis, cancer, infection, Crohn's disease, heart disease, aging, or traumatic brain injury (TBI). The pharmaceutical compositions provided herein may additionally comprise one or more of such active agents, and methods of treatment may additionally comprise administering an effective amount of one or more of such active agents. In some embodiments, the one or more additional active agents is a compound that is used to treat the symptoms or progression of a neurodegenerative disorder (e.g., Alzheimer's Disease, Parkinson's Disease, Huntington's disease). In certain embodiments, additional active agents may be cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof. In some embodiments, the additional active agent is an anti-inflammatory agent. Additional active agents include those useful in such compositions and methods include dopamine therapy drugs, catechol-O-methyl transferase (COMT) inhibitors, monoamine oxidase inhibitors, cognition enhancers (such as acetylcholinesterase inhibitors or memantine), adenosine 2A receptor antagonists, beta-secretase inhibitors, or gamma-secretase inhibitors. In particular embodiments, at least one compound of the present embodiments may be combined in a pharmaceutical composition or a method of treatment with one or more drugs selected from the group consisting of tacrine (Cognex), donepezil (Aricept), rivastigmine (Exelon) galantamine (Reminyl), physostigmine, neostigmine, Icopezil (CP-118954, 5,7-dihydro-3-[2-[1-(phenylmethyl)-4-piperidinyl]ethyl]-6H-pyrrolo-[4,5-f-]-1,2-benzisoxazol-6-one maleate), ER-127528 (4-[(5,6-dimethoxy-2-fluoro-1-indanon)-2-yl]methyl-1-(3-fluorobenzyl)piperidine hydrochloride), zanapezil (TAK-147; 3-[1-(phenylmethyl)piperidin-4-yl]-1-(2,3,4,5-tetrahydro-1H-1-benzazepin-8-yl)-1-propane fumarate), Metrifonate (T-588; (−)-R-alpha-[[2-(dimethylamino)ethoxy]methyl] benzo[b]thiophene-5-methanol hydrochloride), FK-960 (N-(4-acetyl-1-piperazinyl)-p-fluorobenzamide-hydrate), TCH-346 (N-methyl-N-2-pyropinyldibenz[b,f]oxepine-10-methanamine), SDZ-220-581 ((S)-alpha-amino-5-(phosphonomethyl)-[1,1'-biphenyl]-3-propionic acid), memantine (Namenda/Exiba) and 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethylphenyl)-1,2,3,6-tetrahydropyr-idine, Huperzine A, posatirelin, leuprolide or derivatives thereof, ispronicline, (3-aminopropyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lomoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and Minozac (2-(4-(4-methyl-6-phenylpyridazin-3-yl)piperazin-1-yl)pyrimidine dihydrochloride hydrate). Such a combination may serve to increase efficacy, ameliorate other disease symptoms, decrease one or more side effects, or decrease the required dose of the compounds or compositions described herein. The additional active ingredients may be administered in a separate pharmaceutical composition from a compound provided herein or may be included with a compound provided herein in a single pharmaceutical composition. The additional active ingredients may be administered simultaneously with, prior to, or after administration of a compound of Formula (I).

Methods of Treatment

Provided herein are methods of treating a condition associated with neurodegeneration or aggregation/accumulation of proteins, which include administering to a subject in need of such treatment an effective amount of a compound or composition described herein. Any of the compounds or pharmaceutical compositions provided herein may be used in the treatment of a condition associated with neurodegeneration or aggregation/accumulation of proteins. In some embodiments, the protein is alpha synuclein, a-beta, tau, Huntingtin, or TDP43. In some embodiments, the condition is Alzheimer's Disease, Parkinson's Disease, fronto-temporal dementia, dementia with Lewy Bodies, PD dementia, multiple system atrophy, Huntington's disease, Amyotrophic lateral sclerosis, progressive supranuclear palsy, cancer, infection, Crohn's disease, heart disease, aging, or traumatic brain injury (TBI).

Also provided herein is the use of at least one compound or composition described herein in the manufacture of a medicament for treatment of a condition associated with neurodegeneration or aggregation/accumulation of proteins. In some embodiments, the condition is a neurodegenerative disease or condition. In some embodiments, the condition is Alzheimer's Disease, Parkinson's Disease, fronto-temporal dementia, dementia with Lewy Bodies, PD dementia, multiple system atrophy, Huntington's disease, Amyotrophic lateral sclerosis, progressive supranuclear palsy, cancer, infection, Crohn's disease, heart disease, aging, or traumatic brain injury (TBI).

Also provided are methods of preventing aggregation or accumulation or enhancing clearance of protease-resistant protein, which include contacting the protease-resistant protein with an effective amount of at least one compound or composition described herein. In some embodiments, the contacting is in vitro or ex vivo. In some embodiments, the contacting is in vivo.

Also provided are methods of decreasing neuroinflammation in a subject. In some embodiments, the present disclosure provides a method of decreasing neuroinflammation in a subject, comprising administering to the subject an effective amount of a compound or composition described herein. In some embodiments, provided are methods of treating a disease or condition associated with neuroinflammation, comprising administering to the subject an effective amount of a compound or composition described herein. In some embodiments, provided herein is the use of at least one compound or composition described herein in the manufacture of a medicament for decreasing neuroinflammation in a subject. In other embodiments, provided herein is the use of at least one compound or composition described herein in the manufacture of a medicament for the treatment of a disease or condition associated with neuroinflammation.

In one aspect, provided herein are kits containing a compound or composition described herein and instructions for use. The kits may contain instructions for use in the treatment of a condition in an individual in need thereof. In some embodiments, the condition is a neurodegenerative disease or condition. In some embodiments, the condition is Alzheimer's Disease, Parkinson's Disease, fronto-temporal dementia, dementia with Lewy Bodies, PD dementia, multiple system atrophy, Huntington's disease, Amyotrophic lateral sclerosis, progressive supranuclear palsy, cancer, infection, Crohn's disease, heart disease, aging, or traumatic brain injury (TBI). A kit may additionally contain any materials or equipment that may be used in the administration of the compound or composition, such as vials, syringes, or IV bags. A kit may also contain sterile packaging.

Chemical Synthesis

The embodiments are also directed to processes and intermediates useful for preparing subject compounds or a salt or solvate thereof.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," $4^{th}$ ed., Wiley, New York 2006. The protecting groups may be removed at a convenient subsequent stage using methods known from the art.

Exemplary chemical entities useful in methods provided herein will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is run at a temperature from about 0° C. to the reflux temperature of the organic solvent used. Unless otherwise specified, the variables are as defined above in reference to Formula (I). Isotopically labeled compounds as described herein are prepared according to the methods described below, using suitably labeled starting materials. Such materials are generally available from commercial suppliers of radiolabeled chemical reagents.

Representative syntheses for compounds of Formula (I) are described in Schemes 1 and 2.

Scheme 1
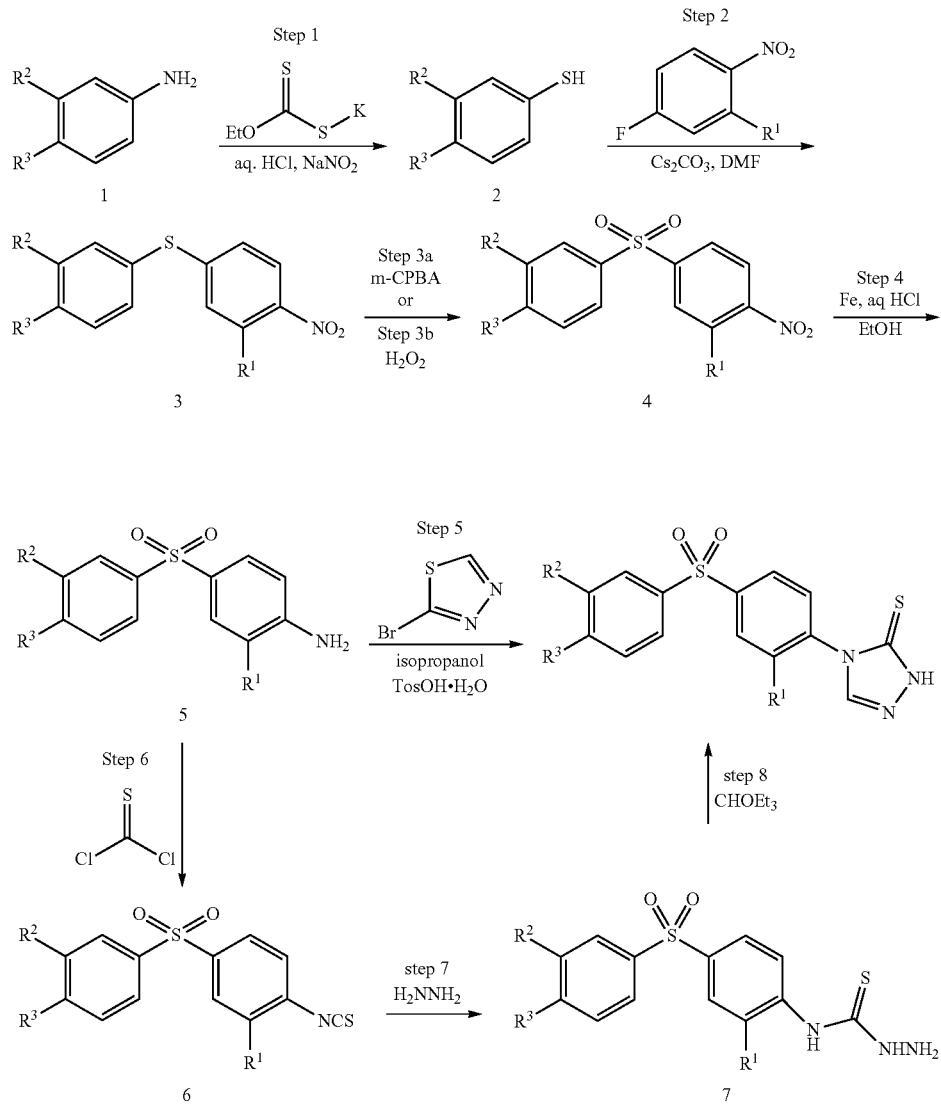
Scheme 2
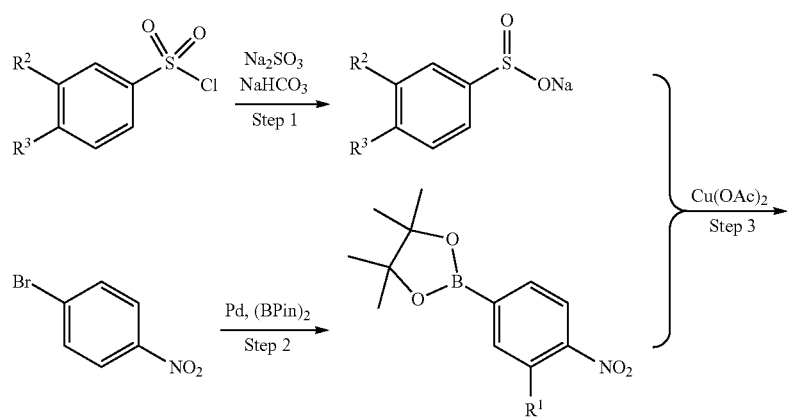

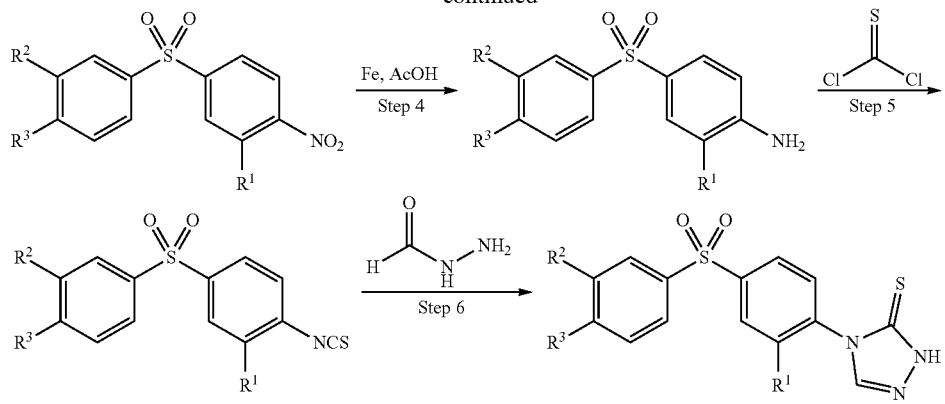

In Schemes 1 and 2, $R^1$, $R^2$, and $R^3$ are as defined herein. Starting materials may be obtained from commercial sources or via well-established synthetic procedures.

Scheme 3 shows the general synthesis for compounds of an embodiment of Formula (I).

Scheme 3

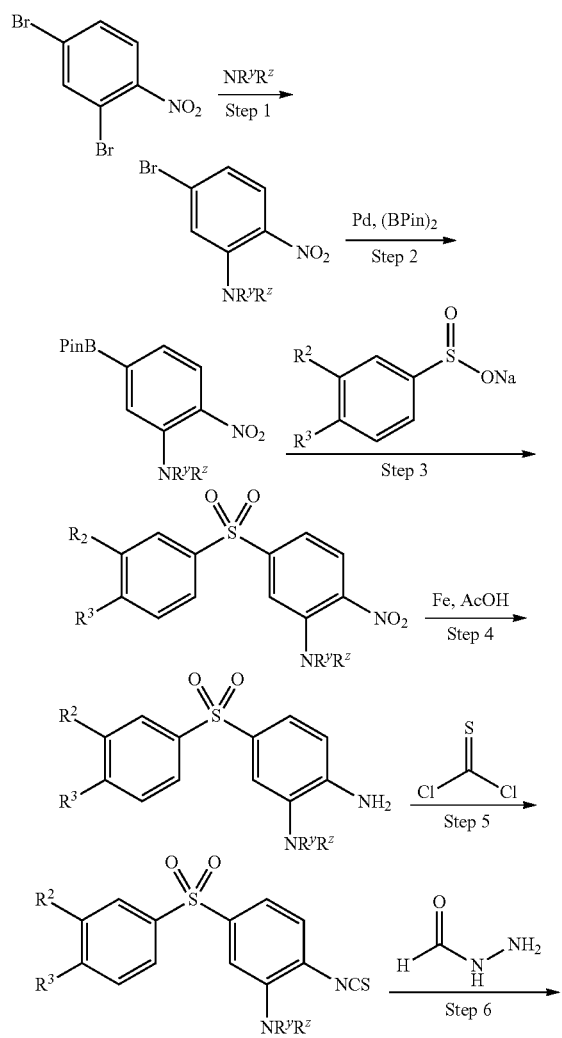

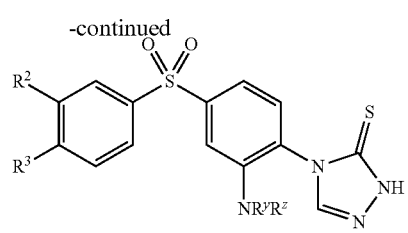

In Scheme 3, $R^1$, $R^2$, $R^3$, $R^y$, and $R^z$ are as defined herein.

In certain instances, the above processes further involving the step of forming a salt of a compound of the present disclosure. Embodiments are directed to the other processes described herein; and to the product prepared by any of the processes described herein.

EXAMPLES

The following examples are offered to illustrate but not to limit the present disclosure. The compounds are prepared using the general methods described above.

The following chemical abbreviations are used throughout the Examples: ACN (acetonitrile), (BPin)$_2$ (bis(pinacolato)diboron), DCM (dichloromethane), DMF (dimethylformamide), DMSO (dimethyl sulfoxide), EDTA (ethylenediaminetetraacetic acid), EtOH (ethanol), HPLC (high-performance liquid chromatography), IPA (isopropyl alcohol), IPAc (isopropyl acetate), LCMS (liquid chromatography-mass spectrometry), mCPBA (meta-chloroperoxybenzoic acid), MeOH (methanol), MTBE (methyl terbutyl ether), THF (tetrahydrofuran), 2-MeTHF (2-methyltetrahydrofuran), and p-TSA or TsOH (p-toluenesulfonic acid).

Example 1: 4-(4-((4-chloro-3-(trifluoromethyl)phenyl)sulfonyl)phenyl)-2,4-dihydro-3H-1,2,4-triazole-3-thione (Compound 1)

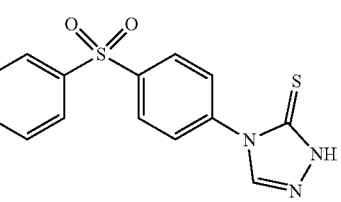

(i.) Synthesis Route A

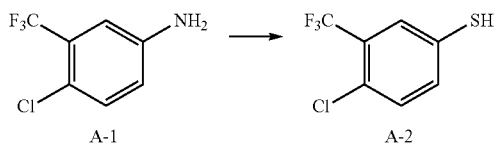

Step 1: To a mixture of 4-chloro-3-(trifluoromethyl)aniline (500 g, 2.56 mol) in HCl (750 mL) and H$_2$O (750 mL) was added a solution of NaNO$_2$ (194 g, 2.81 mol) in 250 mL water, dropwise while keeping the temperature below 5° C. The mixture was stirred at 0-5° C. for 30 min. A solution of ethoxycarbothioyl-sulfanyl potassium (492 g, 3.07 mol) in 1 L water was added dropwise at 0-5° C., and the mixture was stirred at 20° C. for 12 hrs. The mixture was extracted with ethyl acetate (1 L, 3 times). The organic layers were washed with brine (1 L), dried over Na$_2$SO$_4$, and evaporated to give o-ethyl [4-chloro-3 (trifluoromethyl)phenyl]-sulfanylmethanethioate (600 g, crude) as a brown oil, which was used directly in the next step.

To the mixture of o-ethyl [4-chloro-3-(trifluoromethyl)phenyl]-sulfanylmethanethioate (600 g, 2 mol) in EtOH (2 L) and H$_2$O (200 mL) was added KOH (470 g, 8.38 mol). The mixture was stirred at 80° C. for 12 hrs. LCMS showed the desired compound. EtOH was evaporated to give a brown residue which was dissolved in H$_2$O (2 L) and extracted with 1:1 MTBE/petroleum ether (1 L, 3 times). The aqueous layer was adjusted to pH=1 with concentrated HCl and extracted with ethyl acetate (1 L, 2 times). The organic layers were washed with brine (1 L), dried over Na$_2$SO$_4$, and evaporated to give 4-chloro-3-(trifluoromethyl)benzenethiol (480 g, crude) as a brown oil.

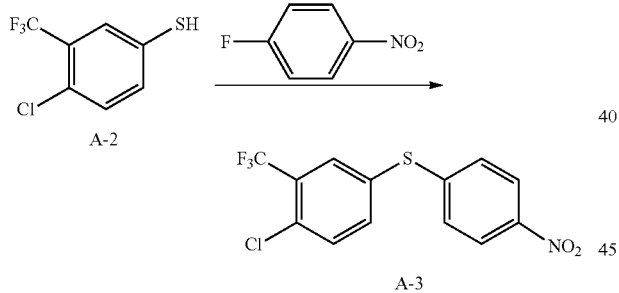

Step 2: To the mixture of 4-chloro-3-(trifluoromethyl)benzenethiol (480 g, 2.26 mol) in DMF (3 L) was added Cs$_2$CO$_3$ (1.15 kg, 3.53 mol) and 1-fluoro-4-nitro-benzene (300 g, 2.12 mol). The mixture was stirred at 80° C. for 3 hrs. The mixture was filtered and the solvent was added to 3 L water and extracted with ethyl acetate (1 L×3). The organic layer was washed with 2 L brine, dried over Na$_2$SO$_4$, and evaporated to give (4-chloro-3-(trifluoromethyl)phenyl)(4-nitrophenyl)sulfane (640 g, crude) as a brown solid. $^1$H NMR: (CDCl$_3$, 400 MHz) δ 8.13-8.16 (m, 2H), 7.83 (d, J 0.8 Hz, 1H), 7.58-7.60 (m, 2H), 7.27-7.29 (m, 2H).

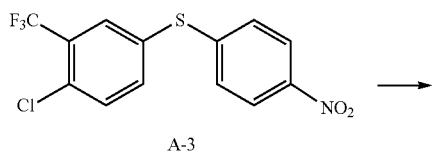

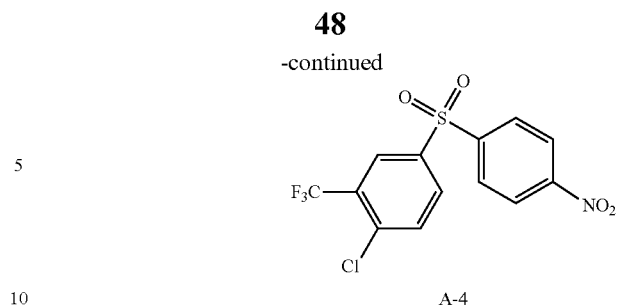

Step 3a: To the mixture of A-3 (640 g, 1.93 mol) in DCM (3.5 L) was added mCPBA (822 g, 4.05 mol, 80% purity) at 20° C. The mixture was stirred at 20° C. for 12 hrs. The mixture was added to a solution of Na$_2$SO$_3$ (100 g, 0.79 mol) and Na$_2$CO$_3$ (250 g, 2.36 mol) in 4 L H$_2$O, and stirred at 20° C. for 2 hrs. The mixture was filtered, and the solid was collected as the desired compound. Additionally, the aqueous layer was extracted with DCM (2 L×2), and the combined organic layers were evaporated to give a brown solid which was made a slurry with ethyl acetate (2 L) to give A-4 (475 g, 67% yield) as a white solid. $^1$H NMR (DMSO, 400 MHz) δ 8.33-8.42 (m, 6H), 8.03-8.05 (m, 1H).

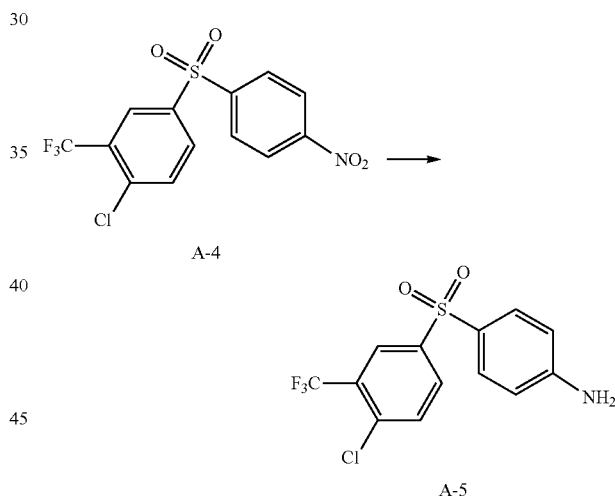

Step 4: To the mixture of A-4 (450 g, 1.23 mol) in EtOH (1.25 L) and H$_2$O (1.25 L) was added HCl (15 mL). The mixture was heated to 70° C. Fe (140 g, 2.46 mol) was added, and the mixture was stirred at 70° C. for 3 hrs. The mixture was filtered, and EtOH was evaporated. The remaining aqueous solution was extracted with DCM (0.5 L×3), and the organic layers were evaporated to give a solid (the crude product). The solid was dissolved in DCM (1 L×3) and filtered. The solvent was evaporated to give the desired compound. The combined A-5 (200 g, 48% yield) was obtained as an earth yellow solid. $^1$H NMR (CDCl$_3$, 400 MHz): δ 8.20 (s, 1H), 7.98 (d, J=7.2 Hz, 1H), 7.70 (d, J=8.8 Hz, 2H), 7.61 (d, J=8.4 Hz, H) 6.68 (d, J=8.4 Hz, 2H), 4.27 (s, 2H).

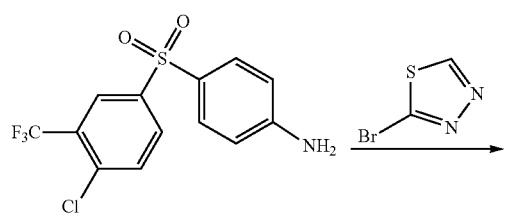

A-5

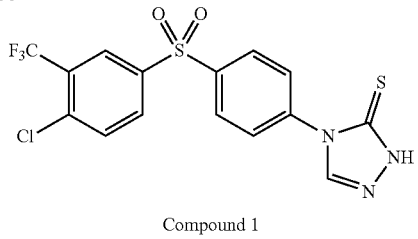

Compound 1

Step 5: To the mixture of A-5 (100 g, 298 mmol) in isopropanol (1.20 L) was added 2-bromo-1,3,4-thiadiazole (49.2 g, 298 mmol) and TsOH.H$_2$O (8.50 g, 44.7 mmol). The mixture was stirred at 80° C. for 4 hrs. The mixture was filtered, and the filtrate was evaporated to give a crude product. The crude product was purified by column chromatography on silica gel (petroleum ether/ethyl acetate=3/1~0/1, 0-10% 0.5M NH$_3$.H$_2$O/MeOH in DCM) to give a yellow solid which was made a slurry from MeOH (300 mL), MTBE (500 mL), and H$_2$O (500 mL), then dried in vacuum to give Compound 1 (20 g, 8% yield) as a white solid. 1H NMR (500 MHz, DMSO-d6) δ 14.07 (s, 1H), 8.77 (s, 1H), 8.42-8.32 (m, 2H), 8.32-8.25 (m, 2H), 8.03 (dd, J=8.8, 2.3 Hz, 3H). LCMS ES+(m/z), 420.0 (M+1)+, Cl pattern found.

(ii.) Synthesis Route B

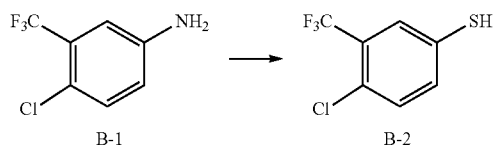

B-1         B-2

Step 1: In a 1 L round-bottom flask equipped with a mechanical stirrer and thermometer was added 60 mL of concentrated hydrochloric acid, 60 mL of water, and 4-chloro-3-(trifluoromethyl)benzene amine (19.5 g, 0.1 mol). The mixture was heated to promote dissolution and then cooled down to below 0° C. in an ice-water bath. A solution of sodium nitrite (7.6 g, 0.11 mol) in 10 mL of water was added in dropwise while the internal temperature was kept below 5° C., and the mixture was stirred at 5° C. for 30 min. The mixture was then added into a mixture of potassium ethyl xanthate (19.2 g, 0.12 mol) in 30 mL of water over 2 hours. Upon the completion of reaction (about 30 min), the organic phase in the reaction mixture was separated, and the aqueous layer was extracted twice with diethyl ether. The combined organic layers were washed with 30 mL of 10% sodium hydroxide solution followed by several portions of water until the aqueous phase that separated was pH neutral. The organic phase was dried over Na$_2$SO$_4$ and concentrated, and the crude residue was dissolved in 95% ethanol (100 mL). The solution heated to reflux to aid dissolution. To this hot solution was added potassium hydroxide pellets (23.5 g, 0.42 mol) slowly so that the solution kept gentle refluxing until all the material was completely dissolved in water (about 8 hours). Approximately 80 mL of ethanol was then removed by distillation on a steam bath, and the residue was taken up in the minimum amount of water (about 100 mL). The aqueous solution was extracted with diethyl ether (50 mL×3). The pH of aqueous layer was adjusted to 1 with 6 N sulfuric acid. Extraction with diethyl ether (50 mL×3) was performed, and the combined organic layers were dried over Na$_2$SO$_4$ and concentrated to give the crude product, which was purified by column chromatography (0 to 2% ethyl acetate/petroleum ether) to give 4-chloro-3-(trifluoromethyl)benzenethiol (16.1 g, 75%) as a yellow solid.

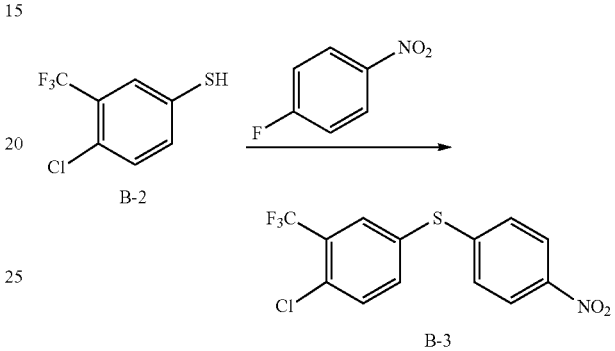

Step 2: To a solution of 4-chloro-3-(trifluoromethyl)benzenethiol (19.2 g, 0.091 mol) in N,N-dimethylformamide (250 mL) was added 1-fluoro-4-nitrobenzene (12.8 g, 0.091 mol) and Cs$_2$CO$_3$ (59.4 g, 0.182 mol), and the reaction mixture was stirred at 80° C. under thin layer chromatography monitoring (1:30 ethyl acetate/petroleum ether). Upon the completion of the reaction, the mixture was cooled to room temperature and diluted with water (500 mL). The aqueous layer was extracted with ethyl acetate (200 mL×3), and the combined organic layers were washed with brine, dried over Na$_2$SO$_4$, filtered and concentrated to give crude 4-chloro-3-(trifluoromethyl)phenyl)(4-nitrophenyl)sulfane (25 g, 82%) as a yellow oil, which was used in the next step without further purification.

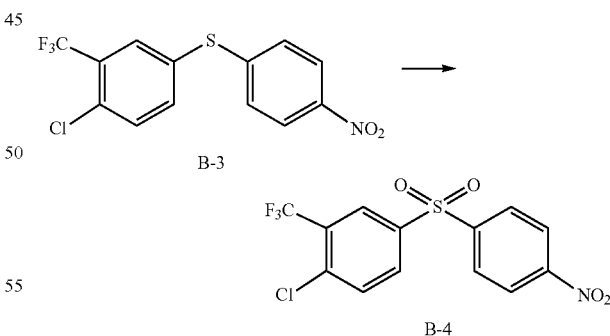

Step 3b: To a solution of 4-chloro-3-(trifluoromethyl) phenyl)(4-nitrophenyl)sulfane (25 g, 0.075 mol) in acetic acid (100 mL) was added 30% H$_2$O$_2$ dropwise (20 g, 0.3 mol) at room temperature. The reaction mixture was stirred at 85° C. with thin layer chromatography monitoring (1:5 ethyl acetate/petroleum ether). Upon the completion of reaction, water was added to quench the reaction. The aqueous layer was extracted with ethyl acetate (100 mL×3), and the combined organic layers were washed with brine, dried over Na$_2$SO$_4$, filtered and concentrated to give the crude product, which was purified by flash chromatography (0 to 10% ethyl acetate/petroleum ether) to give 1-chloro-4-(4-nitrophenylsulfonyl)-2-(trifluoromethyl) benzene (20.8 g, 76%) as a white solid.

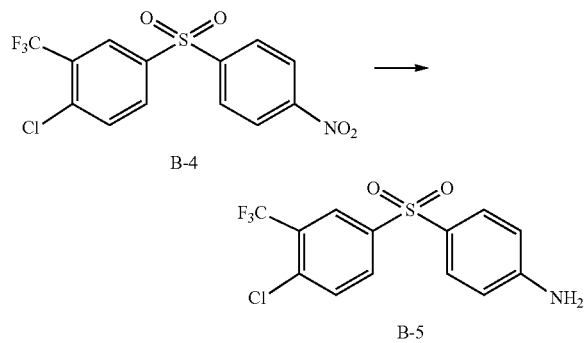

B-4

B-5

Step 4: Five drops of concentrated HCl was added into a mixture of iron power (16 g, 0.29 mol) in water (100 mL) and ethanol (100 mL). The mixture was heated to reflux while 1-chloro-4-(4-nitrophenylsulfonyl)-2-(trifluoromethyl)benzene (26.4 g, 0.072 mol) was added. The reaction mixture was kept under reflux for an additional hour with thin layer chromatography monitoring (1:5 ethyl acetate/petroleum ether). Upon the completion of reaction, the hot mixture was filtered, and the filter cake was washed with ethanol. The pH of filtrate was adjusted to 10 with 2 N NaOH, and the aqueous phase was extracted with ethyl acetate (100 mL×3). The combined organic layers were washed with brine, dried over Na$_2$SO$_4$, filtered and concentrated to give the crude product, which was purified by flash chromatography (0 to 15% ethyl acetate/petroleum ether) to give 4-((4-chloro-3-(trifluoromethyl)phenyl)sulfonyl) aniline as a white solid (19.4 g, 79%).

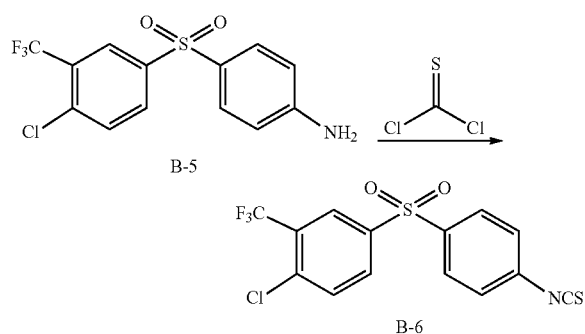

B-5

B-6

Step 6: Thiophosgene (6.6 g, 0.057 mol) was added into a two phase solution of 4-((4-chloro-3-(trifluoromethyl) phenyl)sulfonyl) aniline (19.2 g, 0.057 mol) in dichloromethane and water containing sodium bicarbonate (13.4 g, 0.13 mol) at 0° C. The reaction mixture was stirred at 0° C. for 2 hours. Upon the completion of reaction, the organic layer was separated, dried over Na$_2$SO$_4$, filtered and concentrated to dryness. The residue was purified by column chromatography (0 to 50% ethyl acetate/petroleum ether) to give 1-chloro-4-(4-isothiocyanatophenylsulfonyl)-2-(trifluoromethyl)benzene (11.5 g, 53%) as a yellow solid.

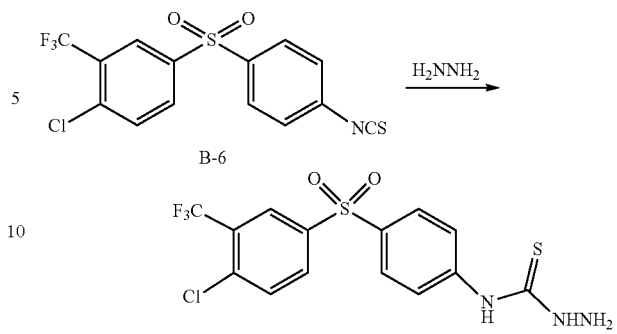

B-6

B-7

Step 7: Hydrazine monohydrate (5.2 g, 0.058 mol) was added into a solution of 1-chloro-4-(4-isothiocyanatophenylsulfonyl)-2-(trifluoromethyl)benzene (11 g, 0.029 mol) in ethanol (60 mL) dropwise at 0° C. After 4 hours, the reaction mixture was diluted with water (100 mL) and extracted with dichloromethane (50 mL×3). The combined organic layers were washed with brine, dried over Na$_2$SO$_4$, filtered and concentrated to give crude N-(4-((4-chloro-3-(trifluoromethyl)phenyl)sulfonyl) phenyl)hydrazinecarbothioamide (8.4 g, 70%), which was used in the next step without further purification.

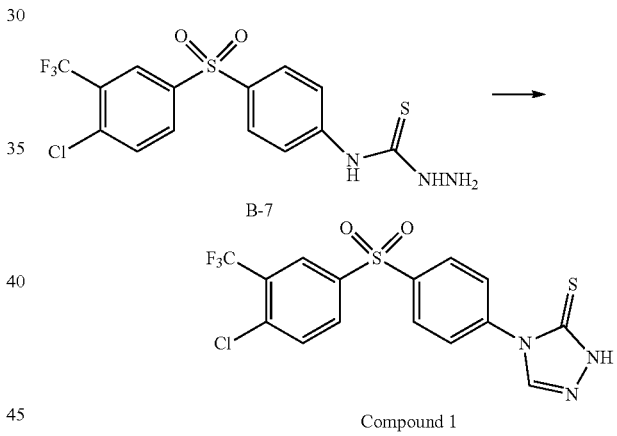

B-7

Compound 1

Figure 1B:
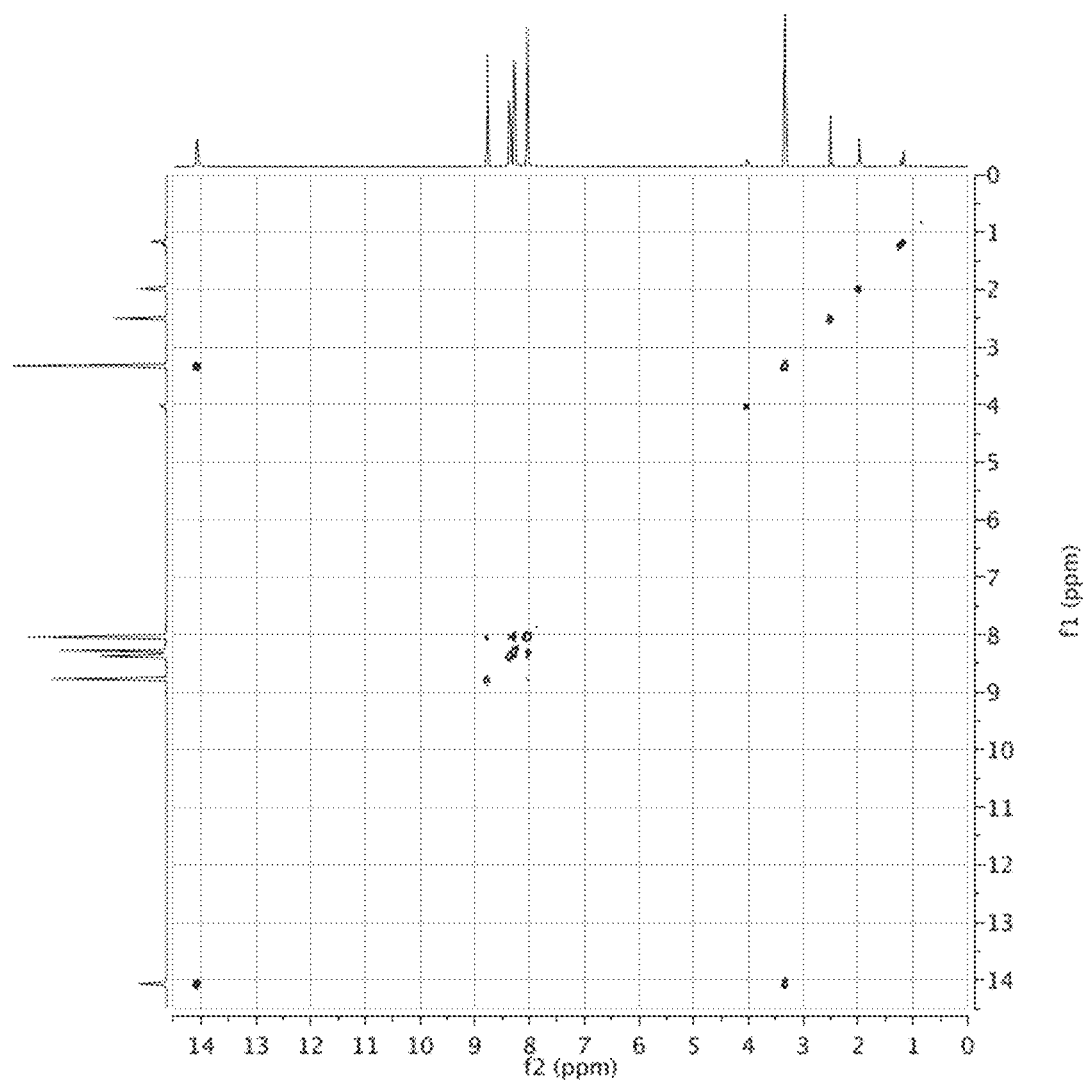
FIG. 1B shows a 2D NOESY spectrum of Compound 1 in DMSO-d6 (400 MHz) as synthesized from Route B.
Figure 1C:
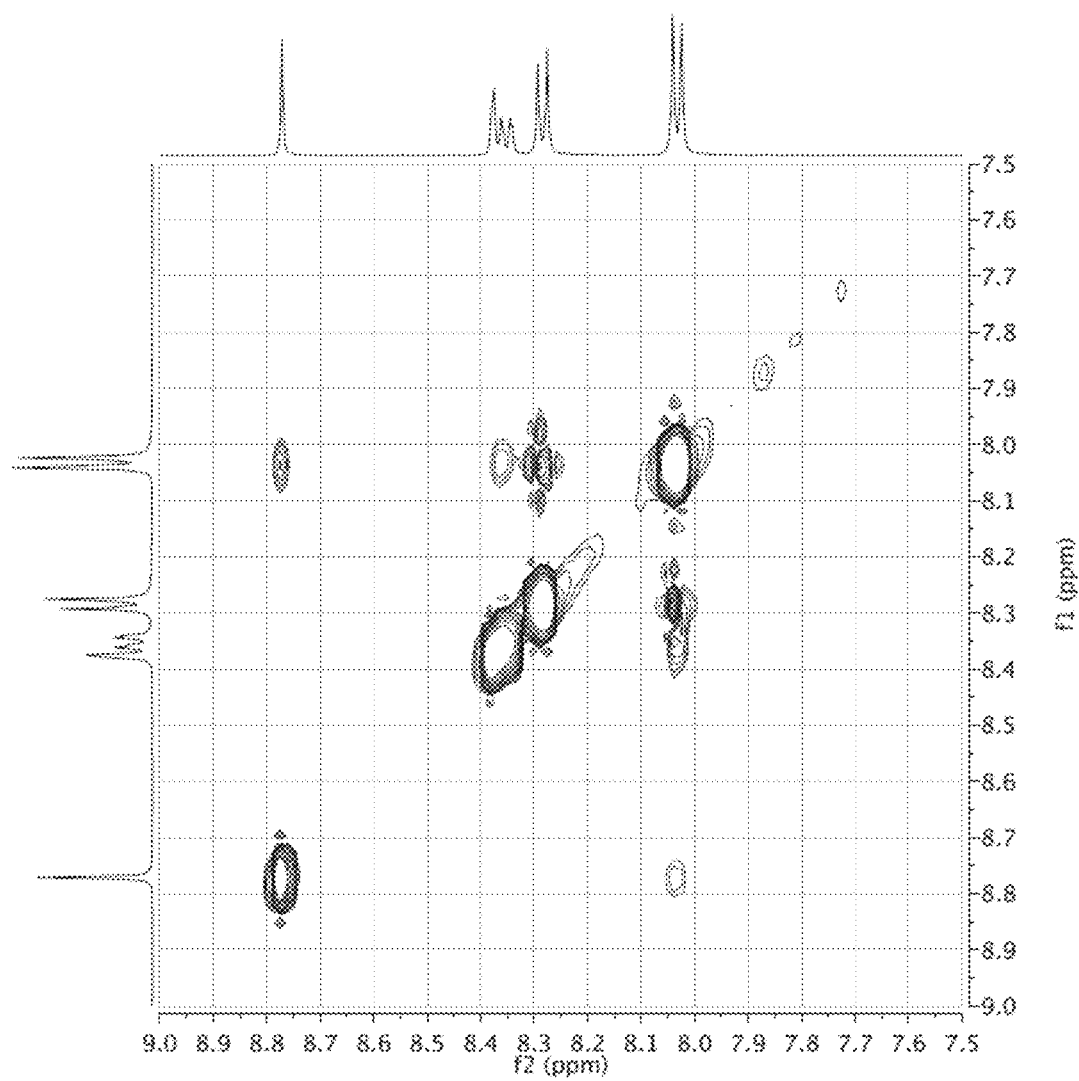
FIG. 1C shows an expansion of the 2D NOESY spectrum of compound 1 in DMSO-d6 (500 mHz) as synthesized from Route B.

Step 8: N-(4-((4-Chloro-3-(trifluoromethyl)phenyl)sulfonyl) phenyl)hydrazinecarbothioamide (8.2 g, 0.02 mol) was treated with triethoxymethane (50 mL) at 145° C. for 3 hours. Water (100 mL) was added, and the mixture was extracted with dichloromethane (50 mL×3). The combined organic layers were washed with brine, dried over Na$_2$SO$_4$, filtered and concentrated to give the crude product, which was purified by column chromatography (0 to 10% ethyl acetate/petroleum ether) to give the title compound (5.4 g, 64%) as a white solid. $^1$H NMR (300 MHz, DMSO-d6) δ 14.07 (s, 1H), 8.77 (s, 1H), 8.41-8.32 (m, 2H), 8.32-8.25 (m, 2H), 8.06-8.00 (m, 3H). LCMS ES+(m/z), 420.0 (M+1)$^+$, Cl pattern found. FIG. 1B shows a 2D NOESY spectrum of Compound 1 in DMSO-d6 (400 MHz) as synthesized via Route B. FIG. 1C shows an expansion of the 2D NOESY spectrum of compound 1 in DMSO-d6 (500 mHz) as synthesized via Route B. The NOESY spectra show nOe coupling between the triazole thione CH and the phenyl CH, corresponding to R$^1$ in Formula 1.

(iii.) Synthesis Route C

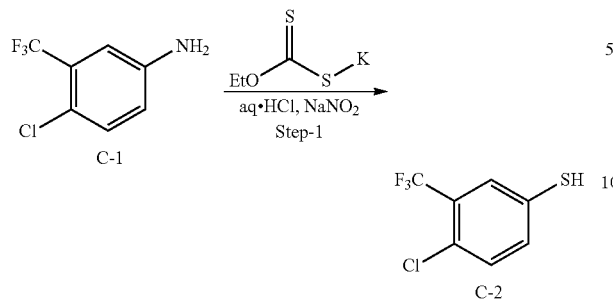

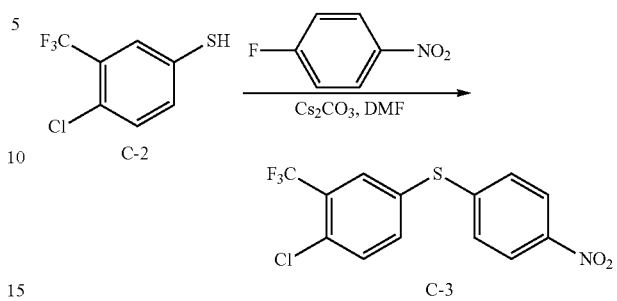

Step 1: A 250 mL jacketed flask was equipped with a magnetic stirrer. The flask was charged with concentrated HCl (25 mL, 0.30 mol, 3.0 eq) and water (98.2 mL). 4-Chloro-3-(trifluoromethyl)aniline (20.0 g, 0.10 mol, 1.0 eq) was melted and added to the flask at 25° C. The mixture was heated to 50° C. and stirred at 50° C. for 30 min. After cooling the mixture to 0-5° C., a solution of NaNO$_2$ (7.6 g, 0.11 mol, 1.1 eq) in 12 mL water was added dropwise over 30 min while maintaining a temperature between 0-5° C. After completing addition of NaNO$_2$, the mixture was stirred at 0-5° C. for 1 h.

A second reaction flask was charged with potassium ethyl xanthate (20.8 g, 0.13 mol, 1.3 eq) followed by water (80 mL). After stirring for 20 minutes, toluene (80 mL) was added followed by dropwise addition of the diazonium salt from the first reaction flask at 19-23° C. over 3 h. After complete addition, the mixture was stirred at 20° C. for 2 h. The aqueous phase was separated from the organic phase and extracted with 20 mL toluene, three times. The organic phases were combined and washed with water (10 mL, 4 times) and then degassed by bubbling nitrogen through for 30 min.

A third flask was charged with EtOH (63.2 g), water (10 mL) and KOH (23.0 g, 0.41 mol, 4.1 eq). The ethanolic KOH solution was degassed by bubbling nitrogen through the mixture 30 minutes. The KOH solution was heated to 75-82° C. under and inert nitrogen atmosphere. The toluene solution from the second reaction vessel was added to the degassed ethanolic KOH solution at 75-82° C. over the course of 2 hours under an inert nitrogen atmosphere. After addition, the mixture was stirred at 78° C. for 3.5 hours.

The mixture was distilled to 1.5-2 V at 45° C. Additional toluene was added (60 mL, N$_2$ purged) to the mixture before distilling again to 1.5-2 V at 45° C. and adding toluene (20 mL, N$_2$ purged). Water (80 mL, N$_2$ purged) was added into the reaction flask and the aqueous phase was separated from the toluene. The aqueous phase was washed with 20 mL toluene 3 times. The aqueous phase was cooled to 10° C. and the pH was adjusted pH<1 with conc. HCl (32.0 mL) at 10-15° C. The mixture was purged with nitrogen for 20 minutes and warmed to 20° C. MTBE (40 mL, N$_2$ purged) was added under nitrogen atmosphere. The organic and aqueous phases were separated. The aqueous phase was extracted with MTBE (40 mL, N$_2$ purged) 3 times. The organic MTBE phases were combine and washed with water (10 mL, N$_2$ purged) 3 times. By HPLC, the assay yield of 4-chloro-3-(trifluoromethyl)benzenethiol was 64.5%. The product was then phase transferred from MTBE to Acetonitrile by distilling at 60° C. under atmospheric pressure. Acetonitrile (50 mL) was added, and the mixture was distilled at 80° C. under atmospheric pressure. Additional acetonitrile (40 mL) was added to give 4-chloro-3-(trifluoromethyl)benzenethiol with no residual MTBE.

Step 2: To a mixture of 60.0 g of 4-chloro-3-(trifluoromethyl)benzenethiol (0.285 mol, 1.0 eq.) in MeCN (1116 mL) was added Cs$_2$CO$_3$ (195.0 g, 0.60 mol, 2.1 eq.) and 1-fluoro-4-nitro-benzene (52.3 g, 0.37 mol, 1.3 eq.). The mixture was stirred at 80° C. for 11 h, cooled to 25-30° C. and filtered. The filter cake was rinsed with acetonitrile (120 mL×2). The acetonitrile solution was concentrated to 60-120 mL under reduced pressure, keeping the temperature below 45° C. Dichloromethane (1116 mL) and 15% NaCl (1600 mL) were added to the solution. The mixture was stirred at 20-30° C. for 30 minutes and the organic layer was separated. The organic layer was washed with 5 wt % NaCl solution 2 more times. The organic layer was concentrated to 480-600 mL under reduced pressure while keeping the temperature below 45° C. Dichloromethane (560 mL) was added to the solution and the organic layer was concentrated again to 480-600 mL to give a solution of (4-chloro-3-(trifluoromethyl)phenyl)(4-nitrophenyl)sulfane in DCM that was used directly in the next step.

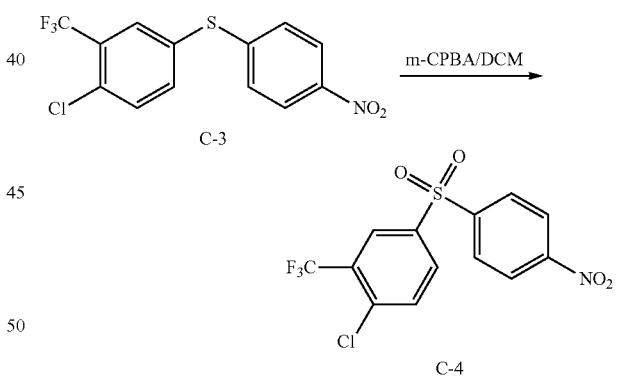

Step 3: Additional DCM (340 mL, 20 vol.) was added to a DCM (8.5 vol.) solution of (4-chloro-3-(trifluoromethyl)phenyl)(4-nitrophenyl)sulfane (17.0 g, 50.9 mmol, 1.0 eq.) from step 2. The mixture was heated to 33-37° C. and stirred for 0.5 h before portion wise addition of m-CPBA (31.0 g, 152.8 mmol, 3.0 eq, 85 wt %) at 33-37° C. The mixture was stirred at 33-37° C. for 4 h and then cooled to 20-30° C. To the mixture, 16% wt Na$_2$SO$_3$ aq. (146.2 g, 8.6×) and 16% Na$_2$CO$_3$ aq. (146.2 g, 8.6×) were added while keeping the temperature below 30° C. The mixture was stirred at 20-30° C. for 1 h. The organic layer was separated, washed with 10 wt % NaCl solution (51.0 g, 3×), and concentrated to 3-5 vol. under reduced pressure below 45° C. IPAc (15 vol.) was added and the solution was concentrated to 6-8 vol. under reduced pressure below 45° C. IPAc (15 vol.) was added to the mixture a second time before again concentrating the solution to 6-8 vol. under reduced pressure below 45° C. IPAc (28 vol.) was added and the mixture was heated to 60° C. with stirring to provide a clear solution. The solution was cooled to 55° C. with stirring for 1-2 h. The solution was distilled to 3-5 vol. under reduced pressure below 55° C. The mixture was cooled down to 45° C. for 2 h. MTBE (11 vol.) was added to the mixture and the mixture stirred at 45° C. for an additional 1-2 h. The mixture was cooled to −10° C. in 11 h and aged at −10° C. for an additional 4.5 h. The mixture was filtered, and the wet cake was washed twice with IPAc/MTBE=1/4 (4 vol.). The wet cake was dried for 1 h under reduced pressure below 45° C. to give 1-chloro-4-((4-nitrophenyl)sulfonyl)-2-(trifluoromethyl)benzene (19.5 g, 99.7% assay yield) as an off-white solid (97.5% purity).

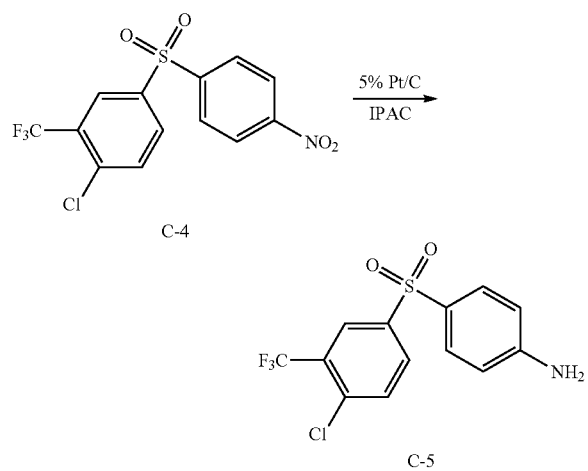

C-4

C-5

Step 4: 1-Chloro-4-((4-nitrophenyl)sulfonyl)-2-(trifluoromethyl)benzene (20.0 g, 54.7 mmol) and IPAc (200 mL) were added to a 1.0 L high-pressure vessel. The vessel was purged and degassed with Ar₂, charged with 5% Pt/C (800 mg) under N₂ protection, purged and degassed with H₂ and the mixture was stirred at 0.5 MPa (72.5 psi) H₂ atmosphere at 65° C. for 18 h. Over that period the hydrogen pressure was depleted to 0 MPa, so the vessel was recharged with H₂ to 0.5 MPa and kept at 65° C. for 14 h. The mixture was cooled, filtered through celite, washed with IPAc (50 mL×2) and the solvent was distilled to obtain a light yellow solid (18.0 g, 98.5% crude yield).

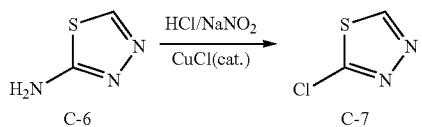

C-6

C-7

Step 5: To a flask containing 1,3,4-thiadiazol-2-amine (5.0 g, 49.4 mmol) at 30° C. was added 30 mL of HCl (30 g, 36.5% aq, 300 mmol) followed by 25 mL of H₂O. The solution was cooled to 0° C. to give a suspension. CuCl (0.5 g, 4.9 mmol) was added at 0° C. A solution of NaNO₂ (3.4 g, 49.4 mmol) in H₂O (50 mL) was added slowly at 0° C. over a period of 30 min. and the reaction mixture was stirred for 2.5 h at 0-5° C. IPAc (100 mL) was added and the reaction was quenched with 10% NaHSO₃ (60 mL). NaHCO₃ (25 g, solid) was added slowly to pH=6-7 and the organic layer was separated. The aqueous layer was extracted with IPAc (100 mL×2). The organic layers were combined and washed with 10% EDTA (50 mL×4) and H₂O (100 mL). The combined EDTA aqueous and H₂O layers were extracted with IPAc (100 mL). The combined organic IPAc extracts were dried over Na₂SO₄, filtered, concentrated in vacuo, redissolved in IPAc (100 mL) and evaporated in vacuo (2×) to give crude product (4.0 g) as an light yellow oil. The oil was stored at 5° C. for up to 12 h.

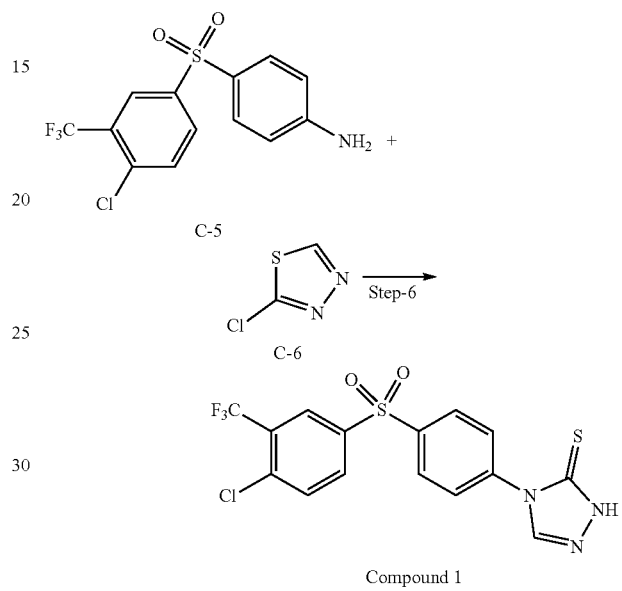

Compound 1

Figure 1D:
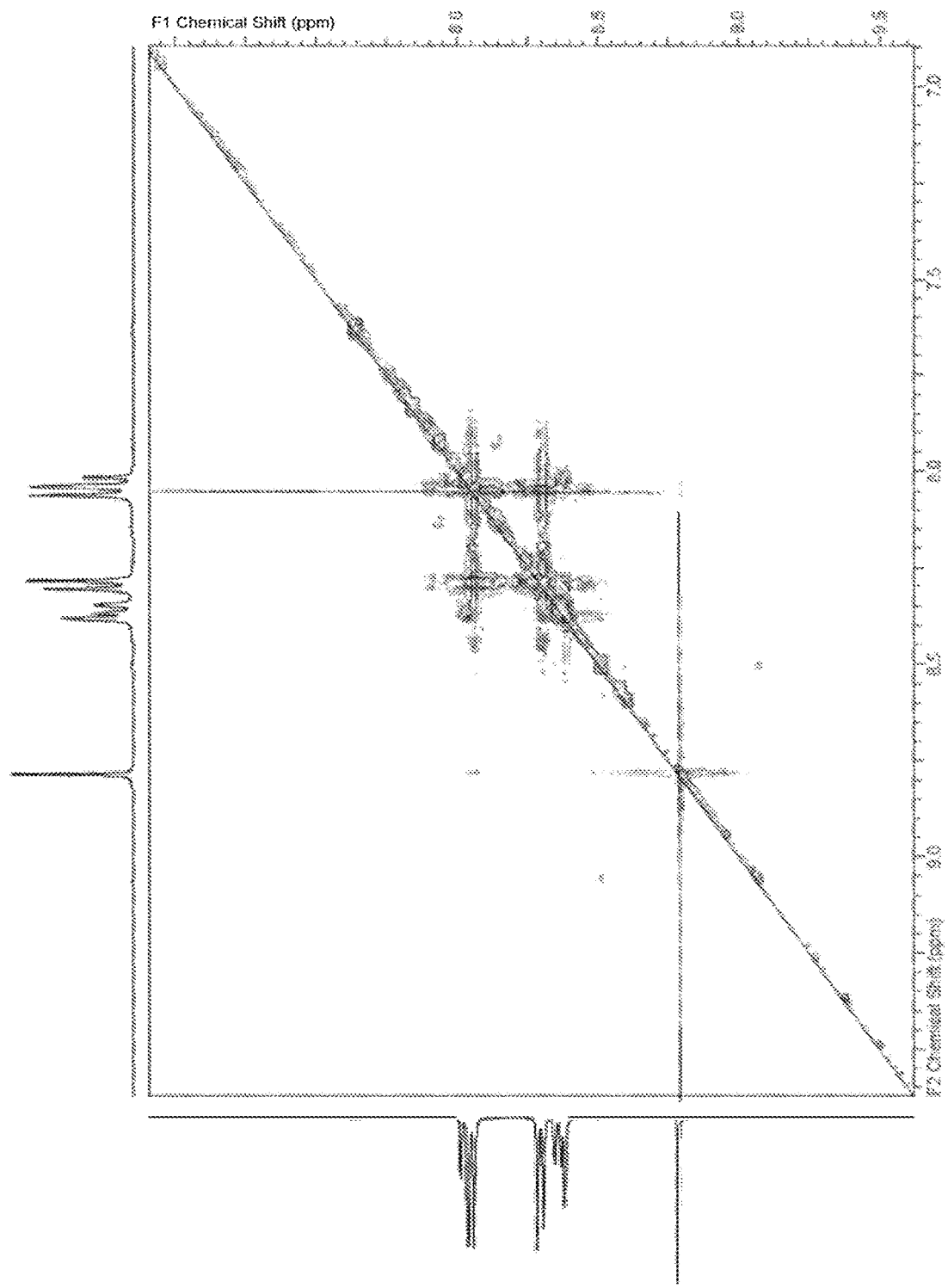
FIG. 1D shows a 2D NOESY spectrum of Compound 1 in DMSO-d6 (400 MHz) as synthesized from Route C.
Figure 1E:
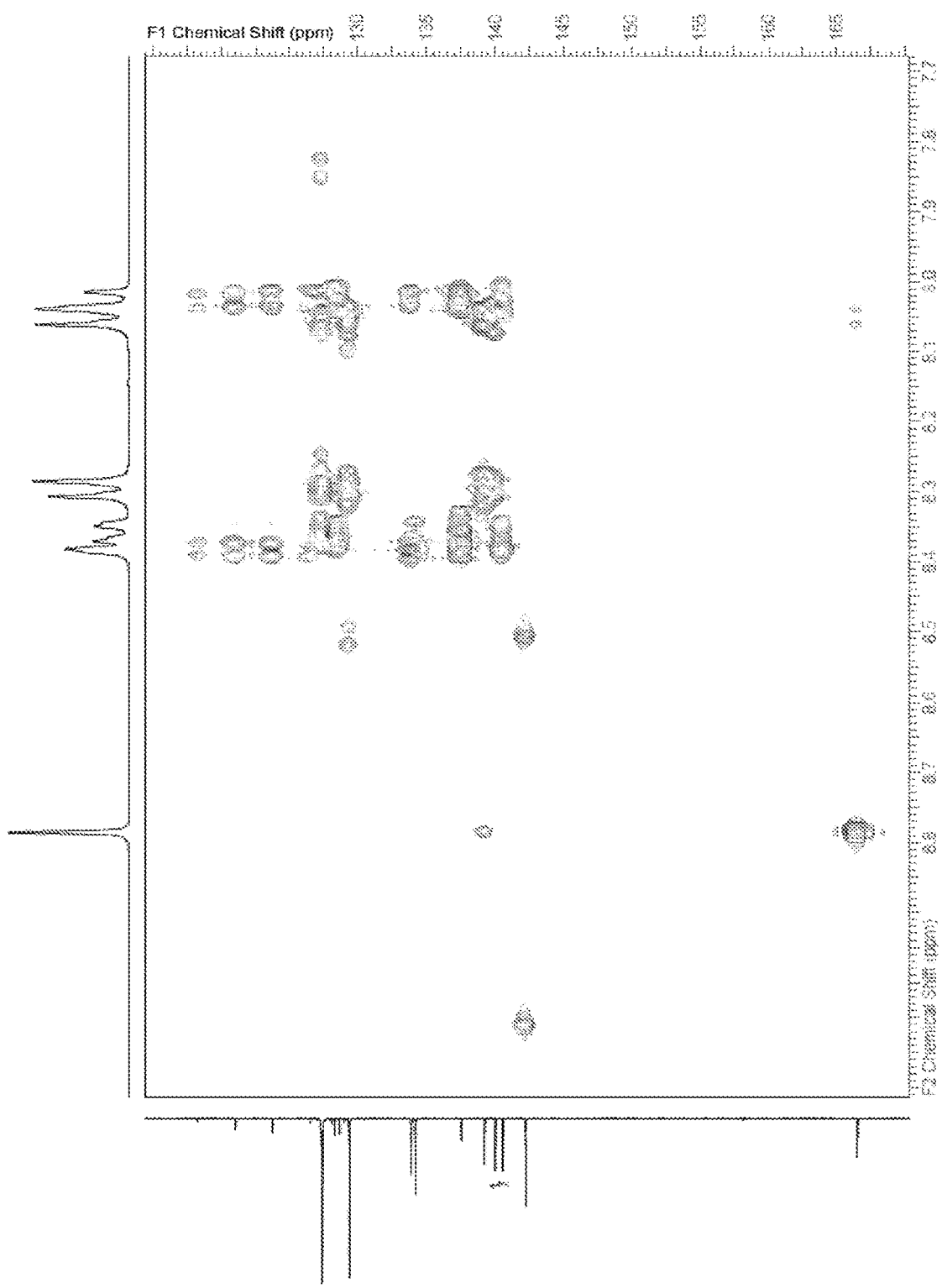
FIG. 1E shows the HMBC of Compound 1 in DMSO-d6 (400 MHz) as synthesized from Route C.

Step 6: 4-((4-Chloro-3-(trifluoromethyl)phenyl)sulfonyl) aniline (7.0 g, 20.9 mmol) and IPA (93 mL) was added to a reaction vessel at 30° C. to give a suspension. p-TSA.H₂O (595 mg) was added and the reaction mixture was heated to 80-85° C. 2-Chloro-1,3,4-thiadiazole (4.6 g, 38.2 mmol) in IPA (20 mL) was added at 80-85° C. over a period of 5 h and the mixture was stirred for 1 h after the addition was complete. The mixture was cooled to 30° C. and stood for 15 h. The reaction mixture was concentrated to dryness. MTBE (50 mL) was added and the mixture was stirred for 2 h at 30° C. and filtered. The MTBE layer was retained and contained 1.0 g by assay yield (3%, 32 g×3%=1.0 g) of 4-(4-((4-chloro-3-(trifluoromethyl)phenyl)sulfonyl)phenyl)-2,4-dihydro-3H-1,2,4-triazole-3-thione. The filter cake was poured into 100 mL 2-MeTHF and saturated NaHCO₃ was added to pH=7-8. Assay yield of the 2-MeTHF layer indicted 4.1 g grams (102 g×4%=4.1 g) of 4-(4-((4-chloro-3-(trifluoromethyl)phenyl)sulfonyl)phenyl)-2,4-dihydro-3H-1,2,4-triazole-3-thione. Total weight by assay yield=5.1 g, 58% yield. 1H NMR (400 MHz, DMSO-d6) δ 14.09 (s, 1H), 8.78 (s, 1H), 8.38-8.35 (m, 2H), 8.30-8.28 (m, 2H), 8.03 (m, 3H). LCMS ES+(m/z), 420.0 (M+1)+, Cl pattern found. The ¹H NMR spectrum of Compound 1 is shown in FIG. 1A. FIG. 1D shows a 2D NOESY spectrum of Compound 1 in DMSO-d6 (400 MHz) as synthesized from Route C. The NOESY spectrum shows nOe coupling between the triazole thione CH and the phenyl CH, corresponding to R¹ in Formula 1. FIG. 1E shows the HMBC of Compound 1 in DMSO-d6 (400 MHz) showing a correlation between the triazole thione CH, and the aromatic carbon connected to the triazole thione.

(iv.) Synthesis Route D

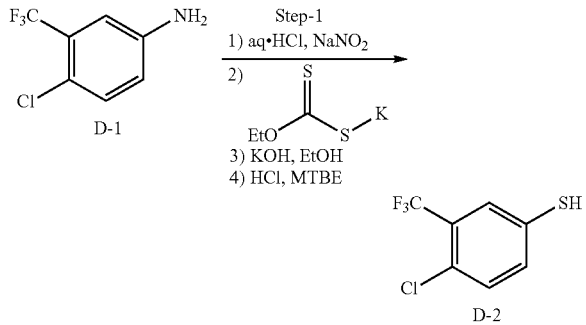

Step 1: Purified water (178 kg) was charged into a reaction vessel followed by concentrated HCl (216 kg) and 4-chloro-3-(trifluoromethyl)aniline (60.55 kg, 1.0 eq). The mixture was heated to 45-55° C., stirred for 5 h and then cooled −5~5° C. A solution of NaNO$_2$ (25.65 kg) in 38 kg water was added drop-wise over 1-2 h at −5~5° C. After addition, the mixture was stirred at 0-5° C. for 2 h. The solution (528.2 kg) and an aqueous solution of potassium O-ethyl carbonodithioate (63.5 kg potassium O-ethyl carbonodithioate and 242 kg purified water) were added at 15-25° C. simultaneously over 2-6 h into a reactor containing toluene (211.6 kg, 4V) and 0.5 volumes of purified water. The resultant mixture was stirred at 20° C. for 5-12 h. The layers were separated, and the aqueous phase was extracted with toluene (112 kg). The organic layers were combined and washed with purified water 3 times.

Ethanol (208 kg) and water (32 kg) were charged into a second reaction vessel followed by KOH (71 kg). The mixture was heated to 75-82° C. under N$_2$ protection. The toluene solution from the extraction was added at 75-82° C. under N$_2$ protected over 5 h. The mixture was stirred at 78° C. for 5 h. The mixture was then distilled to 2-4 volumes at an inner temperature not more than 45° C. and distilled again with toluene (169 kg) to remove EtOH. Purified water (250 kg) was charged into the vessel with stirring; the toluene phase was separated and the aqueous layer was washed with 2 volumes of toluene 2 times to give a product rich aqueous layer.

The aqueous layer was cooled to 0-10° C. and purged with N$_2$ for 2 h at which time nitrogen-purged 6N HCl (2.0-5.0×) was added dropwise at 0-10° C. until the pH was between 1 and 2. The mixture was stirred for 1 h at 0-10° C. The resulting mixture was stirred for 1 h at 0-10° C. and was then extracted with MTBE (250 kg), which had also been purged with N$_2$ for 2 h. The organic layer was separated and washed with purified water twice (2×268 kg) and the resulting organic layer was stored for further processing. 36.6 kg of 4-chloro-3-(trifluoromethyl)benzenethiol (D-2) was obtained as a solution in MTBE. The product was a mixture of monomer and dimer with a yield of 55.5%.

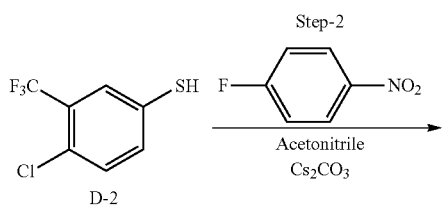

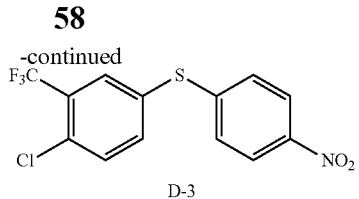

Step 2: The mixture of D-2 and dimer (34.1 kg, 158.8 kg×21.5 wt %, 1.0 eq.) in MTBE (3 vol.) was charged into a reaction vessel. Acetonitrile (482 kg, 18.6 vol.) was added followed by Cs$_2$CO$_3$ (157 kg, 3.0 eq.) and 1-fluoro-4-nitrobenzene (29.6 kg, 1.3 eq.). The mixture was heated to 60-65° C. and stirred at that temperature for 57 h. The mixture was cooled to 20-30° C. Celite (37 kg) was added and, after stirring for 1-3 h, the mixture was filtered and washed with acetonitrile (163 kg). The acetonitrile solution was concentrated to 6-7 volumes below 45° C. under vacuum. The mixture was then stirred at 40-45° C. for 0.5-1 h until a clear solution was achieved. The mixture was cooled to 25-30° C. over 1-2 hours and then stirred for an additional 0.5-1 h. Seed crystals of D-3 (96 g) were added, and the mixture was stirred for 1-2 h. Water (136 kg) was added dropwise over 7 hours, and the mixture continued to stir at 25-30° C. for 10-20 hours. The mixture was centrifuged and the resultant cake was washed twice with 104 kg of ACN/H$_2$O (6:4 by volume). The wet cake was dried at 50-60° C. for 24 h to give 40.4 kg of (4-chloro-3-(trifluoromethyl)phenyl)(4-nitrophenyl)sulfane (D-3) in 74.4% isolated yield.

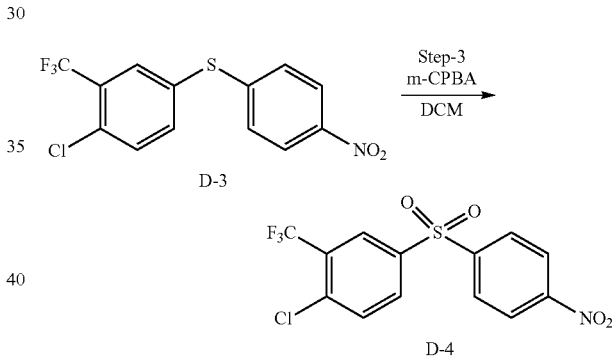

Step 3: DCM (1480 kg) was charged into a reaction vessel followed by 40.4 kg of D-3. The mixture was heated to 33-37° C. MCPBA (3×20.6 kg) was added portion-wise at 33-37° C. and stirred for 20-30 minutes between additions. After the addition was complete, the reaction was stirred for 3-5 hours at 33-37° C. After cooling to 20-30° C., 16 wt % Na$_2$SO$_3$ aq. (344 kg) and 16% Na$_2$CO$_3$ aq. (342 kg) were added. The mixture was stirred for 1-2 h and then extracted with DCM (342 kg). The organic layer was separated and washed with an aqueous solution of 7 wt % Na$_2$SO$_4$ (134 kg) 2 times. The organic layer was concentrated to 3-4 vol. under reduced pressure below 35° C., while keeping the walls of the reaction vessel clean by rinsing down the sides with DCM (114 kg). MTBE (322 kg) was added, and the mixture was stirred at 40-50° C. for 1-2 h, cooled to 5-10° C., and stirred at 5-10° C. for 4-6 h. The precipitate was filtered and washed with solvent (DCM:MTBE=1:3, 118 kg) and re-suspended in MTBE (156 kg) and DCM (66 kg). After stirring at 5-10° C. for 1-2 h, the precipitate was filtered and washed with solvent (DCM:MTBE=1:3.38 kg). The filter cake was dried under vacuum at 40-45° C. for 8-12 h to give 39.87 kg (91.4% yield) of 1-chloro-4-((4-nitrophenyl)sulfonyl)-2-(trifluoromethyl)benzene (D-4).

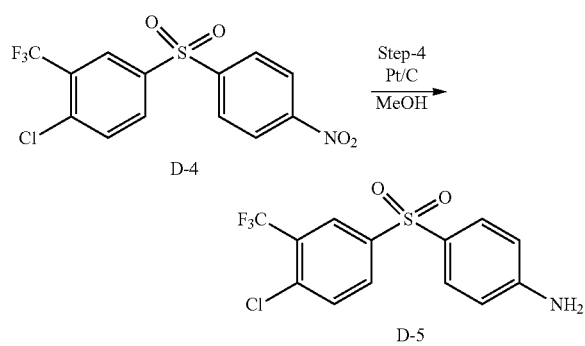

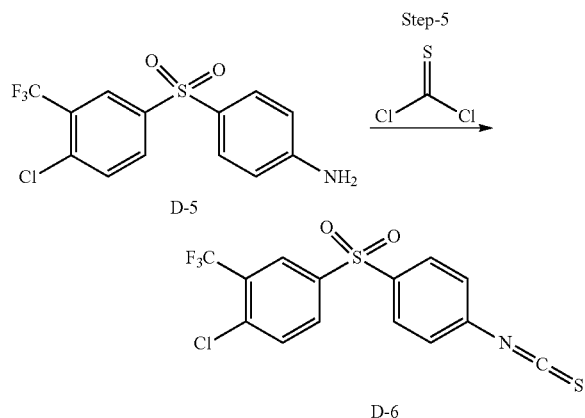

Step 4: Pt/V/C (2.9 kg) was added to a reaction vessel containing D-4 (38.4 kg) in THF (198 kg) and MeOH (126 kg). The reaction vessel was evacuated and back-filled with nitrogen 3 times and then evacuated and back-filled with hydrogen 3 times. The temperature was adjusted to 60° C., and the reaction was stirred under $H_2$ (0.3-0.4 MPa) for 17 hours. The reaction mixture was filtered and washed with THF (97 kg). The filtrate was concentrated to 2-3 volumes. The solvent was exchanged by methanol addition (120 kg) and concentrated to 2-3 volumes (repeated 3 times). Methanol (64 kg) was added to the reaction vessel and the temperature was adjusted to 60° C. with stirring for 0.5-1 hour. The temperature was lowered to 55° C., and seed crystals of D-5 (0.04 kg) were added. The mixture was stirred at 50-60° C. for 5 hours and then lowered to 20° C. over 6 hours. Water (100 kg) was added over 5 h, and then the suspension was stirred for 7 h. The precipitate was filtered and washed with a MeOH:$H_2O$ solution (3:1, 98 kg). The filter cake was dried under vacuum at 45° C. for 16 h to give 4-((4-chloro-3-(trifluoromethyl)phenyl)sulfonyl)aniline, D-5, (31.9 kg) in 90.6% yield.

Step 5: To a reaction vessel containing a solution of $NaHCO_3$ (23.4 kg) and water (293 kg), D-5 (28.5 kg) was added followed by 361 kg of DCM. After stirring at 15-25° C. for 0.5 h, the reaction vessel was cooled to −5-5° C. Sequential addition of thiophosgene (12.3 kg, 6 kg) added dropwise with stirring at −5~5° C. for 4 hours followed by $NaHCO_3$ (3.7 kg, 2.9) was repeated twice. A final portion of thiophosgene (6.0 kg) was added, and the reaction was stirred at −5~5° C. for 2-10 h, warmed to 15-25° C. and stirred for an additional 1-2 h. The organic layer was separated and washed with water (112 kg). The organic layer was concentrated to 2-3 volumes under vacuum below 25° C. DCM (185 kg) addition and concentration (to 2-3 volumes under vacuum below 25° C.) was repeated 3 times with a final DCM concentration of 4-5 volumes. Solvent exchange was accomplished by portion-wise addition of the DCM solution of D-6 to a second reaction vessel charged with 180 kg of methylcyclohexane with stirring at 20-25° C. for 2-4 hours and concentration to 7.5-8.5 volumes under vacuum at a temperature below 25° C. between additions. Methylcyclohexane (2×100 kg) was added to the vessel, and the mixture was concentrated to 4.0-4.5 volumes under vacuum below 35° C. twice. Additional methylcyclohexane (135 kg) was added, and the mixture was stirred at 55~65° C. for 3-4 h, cooled slowly (10-12 h) to 0-5° C. and stirred for 6-10 h. The suspension was filtered, washed with 68 kg methylcyclohexane and dried at 40-50° C. for 24 h to give 29.9 kg of 1-chloro-4-((4-isothiocyanatophenyl)sulfonyl)-2-(trifluoromethyl)benzene (D-6) in 93.2% yield.

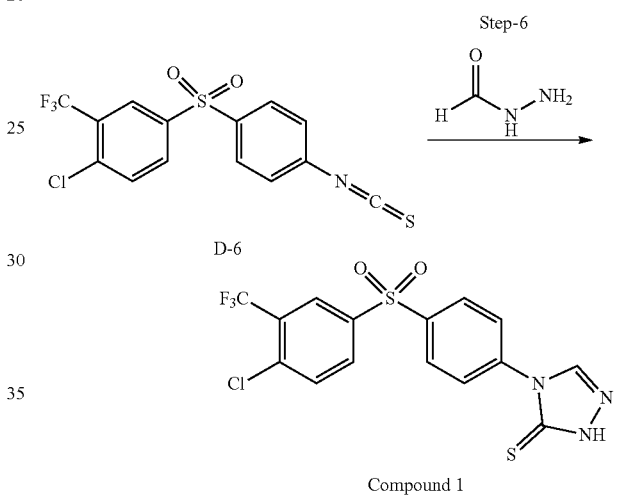

Step 6: To a reaction vessel charged with D-6 (30.95 kg) and DABCO (11.4 kg) was added THF (268 kg) under nitrogen. The reaction vessel was cooled to 10-20° C. and stirred for 30-60 min and before adding formohydrazide (5.6 kg) under nitrogen. The reaction was stirred at 10~20° C. for 1.5 h, warmed to 35~45° C., then stirred for 17 hours, and then warmed to 45~55° C. and stirred 9 hours. The reaction was cooled to 20~40° C. and transferred to a second reaction vessel through a fine filter. The mixture was concentrated to ~2 volumes while keeping the temperature below 40° C. Water (251 kg) was added under $N_2$ followed by the addition of 6N HCl (30.9 kg) until a pH of 4 was reached. The reaction was warmed to 40~50° C., stirred for 3 hours, and then cooled to 15~25° C. and stirred for 4 hours. The mixture was centrifuged, and the precipitate was washed with water:THF (3:1, 72 kg) and water (94 kg). The solid product was dried at 40~50° C. for 27 h to give Compound 1 in 93.7% yield and 97% purity.

4-(4-((4-chloro-3-(trifluoromethyl)phenyl)sulfonyl)phenyl)-2,4-dihydro-3H-1,2,4-triazole-3-thione was further purified by polish filtration and recrystallization. 17.4 kg of the 4-(4-((4-chloro-3-(trifluoromethyl)phenyl)sulfonyl)phenyl)-2,4-dihydro-3H-1,2,4-triazole-3-thione dissolved in acetone (158 kg) and stirred at 20-30° C. until a clear solution was obtained. The solution was filtered through a fine filter and concentrated to 7-9 volumes under vacuum while keeping the temperature below 40° C. The mixture was cooled to 30° C., charged with seed crystals (21 g), stirred 7 h, then concentrated to 3-5 volumes under vacuum while keeping the temperature below 40° C.

Solvent exchange was performed two times with ethanol by sequential addition of ethanol (56 kg, 52 kg), stirring, and concentrating to 3-5 volumes under vacuum at a temperature below 40° C. The compound was recrystallized in ethanol (88 kg) by heating to 75~82° C., stirring the mixture for 10 h, cooling the mixture to 15-25° C. over 5 h, and stirring the mixture at 15-25° C. for 8 h. The mixture was filtered, washed with 160 g ethanol, and dried at 40-50° C. for 10-16 h to give 16.64 kg of Compound 1 in 99% purity.

Example 2: 4-(4-((4-chloro-3-(trifluoromethyl)phenyl)sulfonyl)-2-morpholinophenyl)-2,4-dihydro-3H-1,2,4-triazole-3-thione (Compound 2)

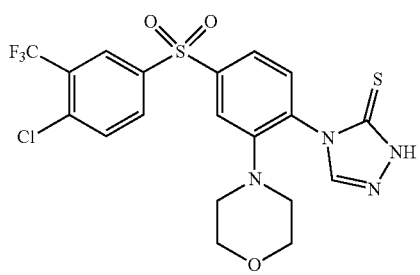 [SMILES: O=S(=O)(c1ccc(-n2cn[nH]c2=S)c(N2CCOCC2)c1)c1ccc(Cl)c(C(F)(F)F)c1]

The synthesis of 4-(4-((4-chloro-3-(trifluoromethyl)phenyl)sulfonyl)-2-morpholinophenyl)-2,4-dihydro-3H-1,2,4-triazole-3-thione was accomplished in a similar manner as described in Synthesis Route B of Example 1 from 4-(5-fluoro-2-nitrophenyl)morpholine. $^1$H NMR (300 MHz, DMSO-d6) δ 14.00 (1H, s), 8.41 (2H, m), 8.67 (1H, s), 8.04 (1H, d, J=6 Hz), 7.90 (1H, dd, J=3, 6 Hz), 7.83 (1H, d, J=3 Hz), 7.71 (1H, d, J=6 Hz), 3.55 (4H, m), 2.82 (4H, m). LCMS ES+(m/z), 505.0 (M+1)+, Cl pattern found.

Example 3: 4-(4-(phenylsulfonyl)phenyl)-2,4-dihydro-3H-1,2,4-triazole-3-thione (Compound 3)

Step 1: Synthesis of Sodium Benzenesulfinate

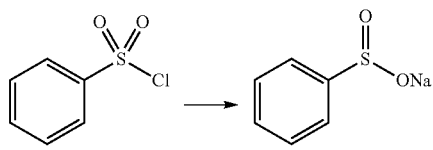

Phenyl sulfonyl chloride (3.5 g, 19.9 mmol, 1 eq.) was added to a solution of sodium sulfite (5 g, 39.8 mmol, 2 eq.) and sodium bicarbonate (3.3 g, 39.8 mmol, 2 eq.) in water (50 mL). The reaction was stirred for 2 hours at rt. The water was removed in vacuo and the residue was suspended in methanol and filtered. The residue was washed with methanol 3 more times and filtered. The methanol filtrates were combined and concentrated. The resultant solid was re-suspended in methanol and filtered. The filtrate was concentrated to give crude sodium benzenesulfinate, which was used for next reaction without further purification. Neg. LC-MS: 141.14 (M−H)⁻, C₆H₅NaO₂S.

Step 2: Synthesis of 4,4,5,5-Tetramethyl-2-(4-nitrophenyl)-1,3,2-dioxaborolane

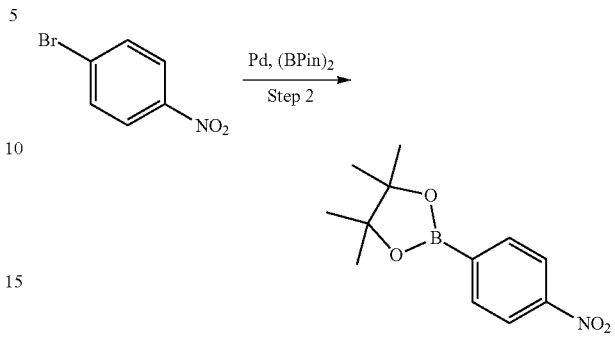

A mixture of 1-bromo-4-nitrobenzene (2.02 g, 0.01 mol, 1 eq.), 4,4,4',4',5,5,5',5'-octamethyl-2,2'-bi(1,3,2-dioxaborolane) (2.54 g, 0.01 mol, 1 eq.), potassium acetate (2.88 g, 0.03 mol, 1 eq.), and PdCl₂(dppf) (0.82 g, 1.0 mmol, 0.1 eq.) in dioxane (35 mL) was refluxed overnight. The mixture was cooled to rt, diluted with water (100 mL), and extracted with ethyl acetate (100 mL×3). The organic extracts were combined, washed with brine (50 mL), dried over anhydrous sodium sulfate, and concentrated. The residue was purified by silica gel column chromatography (petroleum ether/ethyl acetate=20:1 to 5:1) to give the product (1.83 g, 73% yield).

Step 3: Synthesis of 1-nitro-4-(phenylsulfonyl)benzene

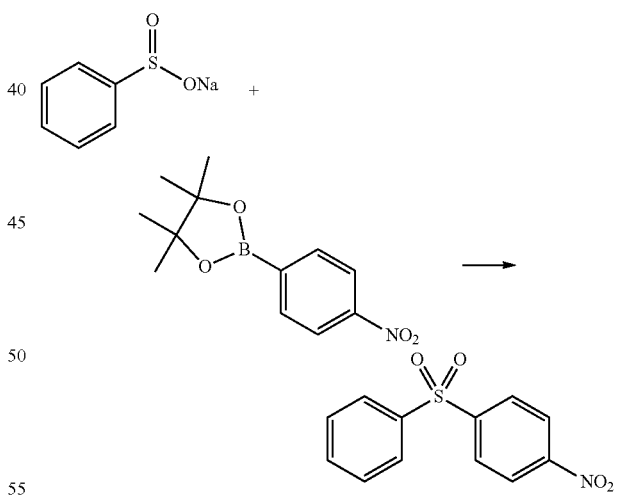

Potassium carbonate (2.01 g, 14.6 mmol, 2 eq.), 4A MS, and Cu(OAc)₂ (1.49 g, 8.0 mmol, 1.1 eq.) were added successively to a solution of compound 4,4,5,5-Tetramethyl-2-(4-nitrophenyl)-1,3,2-dioxaborolane (1.82 g, 7.3 mmol, 1 eq.) and crude sodium benzenesulfinate (2.39 g, 14.6 mmol, 2 eq.) in DMSO (50 mL). The reaction was stirred overnight at 45° C. under the atmosphere of an oxygen balloon. The reaction mixture was poured into water and extracted with ethyl acetate. The organic extracts were combined, washed with brine, dried over anhydrous sodium sulfate, and concentrated. The residue was purified by silica gel column chromatography to give 1-nitro-4-(phenylsulfonyl)benzene, 0.71 g, 37% yield.

Step 4: Synthesis of 4-(phenylsulfonyl)aniline

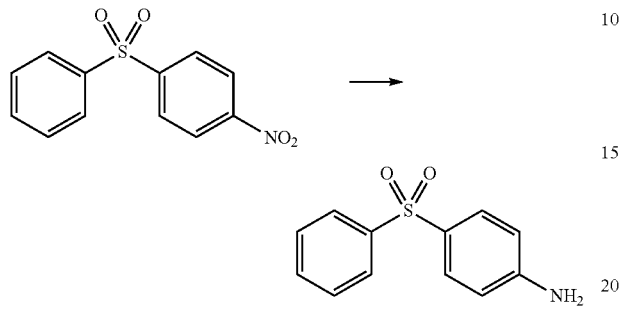

1-Nitro-4-(phenylsulfonyl)benzene (0.7 g, 2.66 mmol, 1 eq.) was dissolved in acetic acid (10 mL) and Fe (1.49 g, 26.6 mmol, 10 eq.) was added. The reaction was heated at 60° C. for 2 h. The mixture was cooled to rt, diluted with ethyl acetate, filtered, and the cake was washed with ethyl acetate. The filtrate was washed with brine. The organic extract was concentrated and the residue was purified by silica gel column chromatography to give 4-(phenylsulfonyl)aniline. (0.52 g, 2.23 mmol, 84% yield). Pos. LC-MS: 233.92 (M+H)+, $C_{12}H_{11}NO_2S$.

Step 5: Synthesis of 1-isothiocyanato-4-(phenylsulfonyl)benzene

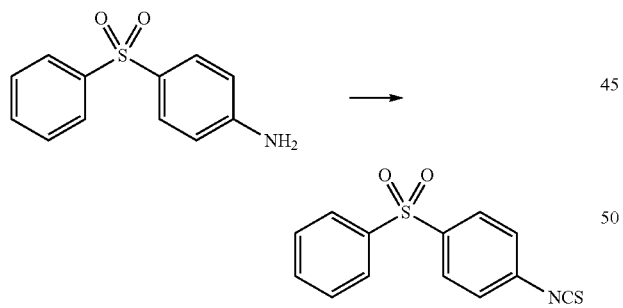

Thiophosgene (308 mg, 2.68 mmol, 1.2 eq.) was added to a mixture of 4-(phenylsulfonyl)aniline. (520 mg, 2.23 mmol, 1 eq.) and saturated sodium bicarbonate-water solution (10 mL) in chloroform (10 mL). The reaction was stirred for 2 h at rt under nitrogen protection. The mixture was extracted with dichloromethane twice. The organic extracts were combined, washed with brine, dried over anhydrous sodium sulfate, and concentrated to afford crude 1-isothiocyanato-4-(phenylsulfonyl)benzene, which was used for next reaction without further purification.

Step 6: Synthesis of 4-(4-(phenylsulfonyl)phenyl)-2,4-dihydro-3H-1,2,4-triazole-3-thione

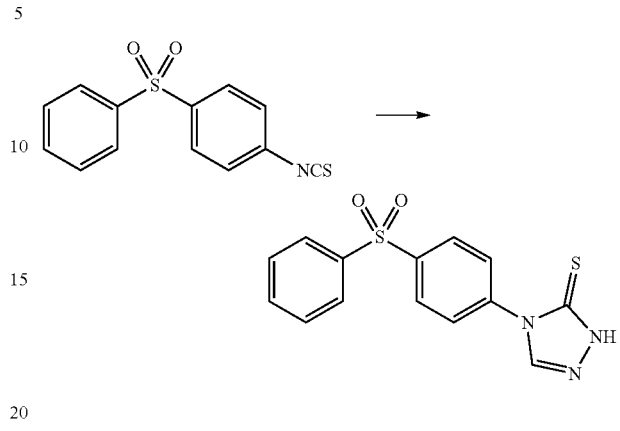

A solution of crude 1-isothiocyanato-4-(phenylsulfonyl)benzene (275 mg, 1.0 mmol, 1 eq.) and formohydrazide (60 mg, 1.0 mmol, 1 eq.) in ethanol (5 mL) was refluxed for 30 min. The solvent was removed and the residue was dissolve in 2% NaOH (5 mL). The reaction was heated at 100° C. for another 2 h. The mixture was cooled to rt and acidified to pH=3-4 by HCl. The resulting precipitate was extracted with dichloromethane two times. The organic extracts were combined, washed with brine, dried over anhydrous sodium sulfate, and concentrated. The residue was re-crystallized in ethanol to give 4-(4-(phenylsulfonyl)phenyl)-2,4-dihydro-3H-1,2,4-triazole-3-thione (48 mg, 0.15 mmol, 15% yield) as an off-white solid. Neg. LC-MS: 316.1 (M–H)⁻, $C_{14}H_{11}N_3O_2S_2$. ¹H NMR (DMSO-d6, 400 MHz) δ: 14.07 (br, 1H), 8.77 (s, 1H), 8.16 (d, J=8.4 Hz, 2H), 7.96-8.15 (m, 4H), 7.64-7.75 (m, 3H).

Example 4: 4-(4-((4-chlorophenyl)sulfonyl)phenyl)-2,4-dihydro-3H-1,2,4-triazole-3-thione (Compound 4)

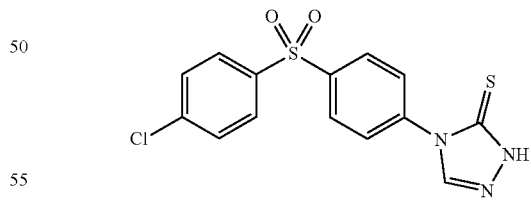

4-(4-((4-Chlorophenyl)sulfonyl)phenyl)-2,4-dihydro-3H-1,2,4-triazole-3-thione was synthesized in a similar manner as described for 4-(4-(phenylsulfonyl)phenyl)-2,4-dihydro-3H-1,2,4-triazole-3-thione. Yield for step 6: 22%, off-white solid. Neg. LC-MS: 350.0 (M–H)⁻, $C_{14}H_{10}ClN_3O_2S_2$. ¹H NMR (DMSO-d6, 400 MHz) δ: 14.08 (br, 1H), 8.77 (s, 1H), 8.18 (d, J=8.4 Hz, 2H), 7.98-8.06 (m, 4H), 8.79 (d, J=8.4 Hz, 2H).

Example 5: 4-(4-((4-Chloro-3-methylphenyl)sulfonyl)phenyl)-2,4-dihydro-3H-1,2,4-triazole-3-thione (Compound 5)

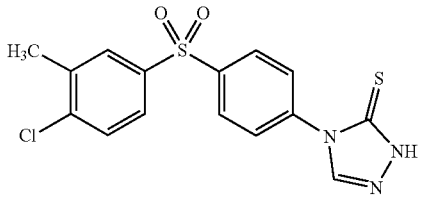 [SMILES: Cc1cc(S(=O)(=O)c2ccc(-n3cn[nH]c3=S)cc2)ccc1Cl]

4-(4-((4-Chloro-3-methylphenyl)sulfonyl)phenyl)-2,4-dihydro-3H-1,2,4-triazole-3-thione was synthesized in a similar manner as described for 4-(4-(phenylsulfonyl)phenyl)-2,4-dihydro-3H-1,2,4-triazole-3-thione. Yield for Step 6: 12%, pale yellow solid. LC-MS: 364.0 (M–H)⁻, $C_{15}H_{12}ClN_3O_2S_2$. ¹H NMR (DMSO-d6, 400 MHz) δ: 14.09 (br, 1H), 8.77 (s, 1H), 8.17 (d, J=8.4 Hz, 2H), 8.07 (s, 1H), 7.99 (d, J=8.4 Hz, 2H), 7.86 (d, J=7.6 Hz, 1H), 7.71 (d, J=8.4 Hz, 1H), 2.42 (s, 3H).

Example 6: 4-(4-((3-(Trifluoromethyl)phenyl)sulfonyl)phenyl)-2,4-dihydro-3H-1,2,4-triazole-3-thione (Compound 11)

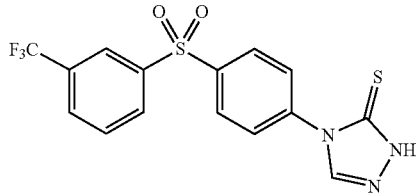 [SMILES: O=S(=O)(c1ccc(-n2cn[nH]c2=S)cc1)c1cccc(C(F)(F)F)c1]

4-(4-((3-(Trifluoromethyl)phenyl)sulfonyl)phenyl)-2,4-dihydro-3H-1,2,4-triazole-3-thione was synthesized in a similar manner as described for 4-(4-(phenylsulfonyl)phenyl)-2,4-dihydro-3H-1,2,4-triazole-3-thione. Yield for step 6: 13%, off-white solid. Neg. LC-MS: 384.1 (M–H)⁻, $C_{15}H_{10}F_3N_3O_2S_2$. ¹H NMR (DMSO-d6, 400 MHz) δ: 14.08 (br, 1H), 8.78 (s, 1H), 8.37 (m, 2H), 8.28 (d, J=8.4 Hz, 2H), 8.14 (d, J=7.6 Hz, 1H), 8.02 (d, J=8.4 Hz, 2H), 7.93 (m, 1H).

Example 7: 4-(4-((3-methoxyphenyl)sulfonyl)phenyl)-2,4-dihydro-3H-1,2,4-triazole-3-thione (Compound 12)

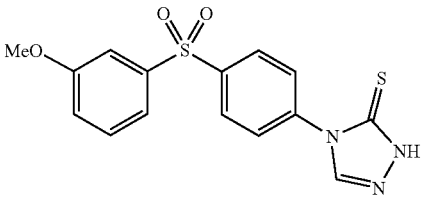 [SMILES: COc1cccc(S(=O)(=O)c2ccc(-n3cn[nH]c3=S)cc2)c1]

4-(4-((3-Methoxyphenyl)sulfonyl)phenyl)-2,4-dihydro-3H-1,2,4-triazole-3-thione was synthesized in a similar manner as described for 4-(4-(phenylsulfonyl)phenyl)-2,4-dihydro-3H-1,2,4-triazole-3-thione. Yield for step 6: 57%, off-white solid. LC-MS: 346.0 (M–H)⁻, $C_{15}H_{13}N_3O_3S_2$. ¹H NMR (DMSO-d6, 400 MHz) δ: 14.09 (br, 1H), 8.78 (s, 1H), 8.19 (d, J=8.4 Hz, 2H), 7.98 (d, J=8.4 Hz, 2H), 7.56 (m, 2H), 7.52 (s, 1H), 7.28 (m, 1H), 3.85 (s, 3H).

Example 8: 4-(4-(3-(dimethylamino)phenylsulfonyl)phenyl)-1H-1,2,4-triazole-5(4H)-thione (Compound 15)

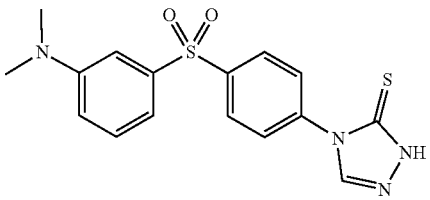 [SMILES: CN(C)c1cccc(S(=O)(=O)c2ccc(-n3cn[nH]c3=S)cc2)c1]

Step 1: N,N-dimethyl-3-(4-nitrophenylthio)aniline

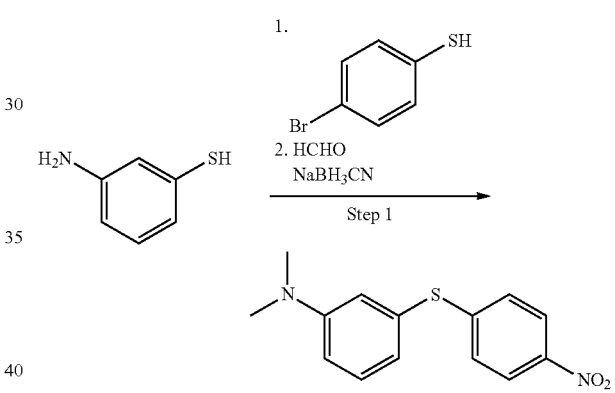

3-Aminobenzenethiol (2 g, 16.0 mmol, 1 eq.) was added to a mixture of 4-bromonitrobenzene (3.5 g, 16.0 mmol, 1 eq.) and potassium carbonate (4.4 g, 32.0 mmol, 2 eq.) in DMF (30 mL). The reaction was stirred for 2 hours at rt. The mixture was poured into water and extracted with ethyl acetate three times. The organic extracts were combined, washed with brine, dried over anhydrous sodium sulfate, and concentrated. The residue was purified by silica gel column chromatography (petroleum ether/ethyl acetate=50:1 to 10:1) to give 3-(4-nitrophenylthio)aniline (2.74 g, 70% yield). Pos. LC-MS: 246.7 (M+H)⁺, $C_{12}H_{10}N_2O_2S$. ¹H NMR (DMSO-d6, 400 MHz) δ: 8.12 (d, J=8.4 Hz, 2H), 7.31 (d, J=8.4 Hz, 2H), 7.16 (m, 1H), 6.75 (s, 1H), 6.68 (m, 2H), 5.45 (br, 2H). 3-(4-Nitrophenylthio)aniline (1 g, 4.1 mmol, 1 eq.) was dissolved in acetonitrile (20 mL). Acetic acid (1 ml) and formaldehyde water solution (2.5 mL, 32.0 mmol, 8 eq.) were added. The solution was stirred for 10 min and NaBH₃CN (1.42 g, 20.0 mmol, 5 eq.) was added. The reaction was stirred for another 2 h. The mixture was diluted with water and extracted with ethyl acetate three times. The organic extracts were combined, washed with brine, dried over anhydrous sodium sulfate, and concentrated. The residue was purified by silica gel column chromatography (petroleum ether/ethyl acetate=200:1 to 100:1) to give N,N- dimethyl-3-(4-nitrophenylthio)aniline (340 mg, 31% yield). Pos. LC-MS: 274.7 (M+H)$^+$, $C_{14}H_{14}N_2O_2S$.

Step 2:
N,N-dimethyl-3-(4-nitrophenylsulfonyl)aniline

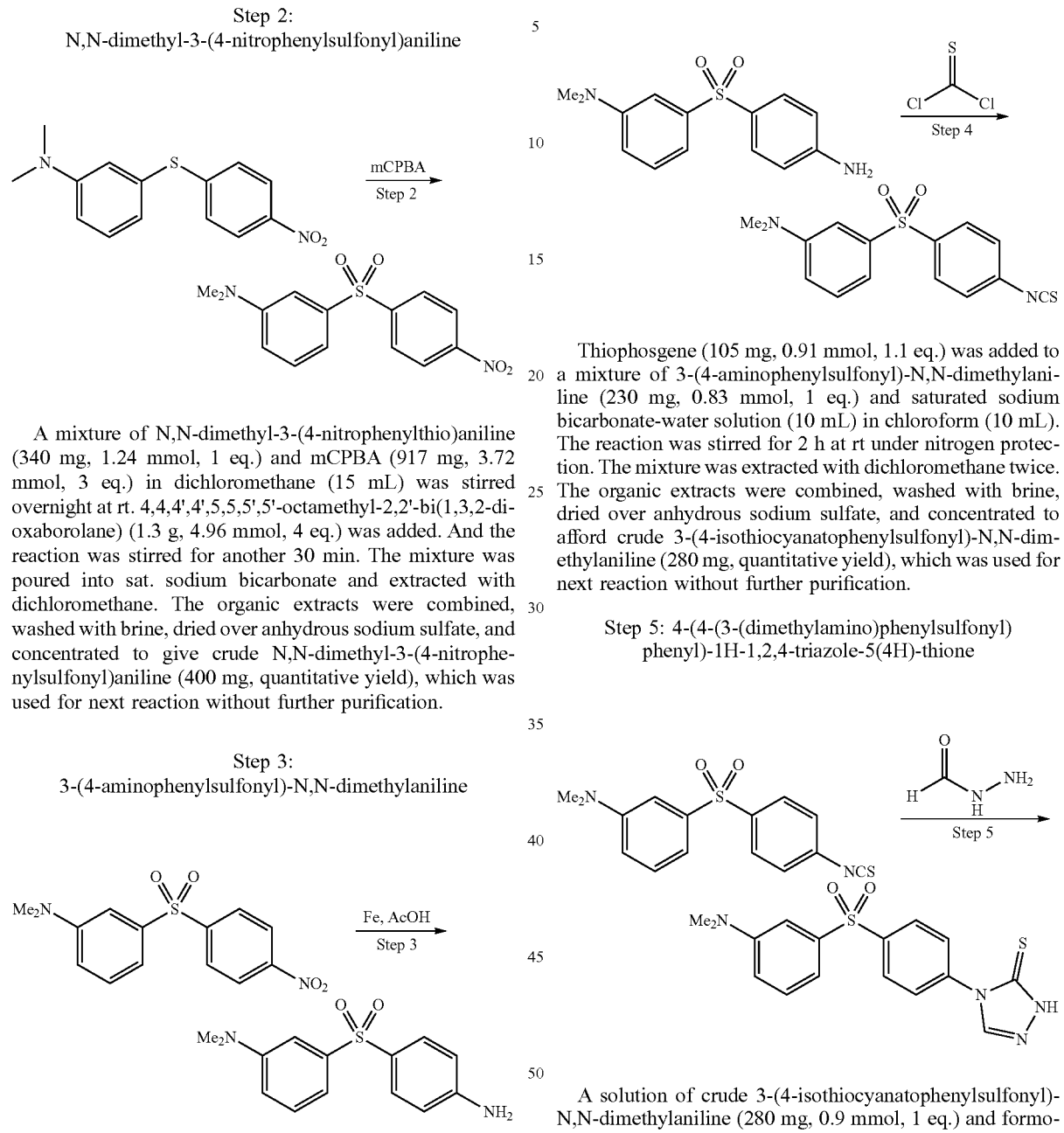

A mixture of N,N-dimethyl-3-(4-nitrophenylthio)aniline (340 mg, 1.24 mmol, 1 eq.) and mCPBA (917 mg, 3.72 mmol, 3 eq.) in dichloromethane (15 mL) was stirred overnight at rt. 4,4,4',4',5,5,5',5'-octamethyl-2,2'-bi(1,3,2-dioxaborolane) (1.3 g, 4.96 mmol, 4 eq.) was added. And the reaction was stirred for another 30 min. The mixture was poured into sat. sodium bicarbonate and extracted with dichloromethane. The organic extracts were combined, washed with brine, dried over anhydrous sodium sulfate, and concentrated to give crude N,N-dimethyl-3-(4-nitrophenylsulfonyl)aniline (400 mg, quantitative yield), which was used for next reaction without further purification.

Step 3:
3-(4-aminophenylsulfonyl)-N,N-dimethylaniline

N,N-dimethyl-3-(4-nitrophenylsulfonyl)aniline (400 mg, 1.3 mmol, 1 eq.) was dissolved in acetic acid (10 mL) and Fe (728 mg, 13.0 mmol, 10 eq.) was added. The reaction was heated at 60° C. for 2 h. The mixture was cooled to rt, diluted with ethyl acetate, filtered, and the cake was washed with ethyl acetate. The filtrate was washed with brine. The organic extract was concentrated and the residue was purified by silica gel column chromatography (petroleum ether/ethyl acetate=6:1 to 3:1) to give 3-(4-aminophenylsulfonyl)-N,N-dimethylaniline (240 mg, 67% yield). Pos. LC-MS: 276.9 (M+H)$^+$, $C_{14}H_{16}N_2O_2S$.

Step 4: 3-(4-isothiocyanatophenylsulfonyl)-N,N-dimethylaniline

Thiophosgene (105 mg, 0.91 mmol, 1.1 eq.) was added to a mixture of 3-(4-aminophenylsulfonyl)-N,N-dimethylaniline (230 mg, 0.83 mmol, 1 eq.) and saturated sodium bicarbonate-water solution (10 mL) in chloroform (10 mL). The reaction was stirred for 2 h at rt under nitrogen protection. The mixture was extracted with dichloromethane twice. The organic extracts were combined, washed with brine, dried over anhydrous sodium sulfate, and concentrated to afford crude 3-(4-isothiocyanatophenylsulfonyl)-N,N-dimethylaniline (280 mg, quantitative yield), which was used for next reaction without further purification.

Step 5: 4-(4-(3-(dimethylamino)phenylsulfonyl)phenyl)-1H-1,2,4-triazole-5(4H)-thione A solution of crude 3-(4-isothiocyanatophenylsulfonyl)-N,N-dimethylaniline (280 mg, 0.9 mmol, 1 eq.) and formohydrazide (54 mg, 0.9 mmol, 1 eq.) in ethanol (10 mL) was refluxed for 30 min. The solvent was removed and the residue was dissolve in 2% NaOH (10 mL). The reaction was heated at 100° C. for another 2 h. The mixture was cooled to rt and acidified to pH=3-4 by HCl. The resulting precipitate was extracted with dichloromethane two times. The organic extracts were combined, washed with brine, dried over anhydrous sodium sulfate, and concentrated. The residue was re-crystallized in ethanol to give 4-(4-(3-(dimethylamino)phenylsulfonyl)phenyl)-1H-1,2,4-triazole-5(4H)-thione (30 mg, 9% yield). Neg. LC-MS: 360.70 (M+H)$^+$, $C_{16}H_{16}N_4O_2S_2$. $^1$H NMR (DMSO-d6, 400 MHz) δ: 14.08 (br, 1H), 8.77 (s, 1H), 8.16 (d, J=7.2 Hz, 2H), 7.95 (d, J=7.2 Hz, 2H), 7.40 (m, 1H), 7.19 (m, 2H), 6.99 (m, 1H), 2.97 (s, 6H).

Example 9: 4-(4-((4-chloro-3-(trifluoromethyl)phenyl)sulfonyl)-2-(piperidin-1-yl)phenyl)-2,4-dihydro-3H-1,2,4-triazole-3-thione (Compound 19)

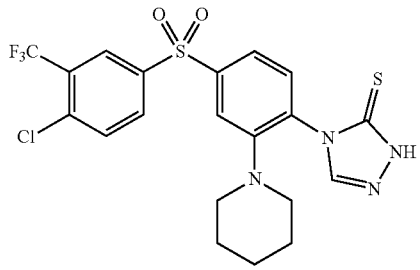 [SMILES: O=S(=O)(c1ccc(-n2cn[nH]c2=S)c(N2CCCCC2)c1)c1ccc(Cl)c(C(F)(F)F)c1]

Step 1: Synthesis of 1-(5-bromo-2-nitrophenyl)piperidine

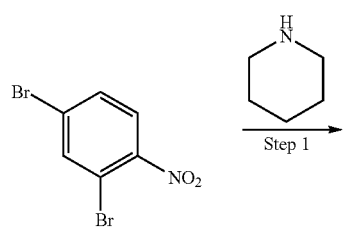

A mixture of 2,4-dibromo-1-nitrobenzene (2.81 g, 10.0 mmol), piperidine (0.94 g, 11.0 mmol), and potassium carbonate (2.76 g, 20.0 mmol) in DMF (20 mL) was heated at 80° C. for 3 h. The mixture was cooled to rt, diluted with water (100 mL), and extracted with ethyl acetate (100 mL×3). The organic extracts were combined, washed with brine (50 mL×2), dried over anhydrous sodium sulfate, and concentrated. The residue was purified by silica gel column chromatography (petroleum ether/ethyl acetate=300:1 to 200:1) to give 1-(5-bromo-2-nitrophenyl)piperidine (2.2 g, 77% yield) as yellow solid. $^1$H NMR (CDCl3, 400 MHz) δ: 7.66 (d, J=8.8 Hz, 1H), 7.23 (s, 1H), 7.05 (d, J=8.4 Hz, 1H), 3.03 (m, 4H), 1.71 (m, 4H), 1.62 (m, 2H).

Step 2: Synthesis of 1-(2-Nitro-5-(4,4,5,5-tetramethyl-1,3,2-dioxaborolan-2-yl)phenyl)piperidine

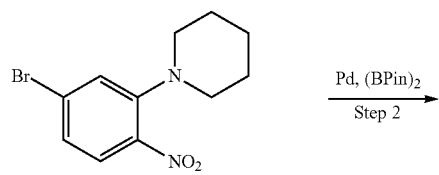

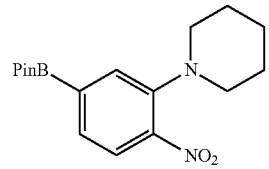

A mixture of 1-(5-bromo-2-nitrophenyl)piperidine (2.2 g, 7.8 mmol), 4,4,4',4',5,5,5',5'-octamethyl-2,2'-bi(1,3,2-dioxaborolane) (1.97 g, 7.8 mmol), potassium acetate (2.23 g, 23.3 mmol), and PdCl$_2$(dppf) (0.63 g, 0.8 mmol) in dioxane (100 mL) was refluxed overnight. The mixture was cooled to rt, diluted with water (200 mL), and extracted with ethyl acetate (200 mL×3). The organic extracts were combined, washed with brine (50 mL×2), dried over anhydrous sodium sulfate, and concentrate. The residue was purified by silica gel column chromatography (petroleum ether/ethyl acetate=100:1 to 20:1) to give 1-(2-nitro-5-(4,4,5,5-tetramethyl-1,3,2-dioxaborolan-2-yl)phenyl)piperidine (1.1 g, 43% yield). Pos. LC-MS: 333.22 (M+H)$^+$, C$_{17}$H$_{25}$BN$_2$O$_4$.

Step 3: Synthesis of 1-(5-((4-chloro-3-(trifluoromethyl)phenyl)sulfonyl)-2-nitrophenyl)piperidine

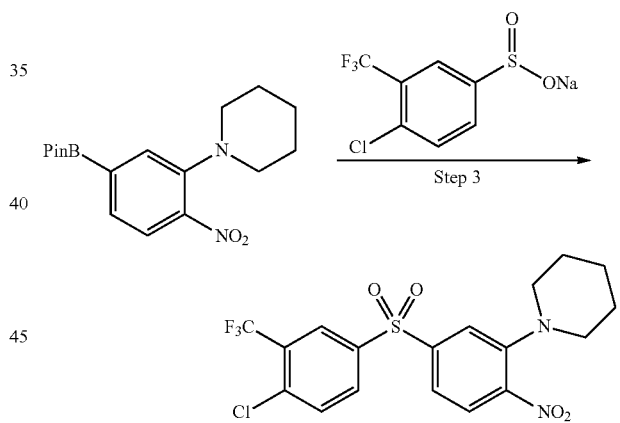

Potassium carbonate (828 mg, 6.0 mmol), 4 Å MS (2 g), and Cu(OAc)$_2$ (610 mg, 3.3 mmol) were added successively to a solution of compound 2 (1 g, 3.0 mmol) and sodium 4-chloro-3-(trifluoromethyl)benzenesulfinate (1.46 g, 6.0 mmol) in DMSO (25 mL). The reaction was stirred overnight at 60° C. in the presence of an oxygen balloon. The reaction mixture was poured into water (100 mL) and extracted with ethyl acetate (100 mL×3). The organic extracts were combined, washed with brine (50 mL×2), dried over anhydrous sodium sulfate, and concentrated. The residue was purified by silica gel column chromatography (petroleum ether/ethyl acetate=200:1 to 80:1) to 1-(5-((4-chloro-3-(trifluoromethyl)phenyl)sulfonyl)-2-nitrophenyl)piperidine (110 mg, 8% yield).

Step 4: Synthesis of 4-(4-Chloro-3-(trifluoromethyl)phenylsulfonyl)-2-(piperidin-1-yl)aniline

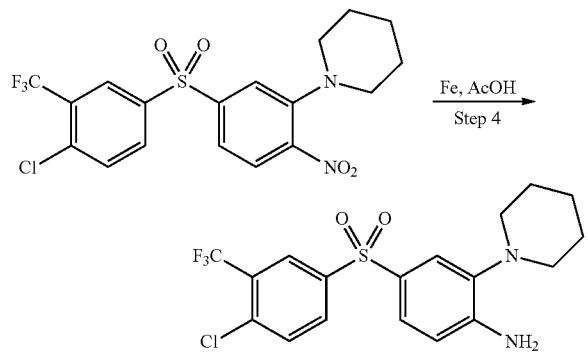

1-(5-((4-chloro-3-(trifluoromethyl)phenyl)sulfonyl)-2-nitrophenyl)piperidine (110 mg, 0.24 mmol) was dissolved in acetic acid (10 mL) and Fe (137 mg, 2.4 mmol) was added. The reaction was heated at 60° C. for 2 h. The mixture was cooled to rt, diluted with ethyl acetate (30 mL), filtered, and the cake was washed with ethyl acetate (10 mL). The filtrate and wash were washed with brine (20 mL). The organic extract was concentrated and the residue was purified by silica gel column chromatography (petroleum ether/ethyl acetate=100:1 to 50:1) to give 4-(4-Chloro-3-(trifluoromethyl)phenylsulfonyl)-2-(piperidin-1-yl)aniline (100 mg, quantitative yield). LC-MS: 418.76 (M+H)$^+$, $C_{18}H_{18}ClF_3N_2O_2S$.

Step 5: Synthesis of 1-(5-(4-Chloro-3-(trifluoromethyl)phenylsulfonyl)-2-isothiocyanatophenyl)piperidine

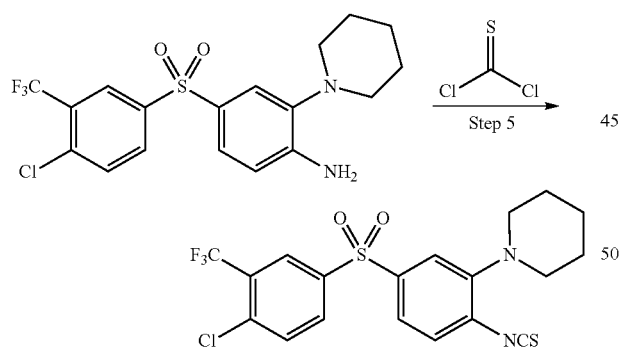

Thiophosgene (30 mg, 0.26 mmol) was added to a mixture of 4-(4-Chloro-3-(trifluoromethyl)phenylsulfonyl)-2-(piperidin-1-yl)aniline (100 mg, 0.24 mmol) and sat. sodium bicarbonate-water solution (10 mL) in chloroform (10 mL). The reaction was stirred for 2 h at rt under nitrogen protection. The mixture was extracted with dichloromethane (10 mL×2). The organic extracts were combined, washed with brine (10 mL), dried over anhydrous sodium sulfate, and concentrated to afford crude 1-(5-(4-(4-Chloro-3-(trifluoromethyl)phenylsulfonyl)-2-isothiocyanatophenyl)piperidine (80 mg, 67% yield), which was used for next reaction without further purification.

Step 6: Synthesis of 4-(4-((4-chloro-3-(trifluoromethyl)phenyl)sulfonyl)-2-(piperidin-1-yl)phenyl)-2,4-dihydro-3H-1,2,4-triazole-3-thione

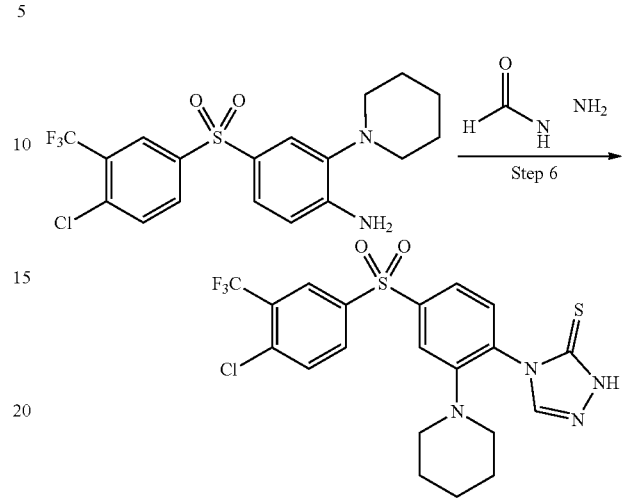

A solution of 1-(5-(4-chloro-3-(trifluoromethyl)phenylsulfonyl)-2-isothiocyanatophenyl)piperidine (80 mg, 0.17 mmol) and formohydrazide (10 mg, 0.17 mmol) in ethanol (10 mL) was refluxed for 30 min. The solvent was removed and the residue was dissolve in 2% NaOH. The reaction was heated at 100° C. for another 2 h. The mixture was cooled to rt and acidified to pH=3-4 by HCl. The resulting precipitate was extracted with dichloromethane for two times. The organic extracts were combined, washed with brine, dried over anhydrous sodium sulfate, and concentrated. The residue was re-crystallized in ethanol to give desired 4-(4-((4-chloro-3-(trifluoromethyl)phenyl)sulfonyl)-2-(piperidin-1-yl)phenyl)-2,4-dihydro-3H-1,2,4-triazole-3-thione (27 mg, 31% yield) as off-white solid. Pos. LC-MS: 502.88 (M+H)$^+$, $C_{20}H_{18}ClF_3N_4O_2S_2$. $^1$H NMR (DMSO-d6, 400 MHz) δ: 14.01 (br, 1H), 8.64 (s, 1H), 8.42 (m, 2H), 8.04 (d, J=8.0 Hz, 1H), 7.84 (d, J=8.4 Hz, 1H), 7.77 (s, 1H), 7.67 (d, J=8.4 Hz, 1H), 2.77 (m, 4H), 1.44 (m, 6H).

Example 10: 4-(4-(4-chloro-3-(trifluoromethyl)phenylsulfonyl)-2-(diethylamino)phenyl)-1H-1,2,4-triazole-5(4H)-thione (Compound 21)

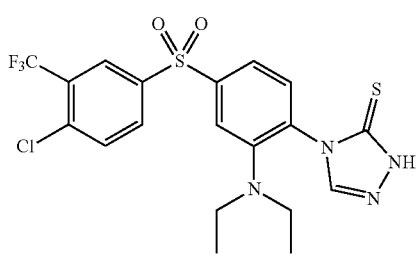 [SMILES: CCN(CC)c1cc(S(=O)(=O)c2ccc(Cl)c(C(F)(F)F)c2)ccc1-n1cn[nH]c1=S]

4-(4-(4-Chloro-3-trifluoromethyl)phenylsulfonyl)-2-(diethylamino)phenyl)-1H-1,2,4-triazole-5(4H)-thione was synthesized in a similar manner as described for 4-(4-((4-chloro-3-(trifluoromethyl)phenyl)sulfonyl)-2-(piperidin-1-yl)phenyl)-2,4-dihydro-3H-1,2,4-triazole-3-thione. Yield for Step 6: 12%, off-white solid. LC-MS: 489.0 (M−H)$^-$, $C_{19}H_{18}ClF_3N_4O_2S_2$. $^1$H NMR (DMSO-d6, 300 MHz) δ:

14.01 (br, 1H), 8.47 (s, 1H), 8.39 (m, 2H), 8.05 (m, 1H), 7.77 (m, 2H), 7.62 (m, 1H), 2.93 (m, 4H), 0.84 (t, J=6.75 Hz, 6H).

In certain instances, the above processes further involving the step of forming a salt of a compound of the present disclosure. Embodiments are directed to the other processes described herein; and to the product prepared by any of the processes described herein.

In certain instances, the above processes further involving the step of forming a salt, including a pharmaceutically acceptable salt, of a compound of the present disclosure. Salt forms may be prepared using standard salt formation procedures known in the art. Embodiments are directed to the other processes described herein; and to the product prepared by any of the processes described herein.

Example 11: Spray Dry Formulations

Formulations of Compound 1 were prepared using spray dry methods. Four spray solutions containing different polymers at a 3:1 polymer:compound ratio were prepared and sprayed onto a Buchi B-290 lab scale spray dryer. A summary of the spray parameters and results is shown in Table 1.

TABLE 1

| SDD # | Polymer: Compound | % solids | Approx. Flow Rate (g/min) | Average Outlet Temperature (° C.) | Total Spray Time (min) | Yield |
|---|---|---|---|---|---|---|
| 1 | 3:1 PVP-VA 64: Cmpd 1 | 15% | 8 | 40 | 11 | 90.2% |
| 2 | 3:1 Kollidon 30: Cmpd 1 | 15% | 8 | 41 | 11 | 87.7% |
| 3 | 3:1 HPMC E5: Cmpd 1 | 10% | 8-10 | 40 | 14 | 76.5% |
| 4 | 3:1 HPMC-AS: Cmpd 1 | 10% | 8 | 39 | 18 | 77.4% |

A 80:20 DCM:methanol solution was used as the spray solvent for all solutions. Spray solutions containing PVP-VA 64 and Kollidon 30 contained 15% w/w solid content, which includes both the content of the polymer and the compound. Spray solutions containing HPMC E5 and HPMC-AS contained 10% w/w solid content. A total amount of 3.1 g of Compound 1 was used for each spray run.

All spray dry dispersions (SDDs) were dried overnight at 40° C. at −25 mmHg vacuum, with a nitrogen purge for 15-20 minutes prior to removing from the oven for storage under a nitrogen blanket in the primary container, and desiccated in the secondary container.

The compounds and SDDs were visualized using Polarized Light Microscopy (PLM) and analyzed by powder X-Ray Diffraction (PXRD), Differential Scanning Calorimetry (DSC) and Thermogravimetric Analysis (TGA).

Figure 2A:
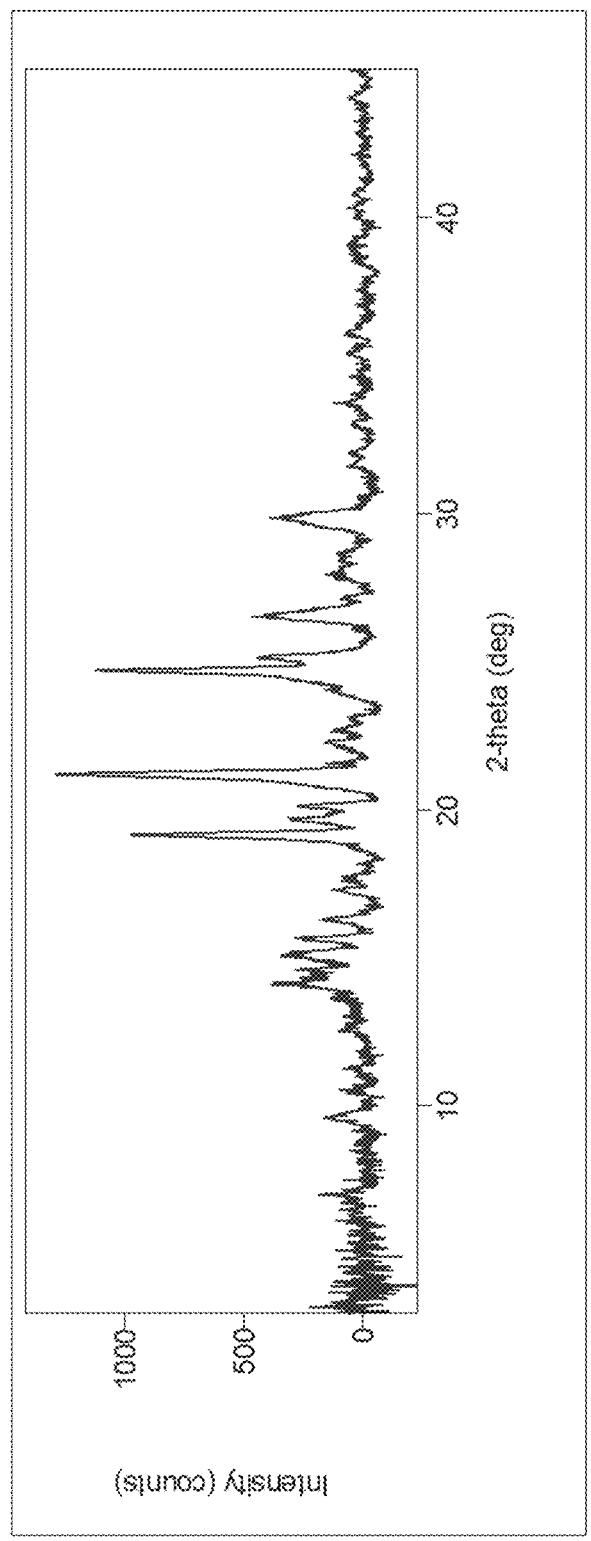
FIG. 2A shows the PXRD diffractogram of Compound 1.
Figure 2B:
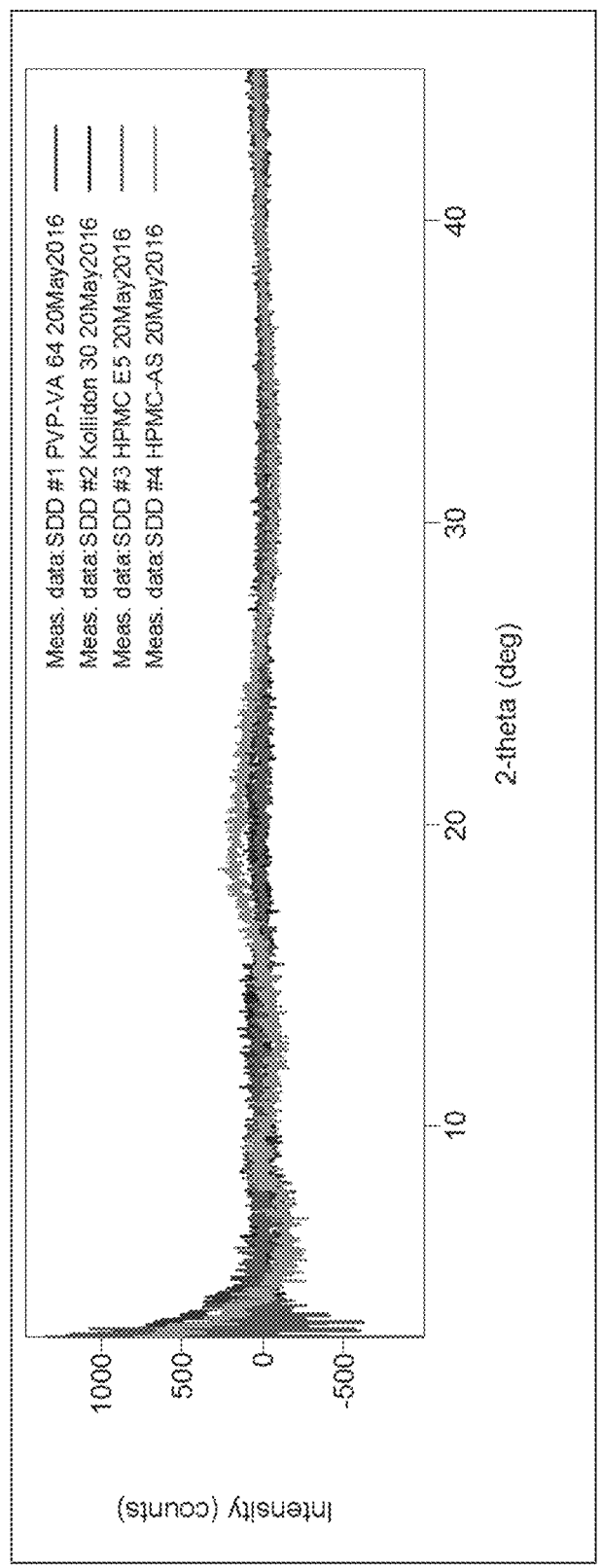
FIG. 2B shows the overlayed PXRD diffractogram of four different spray dried formulations of Compound 1.

PXRD was performed using a Rigaku X-Ray Powder Diffractometer (MiniFlex 600 FAE-R PDXL-Version 2-0 Cu Ku radiation S/N BD63000375). FIG. 2A shows the PXRD (Powder X-Ray Diffraction) diffractogram of Compound 1. The PXRD diffractogram for Compound 1 indicates that the compound is mostly crystalline due to its sharply defined peaks. FIG. 2B shows the overlayed PXRD diffractogram of four different spray dried formulations of Compound 1. The PXRD diffractogram for spray dry dispersions (SDD #1-4) indicate that the spray dry dispersions are mostly amorphous material.

Figure 3A:
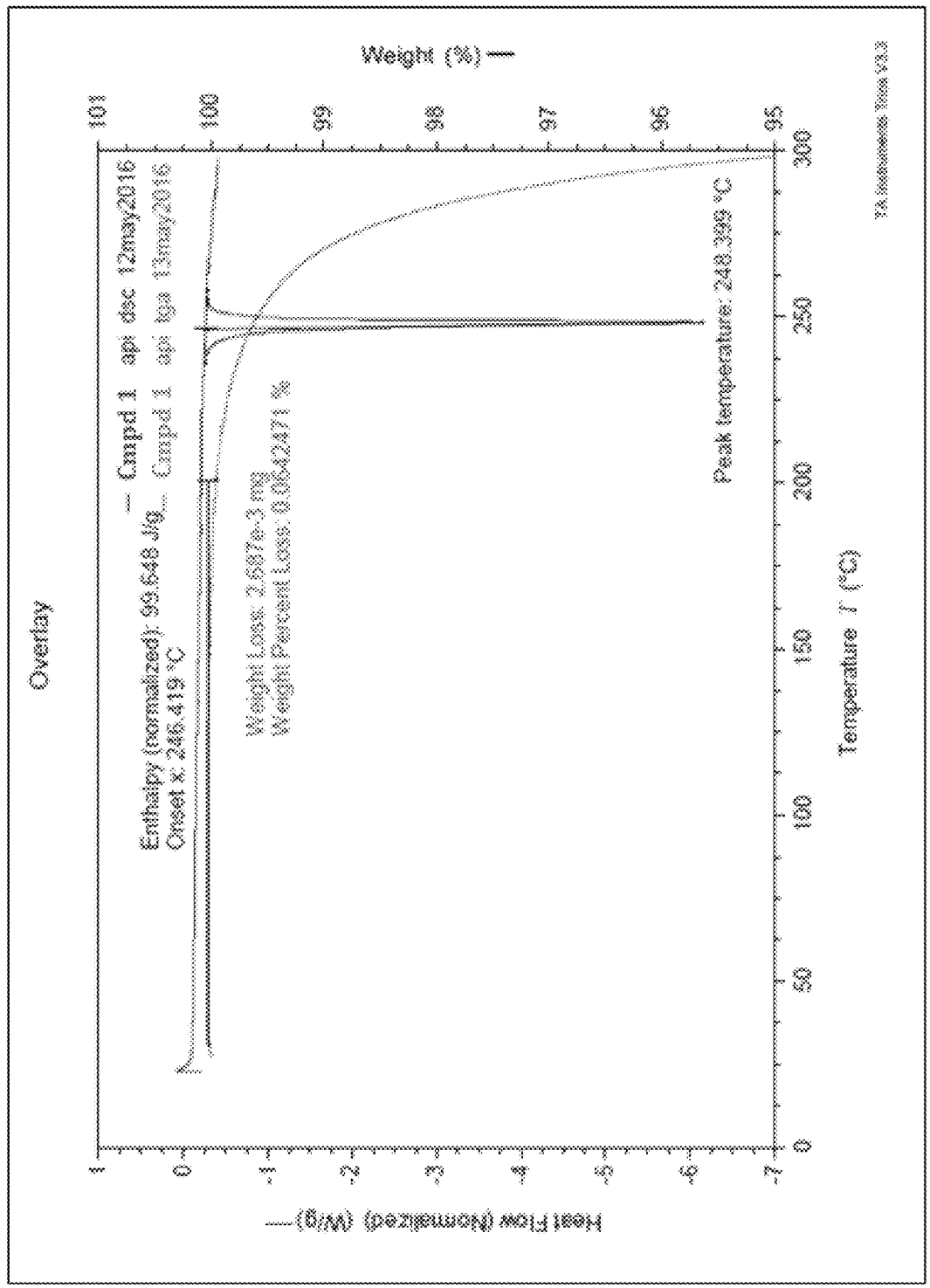
FIG. 3A shows the overlay of the DSC and TGA thermograms for Compound 1.
Figure 3B:
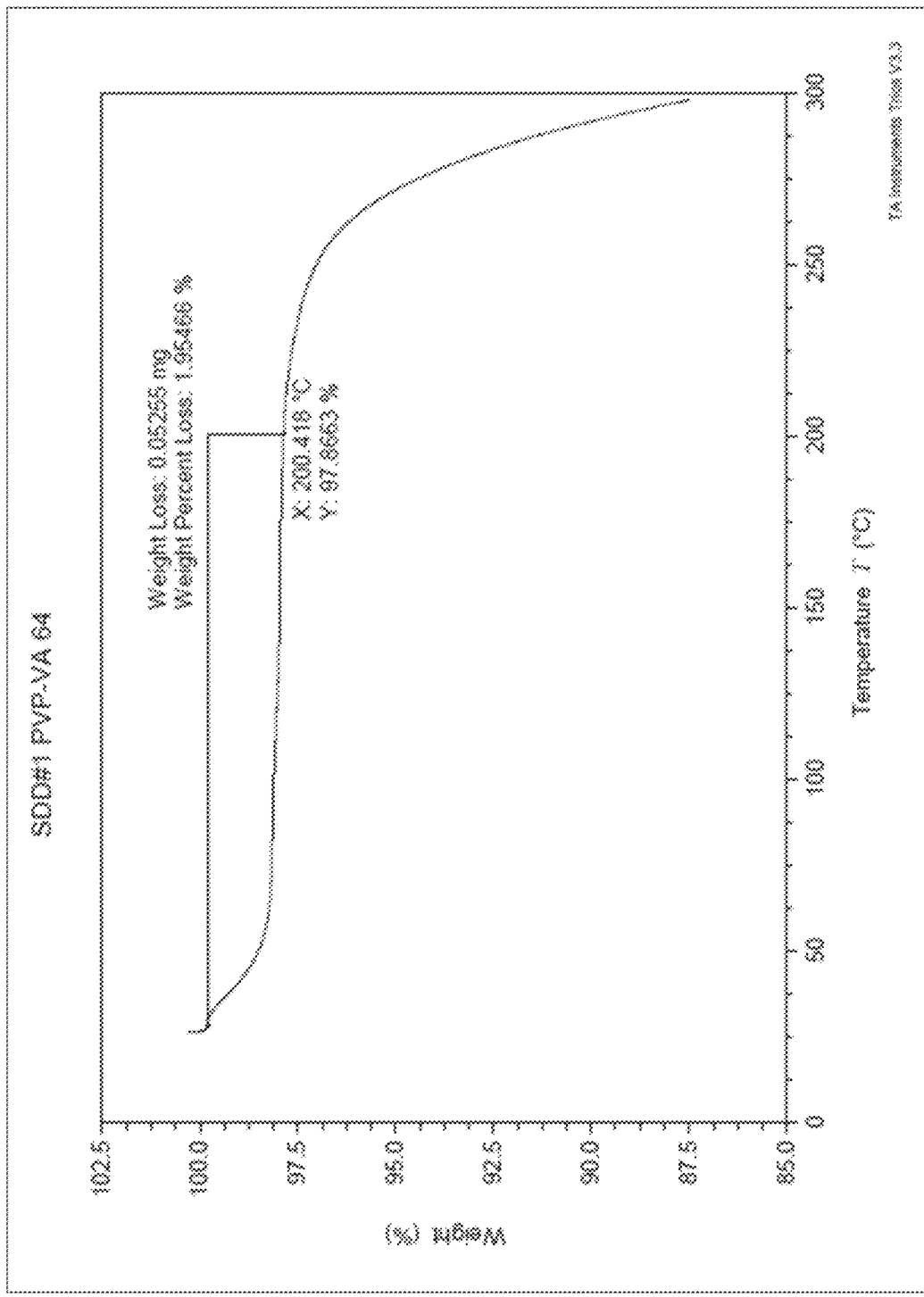
FIG. 3B and FIG. 3C show the TGA and DSC thermograms, respectively, for spray dry dispersion (SDD) #
Figure 3C:
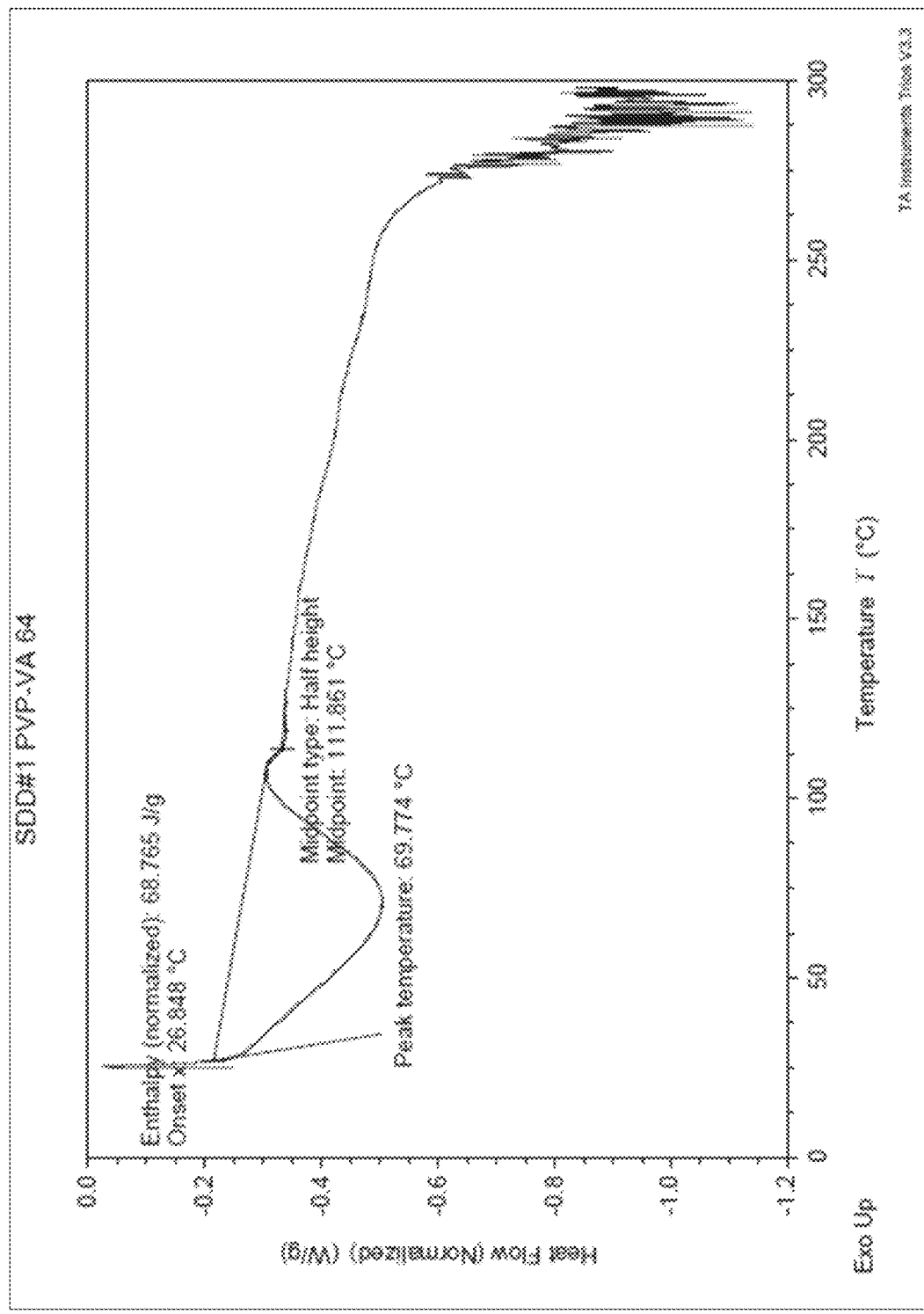
Figure 3D:
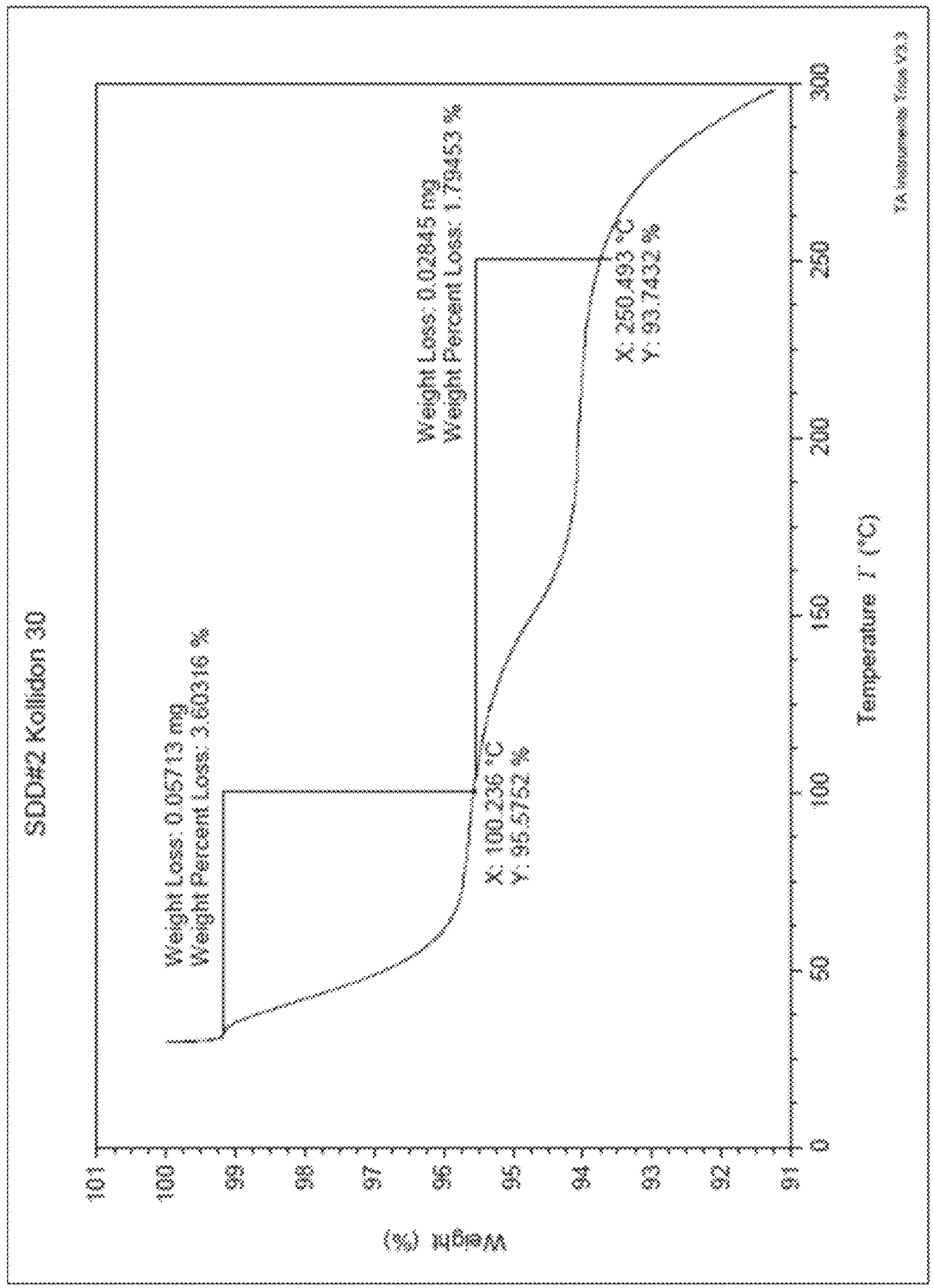
FIG. 3D and FIG. 3E show the TGA and DSC thermograms, respectively, for spray dry dispersion (SDD) #2.
Figure 3E:
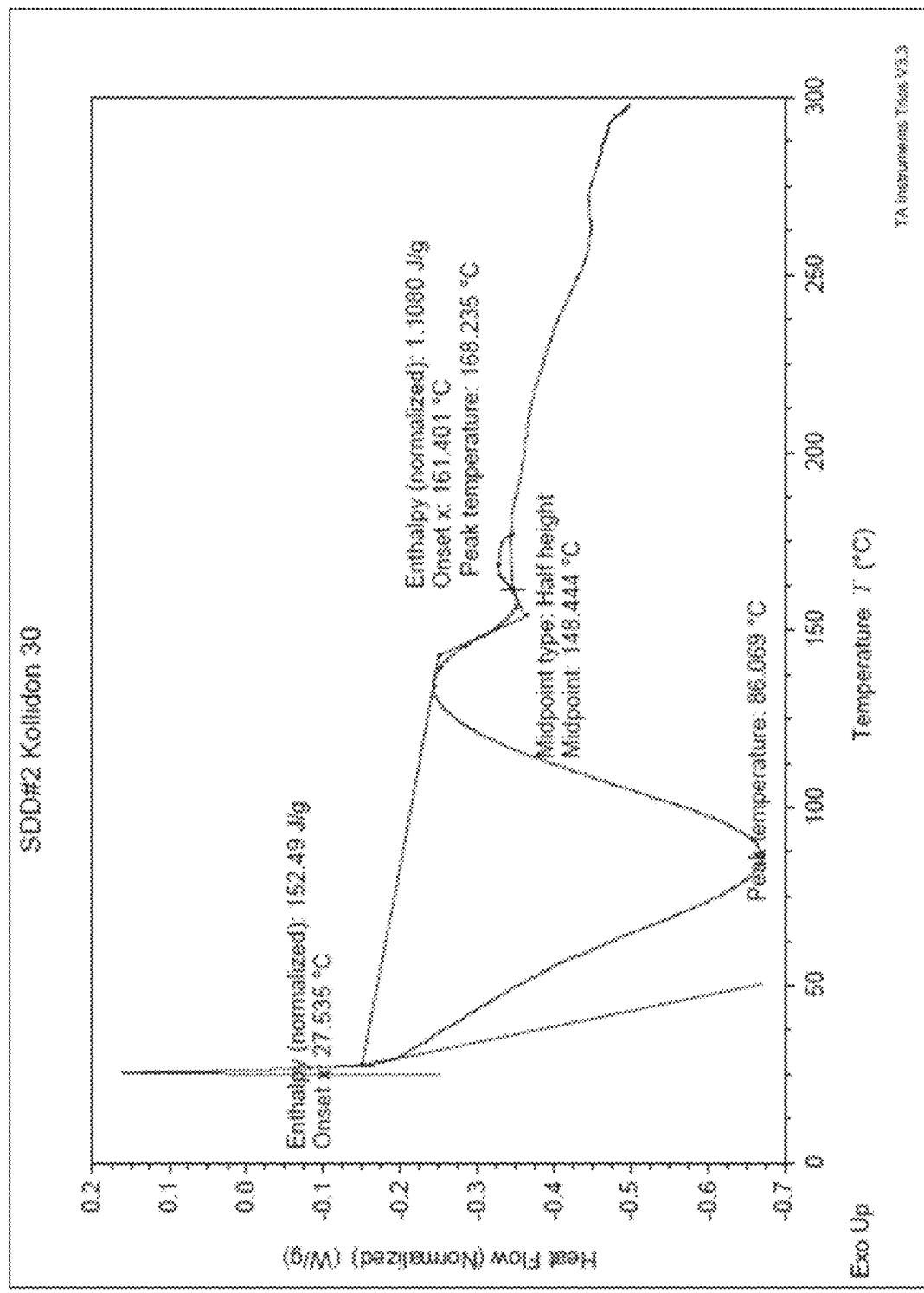
Figure 3F:
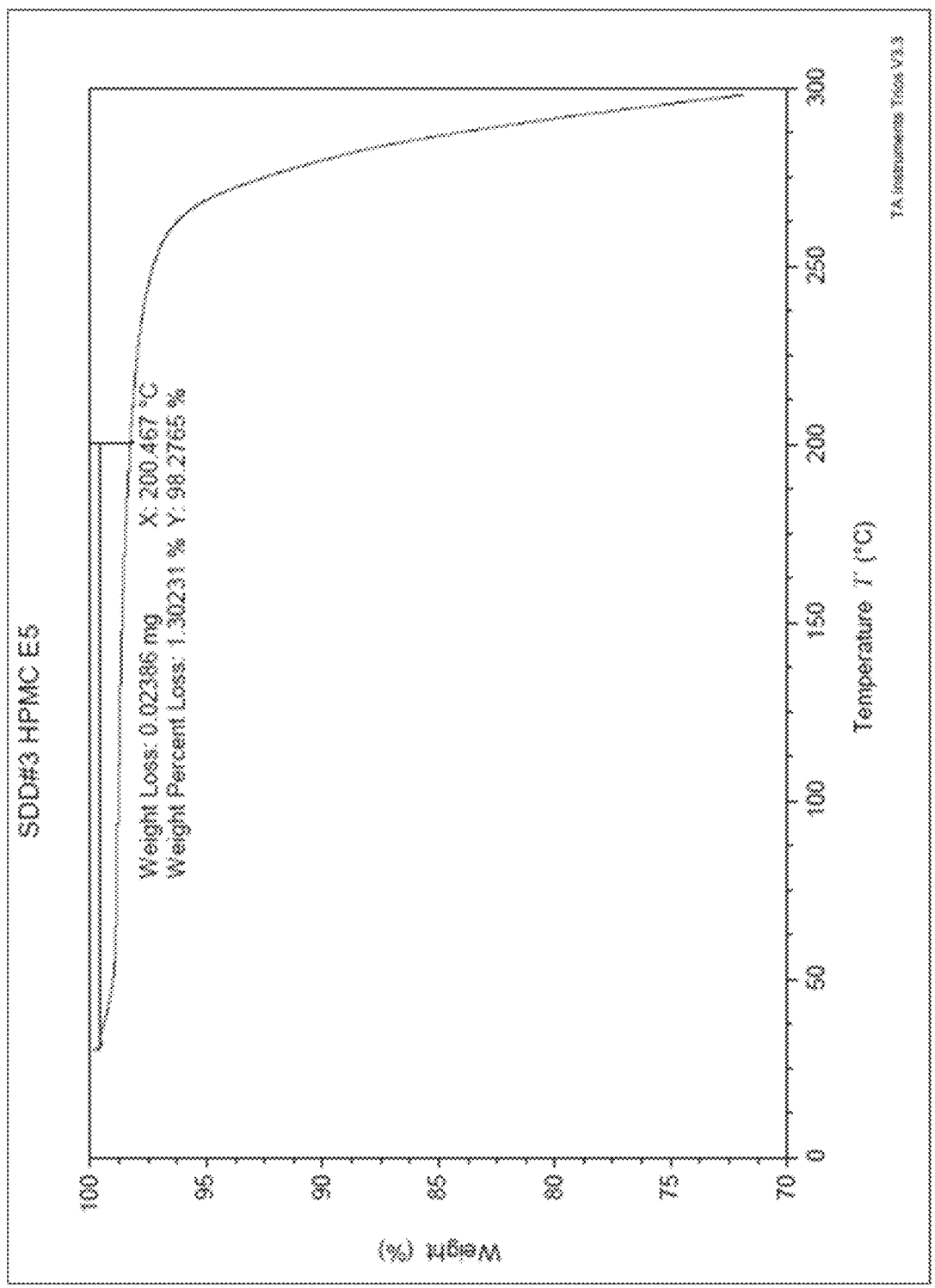
FIG. 3F and FIG. 3G show the TGA and DSC thermograms, respectively, for spray dry dispersion (SDD) #3.
Figure 3G:
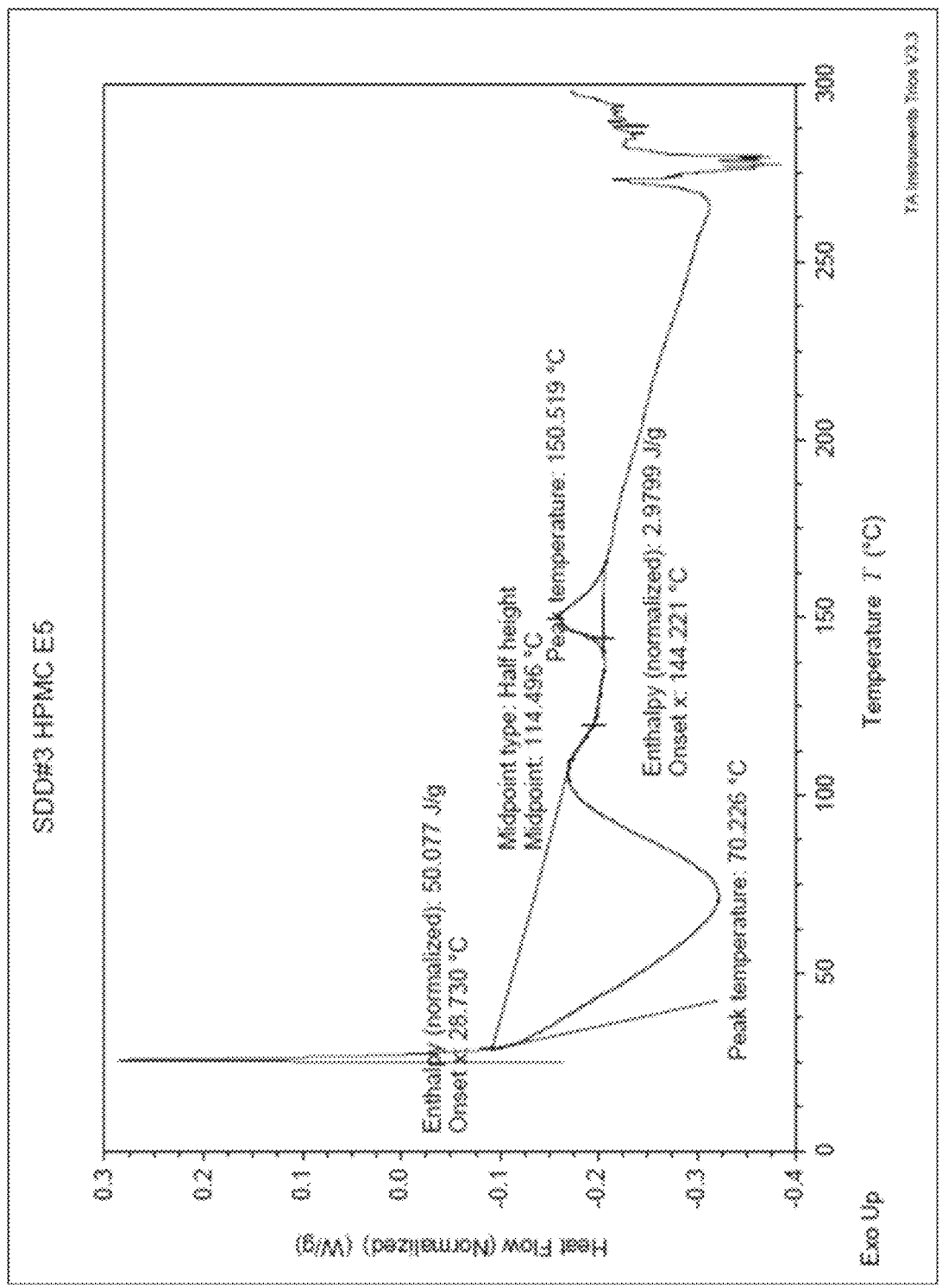
Figure 3H:
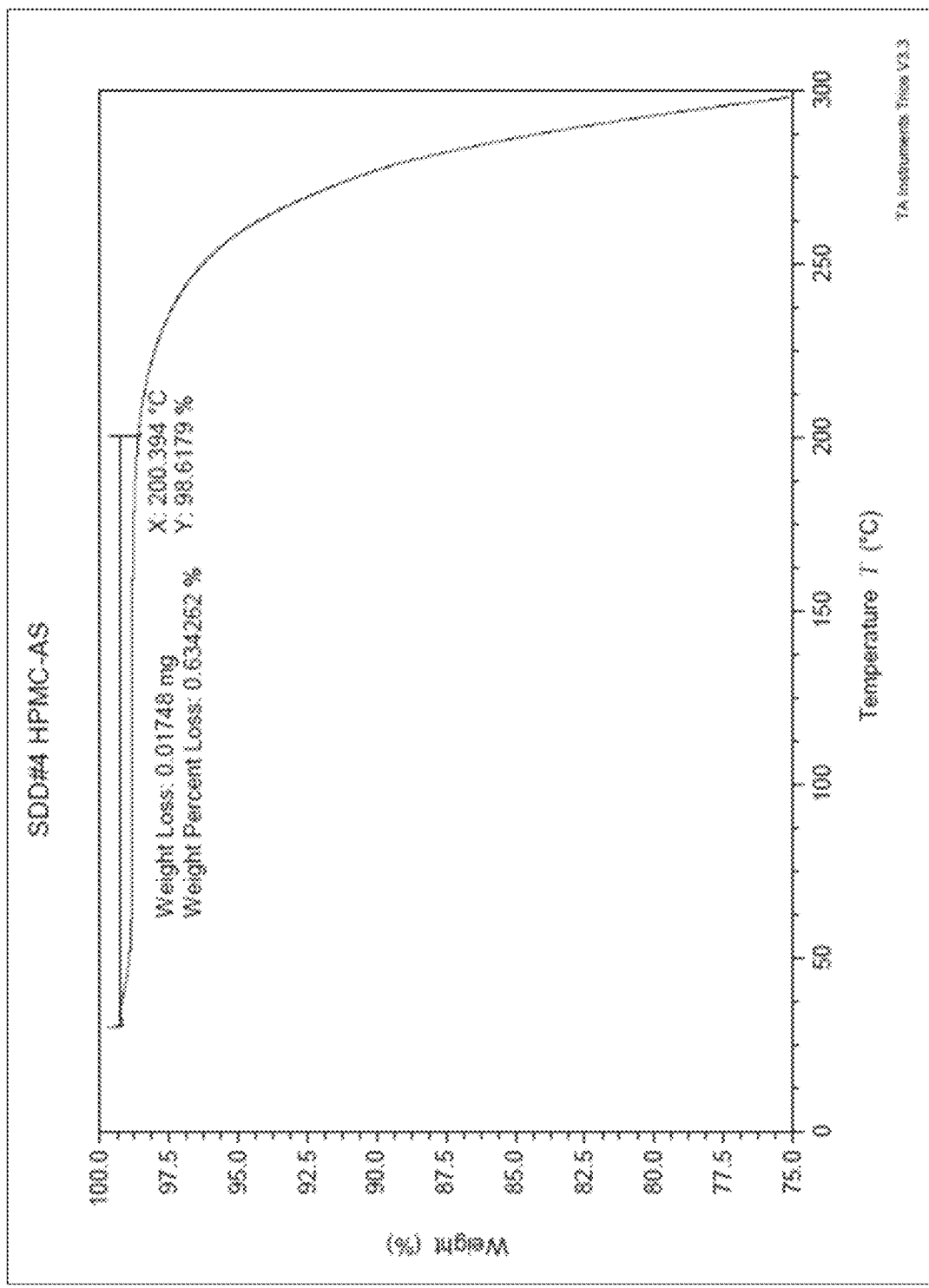
Figure 31:
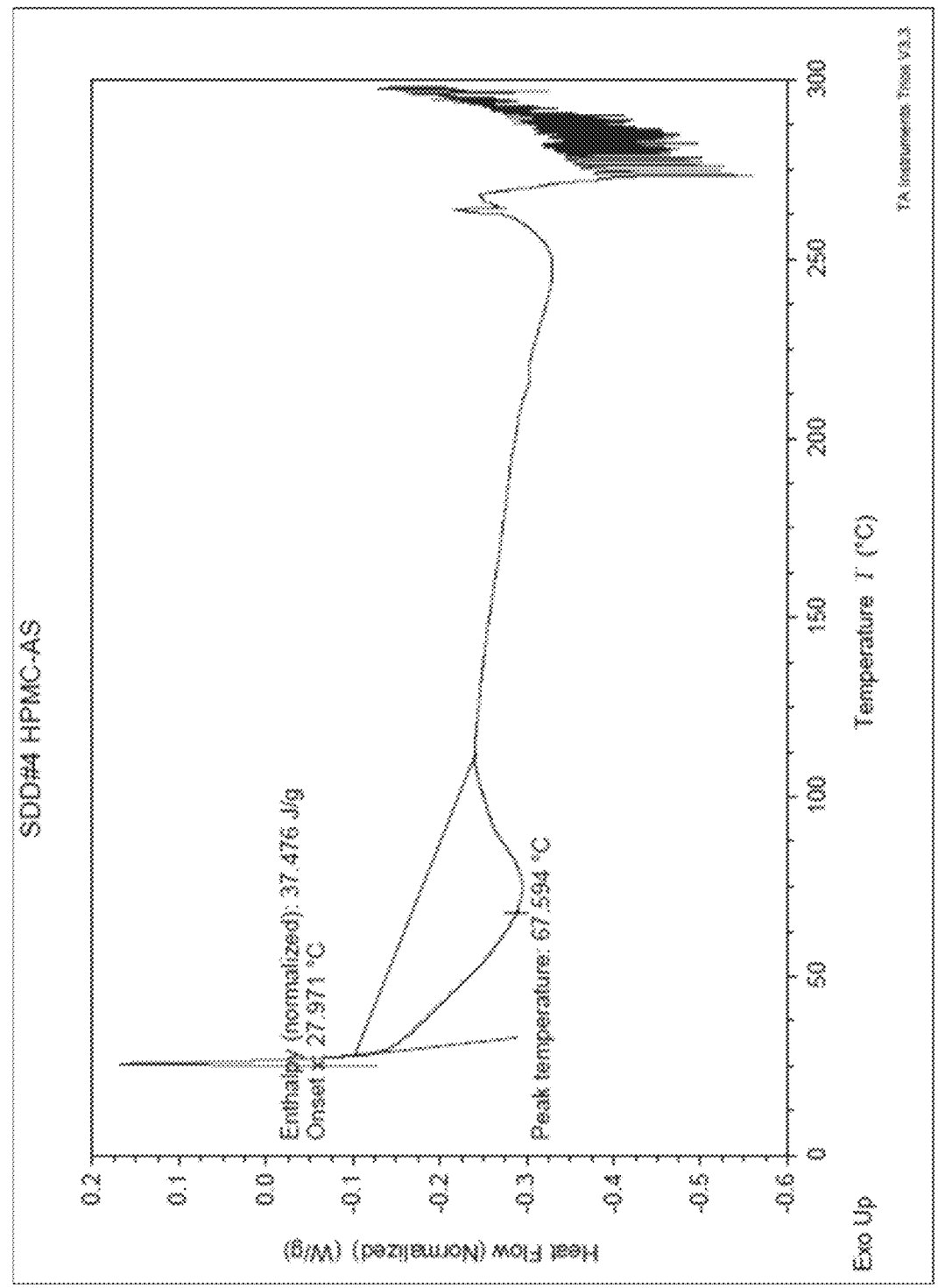

FIG. 3A shows the overlay of the DSC and TGA thermograms for Compound 1. FIGS. 3B, 3D, 3F, and 3H show the TGA thermographs of spray dry dispersions (SDD) #1-4, respectively. FIGS. 3C, 3E, 3G, and FIG. 3I show the DSC thermograms of spray dry dispersions (SDD) #1-4, respectively.

Figure 4A:
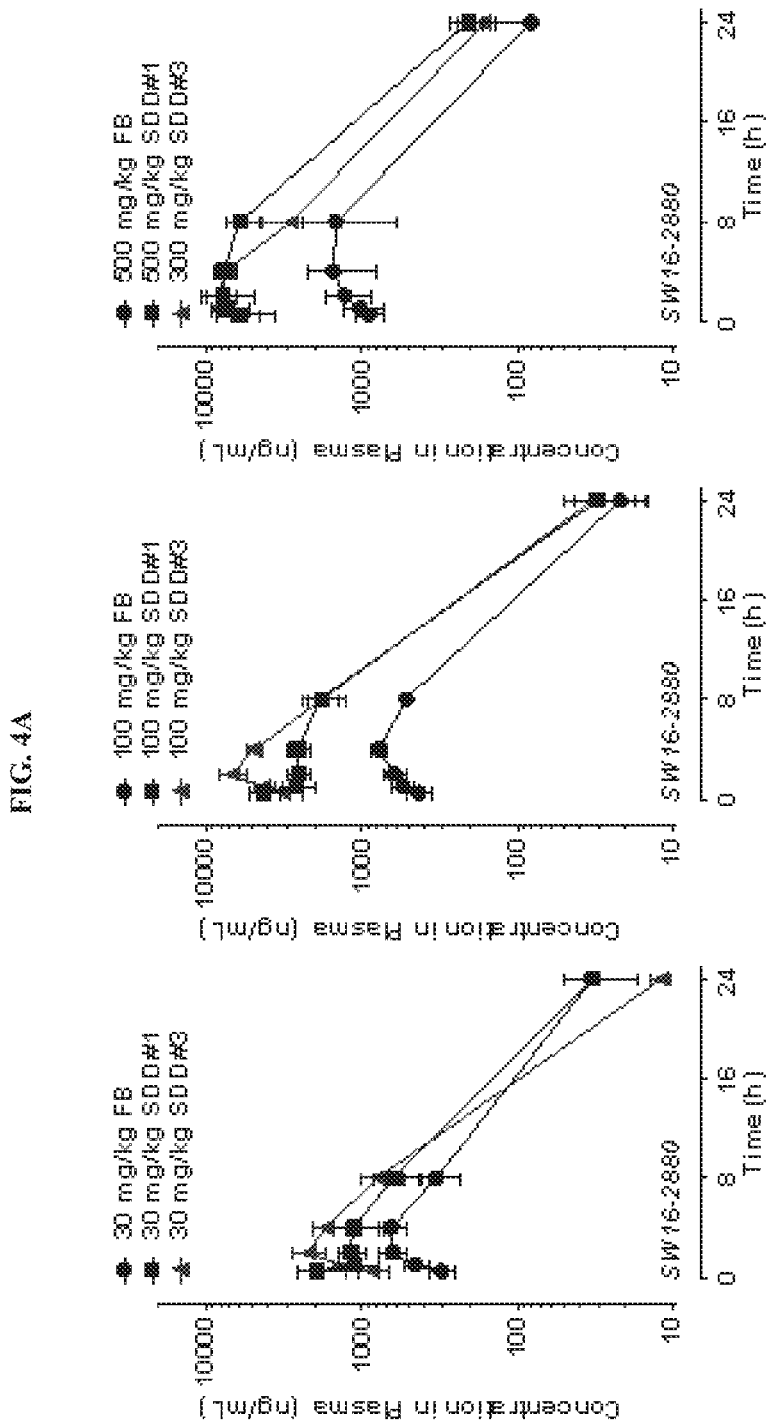
FIG. 4A shows the pharmacokinetic curves of Compound 1 in free base form (FB) and two spray dry dispersions of Compound 1 (SDD #1 and SDD #3).
Figure 4B:
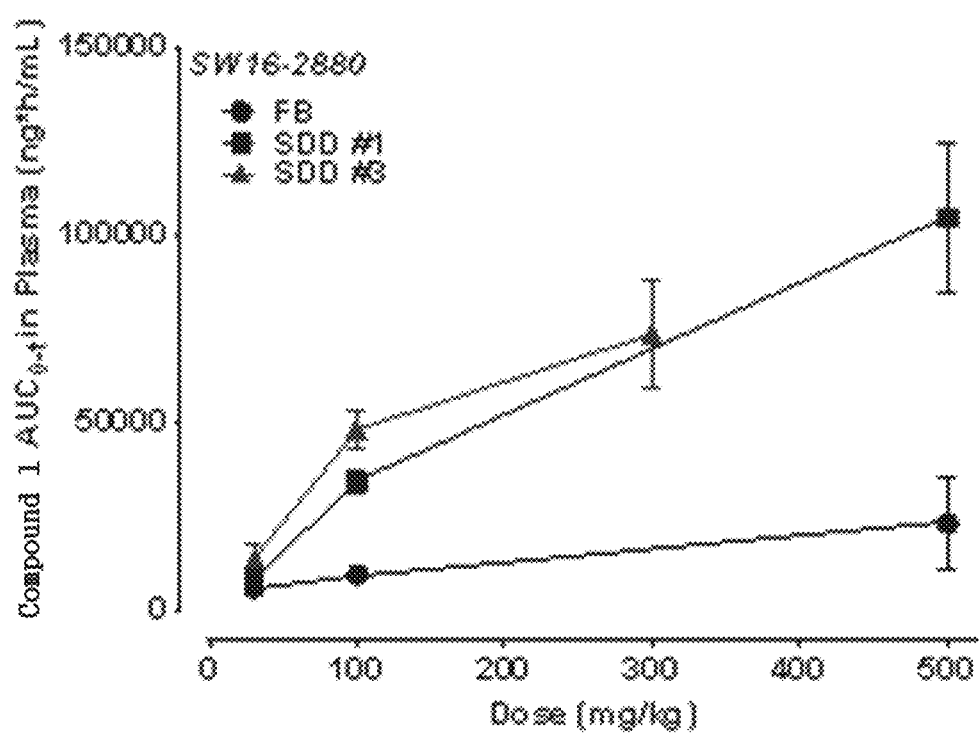
FIG. 4B shows the AUC vs. dose for Compound 1 in free base form (FB) and two spray dry dispersions of Compound 1 (SDD #1 and SDD #3).

The pharmacokinetic (PK) properties of three separate formulations of Compound 1 (Free Base and two spray dry dispersions, SDD #1 and SDD #3) were evaluated in male Sprague Dawley (CD®IGS) rats following a single administration by oral (PO) gavage of 30, 100 or 500 mg/kg at a volume of 10 mL/kg. A total of 45 animals were used in this study (5 rats/dose×3 dose levels×3 formulations). The vehicle consisted of 0.75% hydroxypropyl methylcellulose (HPMC; w/v), 0.2% Tween 20 (v/v), and deionized water. FIG. 4A shows the PK curves of Compound 1 in free base form (FB) and two spray dry dispersions of Compound 1 (SDD #1 and SDD #3). FIG. 4B shows the AUC vs. dose for Compound 1 in free base form (FB) and two spray dry dispersions of Compound 1 (SDD #1 and SDD #3).

Example 12. Single Crystal X-Ray Diffraction

Single crystal x-ray diffraction (SXRD) was carried out (Solid Form Solutions, Penicuik, Scotland, UK) to determine the structure of Compound 1, and the results are summarized in Tables 2 and 3. Single crystal X-ray analysis was conducted using an Agilent SuperNova dual source instrument, at 120 K using Mo Ku radiation ($\lambda$=0.71073 A) generated by a sealed tube. Data was corrected for absorption effects using an empirical correction with spherical harmonics. All data was reduced, solved and refined in the achiral triclinic space group P-1.

Compound 1 (approx. 10 mg) was dissolved in isopropyl acetate (500 µL) in a 2 ml clear glass HPLC vial and heptane slowly diffused into the solution of Compound 1 at ambient temperature. After standing at ambient temperature for several days, large block-like crystals were noted to have grown below the solution meniscus, that were suitable for interrogation by single crystal X-ray diffraction.

A colorless fragment of a lath (0.237×0.158×0.126 mm) was used in the single crystal diffraction study. The crystal was coated with Paratone oil and data collected on a Rigaku Oxford Diffraction (Dual Source) SuperNova diffractometer using graphite monochromated Mo Ku (k=0.71073 A, 40 kV/40 mA) radiation at 120(1) K using an Oxford Cryosystems 700+ low temperature device and Atlas CCD plate detector (Rigaku Oxford Diffraction). A total of 2123 frames were collected for a hemisphere of reflections using a ω strategy calculated by CrysAlisPro (Rigaku Oxford Diffraction 1.171.38.43 h, 2015) over the Θ range 3.02-31.25° with 1° step size and 20 sec/frame exposure. Frames were integrated using CrysAlisPro (Rigaku Oxford Diffraction 1.171.38.43 h, 2015) to a triclinic cell using a moving average background, yielding a total of 106625 reflections, of which 10259 were independent (I>2σ(I)). Data were integrated to 2Θ max=62.5° (95.4% completeness). Absorption corrections were applied using SCALE3 ABSPACK (CrysAlisPro 1.171.38.43 h, Rigaku Oxford Diffraction, 2015) using an empirical model using spherical harmonics coupled with gaussian integration over a multifaceted crystal model (absorption coefficient G=0.533 mm-1).

The OLEX2 (Dolomanov, O. V., Bourhis, L. J., Gildea, R. J., Howard, J. A. K., Puschmann, H. *J Appl. Cryst.* 2009, 42, 339-341) graphical software package was used as an interface for phase determination and structure refinement. Data were solved using Superflip (Palatinus, L. & Chapuis, G. (2007). J. Appl. Cryst., 40, 786-790; Palatinus, L. & van der Lee, A. (2008). J. Appl. Cryst. 41, 975-984; Palatinus, L., Prathapa, S. J. & van Smaalen, S. (2012). J. Appl. Cryst. 45, 575-580) and developed by full least squares refinement on F2 (Sheldrick, G. M. (2015). Acta Cryst. C71, 3-8) in the triclinic space-group P-1. A search for higher metric symmetry using the ADDSYMM (Le Page, Y. *J. Appl. Cryst.* 1987, 20, 264; Le Page, Y. *J. Appl. Cryst.* 1988, 21, 983) routine of PLATON (Spek A. L., *Acta Cryst.* 2009, D65, 148) was attempted, but failed to uncover any higher order symmetry. All non-hydrogen atoms were located in the Fourier map and their positions refined prior to describing their thermal movement of all non-hydrogen atoms anisotropically. Within the asymmetric unit, two complete, crystallographically independent Compound 1 formula units were found, where one of which (molecule 'B') was found to exhibit positional disorder over three positions. This disorder was refined using the SHELX compatible SUMP command with three parts to yield occupancies of 34.1:43.2:22.7%. Furthermore, the disorderedrings C11B(C12B, C13B,C14B,C9B,C10B); C11C(C15D,C13C,C14C,C9C, C10C); C11D(C12D,C13D, C14D,C9D,C10D) were refined as rigid hexagons using the SHELX compatible command AFIX66. Furthermore, C15B-C13B was restrained to 1.49 (2) A and C9B, C9D and C13D were restrained to give approximate isotropic thermal motion using the SHELX compatible command ISOR with sigma 0.01 and sigma 0.05 for terminal atoms. All hydrogen atoms were placed in calculated positions using a riding model with fixed Uiso at 1.2 times for all CH and NH groups. Highest peak: 0.76 e.A-3 at 0.1943 0.1800 0.0797 [0.42 A from S1B]. Deepest hole: −1.18 e.A-3 at 0.2203 0.1543 0.1130 [0.86 A from SIB].

Crystal Data for $C_{15}H_9ClF_3N_3O_2S_2$ (M=419.82 g/mol): triclinic, space group P-1 (no. 2), a=10.0426 (2) A, b=12.6946(3) A, c=13.5882(3) A, α=89.219(2°), β=83.540 (2°), γ=73.357(2°), V=1648.89(6) A3, Z=4, T=120(1) K, μ(MoKα)=0.533 mm-1, Dcalc=1.691 g/cm³, 106625 reflections measured (6.04°≤2Θ≤62.5°), 10259 unique (Rint=0.0431, Rsigma=0.0252) which were used in all calculations. The final $R_1$ was 0.0700 (>2sigma(I)) and $wR_2$ was 0.1358 (all data).

Figure 5A:
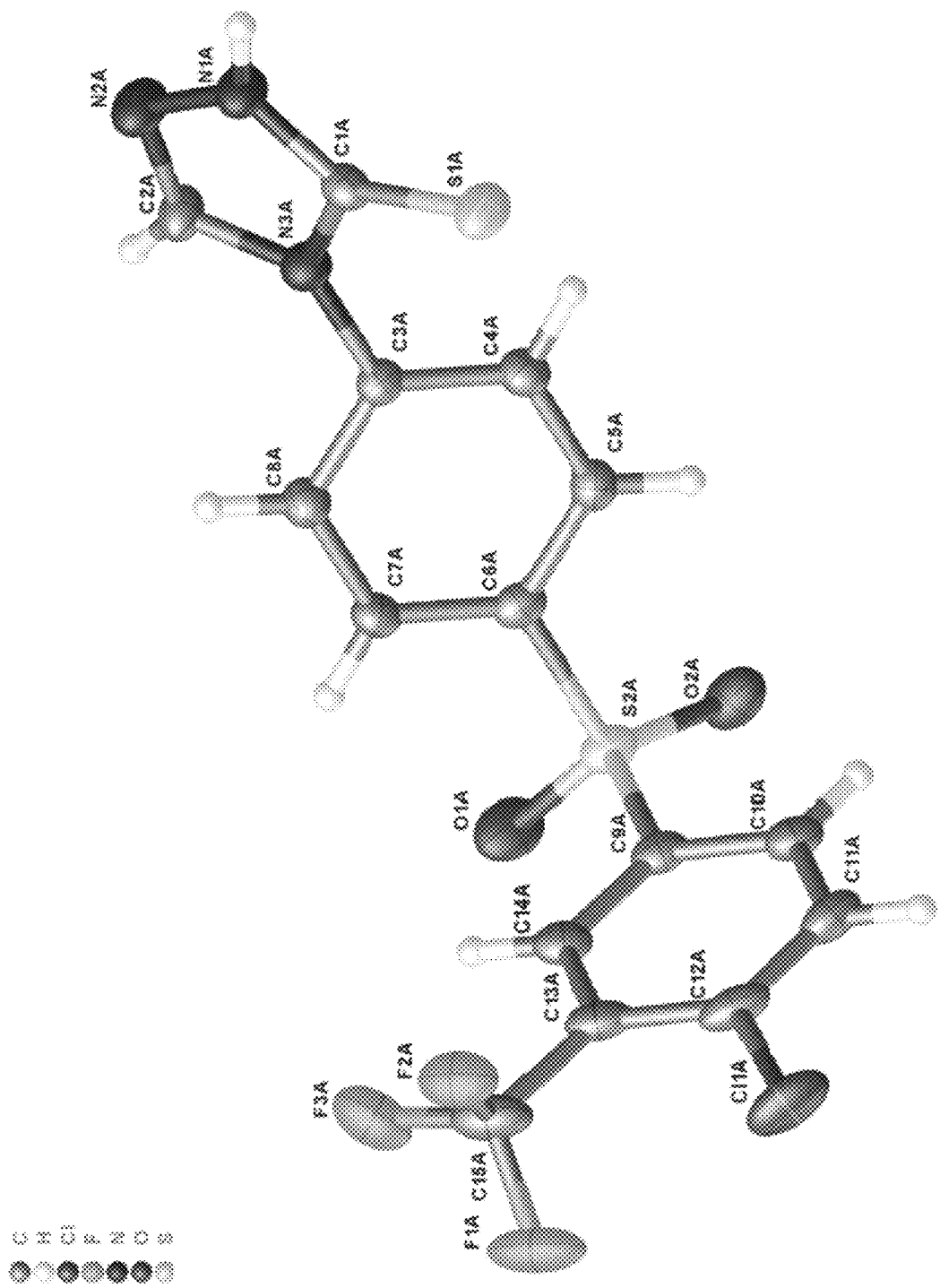
FIG. 5A shows the single crystal structural analysis of Compound 1 (4-(4-((4-chloro-3-(trifluoromethyl)phenyl) sulfonyl)phenyl)-2,4-dihydro-3H-1,2,4-triazole-3-thione).
Figure 5B:
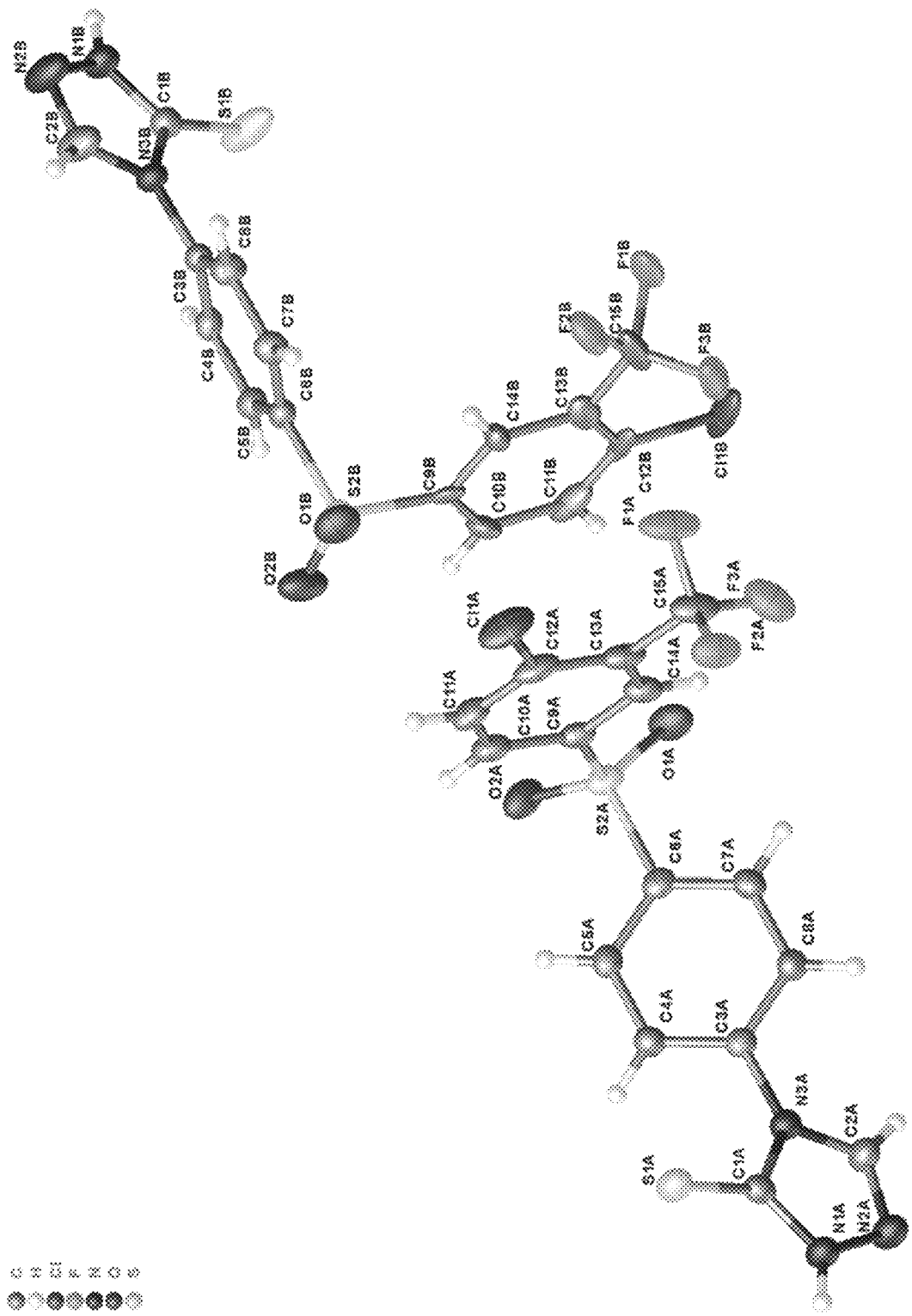
FIG. 5B shows the single crystal structural analysis of an asymmetric unit of Compound 1.

The single crystal structure analysis of Compound 1 is shown in FIG. 5A. FIG. 5B shows the single crystal structural analysis of an asymmetric unit of Compound 1. The asymmetric unit was found to contain two complete units of Compound 1 with 1-chloro-trifluorophenyl moiety of molecule 'B' refined occupancies of 34.1:43.2:22.7%. No further disorder was found within the overall model.

Table 2 shows the crystallographic refinement details of Compound 1 (Form 1).

TABLE 2

| Empirical formula | $C_{15}H_9ClF_3N_3O_2S_2$ |
|---|---|
| Formula weight | 419.82 |
| Temperature/K | 120(1) |
| Crystal system | triclinic |
| Space group | P-1 |
| a/Å | 10.0426(2) |
| b/Å | 12.6946(3) |
| c/Å | 13.5882(3) |
| α/° | 89.219(2) |
| β/° | 83.540(2) |
| γ/° | 73.357(2) |
| Volume/Å³ | 1648.89(6) |
| Z, Z' | 4 |
| $\rho_{calc}$ g/cm³ | 1.691 |
| μ/mm⁻¹ | 0.533 |
| F(000) | 848.0 |
| Crystal size/mm³ | 0.237 × 0.158 × 0.126 |

TABLE 2-continued

| Radiation | MoKα (λ = 0.71073) |
|---|---|
| 2Θ range for data collection/° | 6.04 to 62.5 |
| Index ranges | −14 ≤ h ≤ 14, −18 ≤ k ≤ 17, −19 ≤ l ≤19 |
| Reflections collected | 106625 |
| Independent reflections | 10259 [$R_{int}$ = 0.0431, $R_{sigma}$ = 0.0252] |
| Data/restraints/parameters | 10259/20/634 |
| S | 1.232 |
| Final R indexes [$F^2 > 2\sigma (F^2)$] | $R_1$ = 0.0700, $wR_2$ = 0.1327 |
| Final R indexes [all data] | $R_1$ = 0.0787, $wR_2$ = 0.1358 |
| Δρmax, Δρmin/e Å⁻³ | 0.76/−1.18 |

$$R_1 = (\Sigma |F_o| - |F_c|)/\Sigma |F_o|)$$
$$wR_2 = \{\Sigma [w(F_o^2 - F_c^2)^2]/\Sigma[w(F_o^2)^2]\}^{1/2}$$
$$S = \{\Sigma [w(F_o^2 - F_c^2)^2]/(n - p)\}^{1/2}$$

Figure 6:
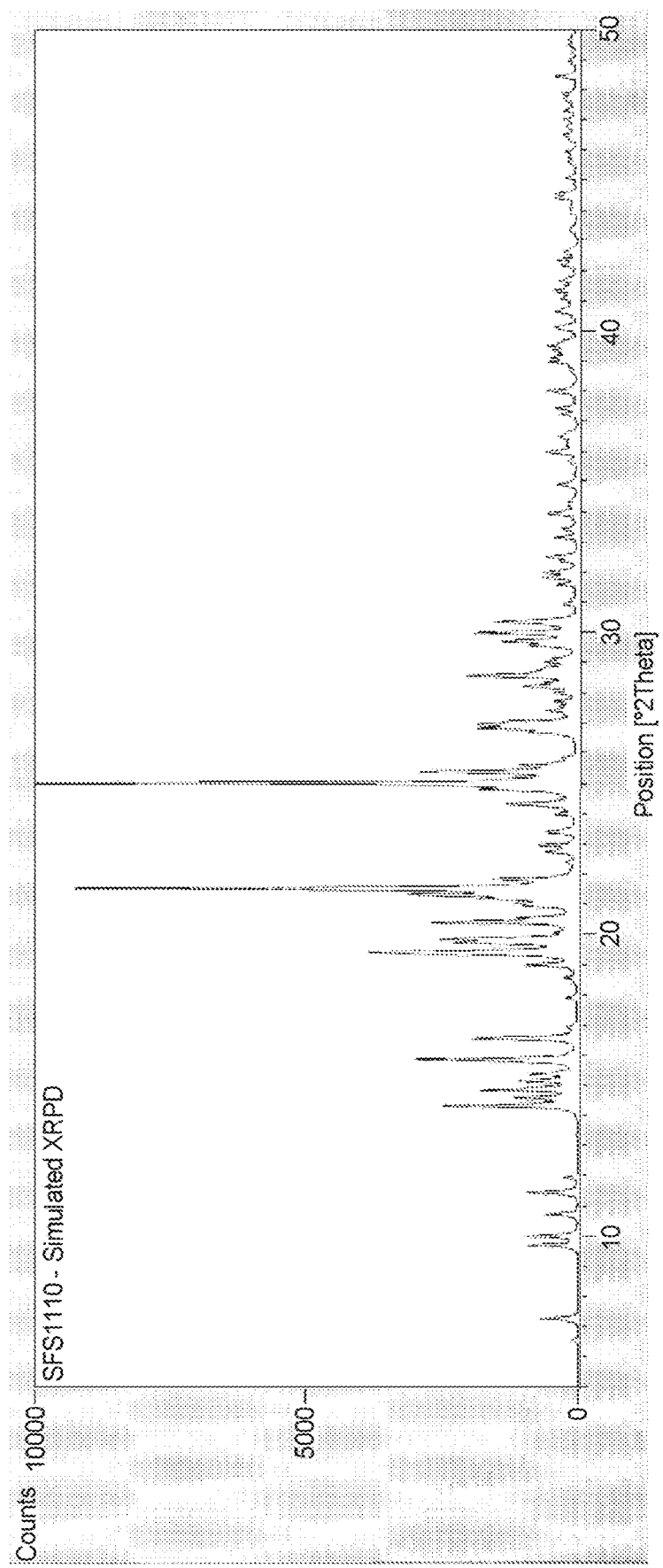
FIG. 6 shows the X-ray powder diffractogram (XRPD) of Compound 1.

Table 3 shows the simulated 2Θ X-ray powder diffractogram (XRPD) of Compound 1 (Form 1). The XRPD is shown in FIG. 6.

TABLE 3

| No. | Pos. [°2Th.] | FWHM [°2Th.] | Area [cts*°2Th.] | d-spacing [Å] | Height [cts] | Rel. Int. [%] |
|---|---|---|---|---|---|---|
| 1 | 7.2633 | 0.096 | 89.50 | 12.1610 | 699.26 | 6.94 |
| 2 | 9.6858 | 0.096 | 119.57 | 9.1242 | 934.16 | 9.27 |
| 3 | 9.9875 | 0.120 | 158.90 | 8.8492 | 993.15 | 9.85 |
| 4 | 10.7073 | 0.120 | 101.23 | 8.2559 | 632.68 | 6.28 |
| 5 | 11.4394 | 0.096 | 122.72 | 7.7291 | 958.77 | 9.51 |
| 6 | 11.9245 | 0.096 | 32.83 | 7.4157 | 256.50 | 2.54 |
| 7 | 14.3055 | 0.096 | 317.49 | 6.1864 | 2480.38 | 24.61 |
| 8 | 14.5557 | 0.096 | 149.08 | 6.0806 | 1164.67 | 11.55 |
| 9 | 14.8445 | 0.096 | 233.35 | 5.9630 | 1823.05 | 18.09 |
| 10 | 15.1296 | 0.120 | 174.44 | 5.8512 | 1090.27 | 10.82 |
| 11 | 15.3639 | 0.096 | 111.84 | 5.7625 | 873.74 | 8.67 |
| 12 | 15.8539 | 0.096 | 381.04 | 5.5855 | 2976.84 | 29.53 |
| 13 | 16.5457 | 0.096 | 250.15 | 5.3535 | 1954.28 | 19.39 |
| 14 | 18.9653 | 0.096 | 125.47 | 4.6756 | 980.23 | 9.72 |
| 15 | 19.3893 | 0.168 | 842.79 | 4.5743 | 3762.45 | 37.32 |
| 16 | 19.7223 | 0.072 | 219.15 | 4.4978 | 2282.80 | 22.65 |
| 17 | 19.8198 | 0.072 | 244.04 | 4.4759 | 2542.05 | 25.22 |
| 18 | 20.3840 | 0.096 | 347.46 | 4.3533 | 2714.51 | 26.93 |
| 19 | 20.5478 | 0.072 | 98.72 | 4.3189 | 1028.31 | 10.20 |
| 20 | 20.9792 | 0.144 | 197.96 | 4.2311 | 1031.04 | 10.23 |
| 21 | 21.3094 | 0.072 | 304.21 | 4.1663 | 3168.82 | 31.44 |
| 22 | 21.5096 | 0.120 | 1522.85 | 4.1279 | 9517.79 | 94.42 |
| 23 | 21.8210 | 0.096 | 200.37 | 4.0697 | 1565.37 | 15.53 |
| 24 | 22.7420 | 0.120 | 92.33 | 3.9070 | 577.05 | 5.72 |
| 25 | 22.9527 | 0.096 | 94.20 | 3.8716 | 735.93 | 7.30 |
| 26 | 23.3841 | 0.120 | 94.20 | 3.8011 | 588.74 | 5.84 |
| 27 | 24.3296 | 0.096 | 171.62 | 3.6555 | 1340.75 | 13.30 |
| 28 | 24.8115 | 0.072 | 167.72 | 3.5856 | 1747.10 | 17.33 |
| 29 | 25.0252 | 0.096 | 1290.30 | 3.5554 | 10080.44 | 100.00 |
| 30 | 25.3797 | 0.096 | 374.34 | 3.5066 | 2924.51 | 29.01 |
| 31 | 25.5790 | 0.072 | 103.60 | 3.4797 | 1079.11 | 10.71 |
| 32 | 26.6520 | 0.072 | 79.62 | 3.3420 | 829.39 | 8.23 |
| 33 | 26.8121 | 0.072 | 175.89 | 3.3224 | 1832.21 | 18.18 |
| 34 | 26.9266 | 0.072 | 180.08 | 3.3085 | 1875.81 | 18.61 |
| 35 | 27.4026 | 0.096 | 73.50 | 3.2521 | 574.20 | 5.70 |
| 36 | 27.9857 | 0.096 | 64.48 | 3.1857 | 503.75 | 5.00 |
| 37 | 28.2013 | 0.096 | 130.86 | 3.1618 | 1022.32 | 10.14 |
| 38 | 28.5619 | 0.096 | 264.26 | 3.1227 | 2064.57 | 20.48 |
| 39 | 29.0172 | 0.072 | 59.44 | 3.0747 | 619.21 | 6.14 |
| 40 | 29.5813 | 0.096 | 119.64 | 3.0174 | 934.67 | 9.27 |
| 41 | 29.7121 | 0.096 | 186.01 | 3.0044 | 1453.19 | 14.42 |
| 42 | 29.9864 | 0.120 | 308.97 | 2.9775 | 1931.07 | 19.16 |
| 43 | 30.3430 | 0.120 | 243.43 | 2.9433 | 1521.46 | 15.09 |
| 44 | 31.8318 | 0.096 | 89.32 | 2.8090 | 697.82 | 6.92 |
| 45 | 31.9921 | 0.096 | 84.06 | 2.7953 | 656.71 | 6.51 |
| 46 | 32.5089 | 0.096 | 76.75 | 2.7520 | 599.61 | 5.95 |
| 47 | 33.9457 | 0.168 | 124.88 | 2.6388 | 557.50 | 5.53 |
| 48 | 35.9745 | 0.120 | 96.42 | 2.4945 | 602.63 | 5.98 |
| 49 | 38.0146 | 0.192 | 150.07 | 2.3651 | 586.21 | 5.82 |
| 50 | 38.9727 | 0.072 | 54.51 | 2.3092 | 567.82 | 5.63 |

Example 13: In Vivo Studies Using the Line 61 mThy1-Alpha-Synuclein Transgenic Mouse Model Multiple in vivo administration studies of Compound 1 were carried out in the Line 61 (L61) mThy1-alpha-synuclein transgenic mouse model of Parkinson's disease (PD). The mThy1-alpha-synuclein transgenic mouse model overexpresses wild-type human ASYN under the Thy-1 promoter studies (commonly referred to as Line 61 transgenic mice; Rockenstein et al., 2002). This transgenic mouse develops extensive accumulation of alpha-synuclein (ASYN) in areas relevant to PD (Rockenstein et al., 2002; Chesselet et al., 2012; Games et al., 2013), neurodegeneration including dopaminergic neurodegeneration, reduced dopamine (DA) and TH loss in the striatum (Masliah et al., 2000; Lam et al., 2011), and motor deficits (Fleming et al., 2004). Male transgenic and non-transgenic littermates (3-3.5 mo) were used for all in vivo studies presented here.

i. Effects of Compound 1 on ASYN Pathology and a Marker of Neuroprotection and Autophagy Alpha-synuclein (ASYN) is a neuronal protein whose dysregulation has been implicated in the pathogenesis of PD. The effects of Compound 1 on alpha-synuclein aggregation were assessed in both L61 ASYN transgenic and non-transgenic mice in a 1 month administration study. L61 ASYN transgenic mice (36 total mice, n=8-11 mice per treatment group) were injected (i.p.) with 1, 5, or 10 mg/kg of Compound 1 or a vehicle control (5% DMSO+20% Cremphor EL+0.9% normal saline) per day for 1 month. Non-transgenic mice (18 total mice, n=8-11 mice per treatment group) were used as a control and were injected daily (i.p.) with 10 mg/kg of Compound 1 or a vehicle control (5% DMSO+20% Cremphor EL+0.9% normal saline) per day for 1 month. At the end of one month, the mice were sacrificed, and immunohistochemical (IHC) detection of total alpha-synuclein deposits, insoluble alpha-synuclein deposits (PK+ resistant), microtubule-associated protein 1A/1B-light chain 3 (LC3), and monomeric alpha-synuclein levels were assessed in the harvested brain tissues.

Data from the 1 month administration study show that Compound 1 at doses of 1, 5 and 10 mg/kg (i.p., once daily) produced beneficial actions which include reductions in cortical hippocampal and striatal levels of monomeric, total and Proteinase K treatment-resistant (insoluble) ASYN as measured by immunohistochemistry (IHC) and/or biochemical methods. The data show that Compound 1 promotes the clearance of alpha-synuclein (ASYN), a neuronal protein whose dysregulation has been clearly implicated in the pathogenesis of PD. In addition to improvements in ASYN neuropathology, administration of Compound 1 increased levels of microtubule-associated protein 1A/1B-light chain 3 (LC3), a marker of autophagy and neuroprotective pathways. Finally, treatment using Compound 1 also produced functional improvements in the motor performance of L61 ASYN transgenic mice treated for 3 months.

Figure 7A:
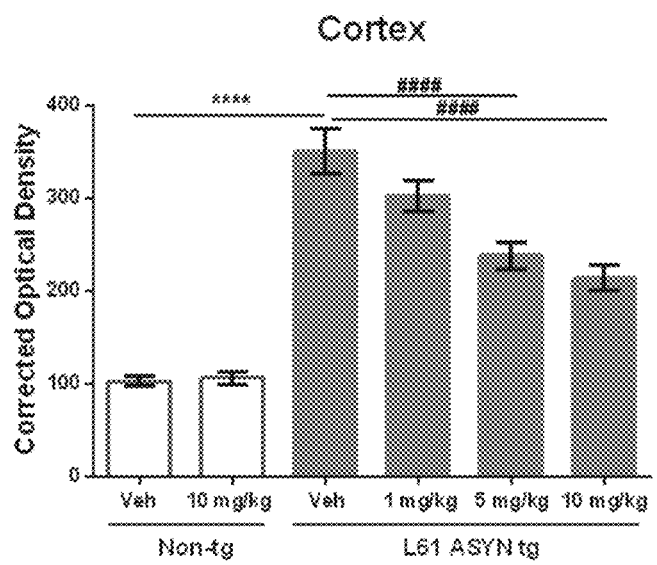
FIGS. 7A-C show the optical density of total alpha-synuclein deposits in the cortex, hippocampus, and striatum of L61 ASYN transgenic mice after i.p. administration of Compound 1 (1, 5, or 10 mg/kg per day) or a vehicle (5% DMSO+20% Cremphor EL+0.9% normal saline) for 1 month. Non-transgenic mice were used as a control group and were administered (i.p.) with Compound 1 (10 mg/kg per day) or a vehicle (5% DMSO+20% Cremphor EL+0.9% normal saline) for 1 month.
Figure 7B:
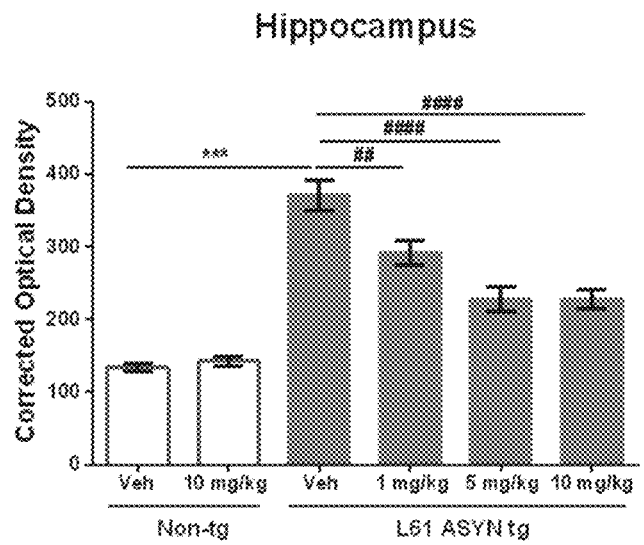
Figure 7C:
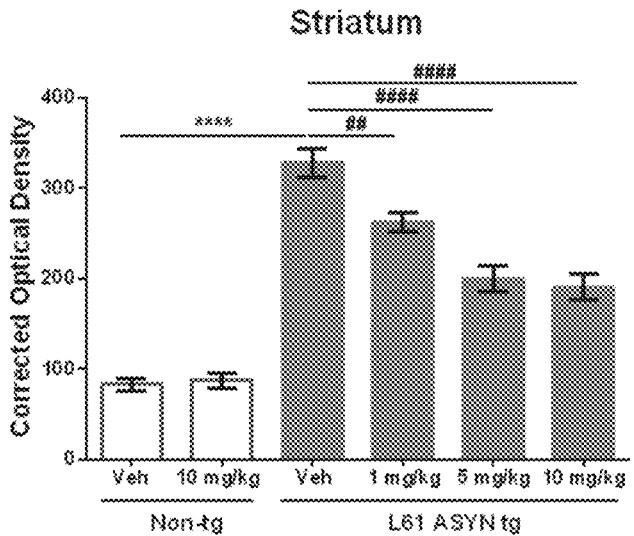
Figure 8:
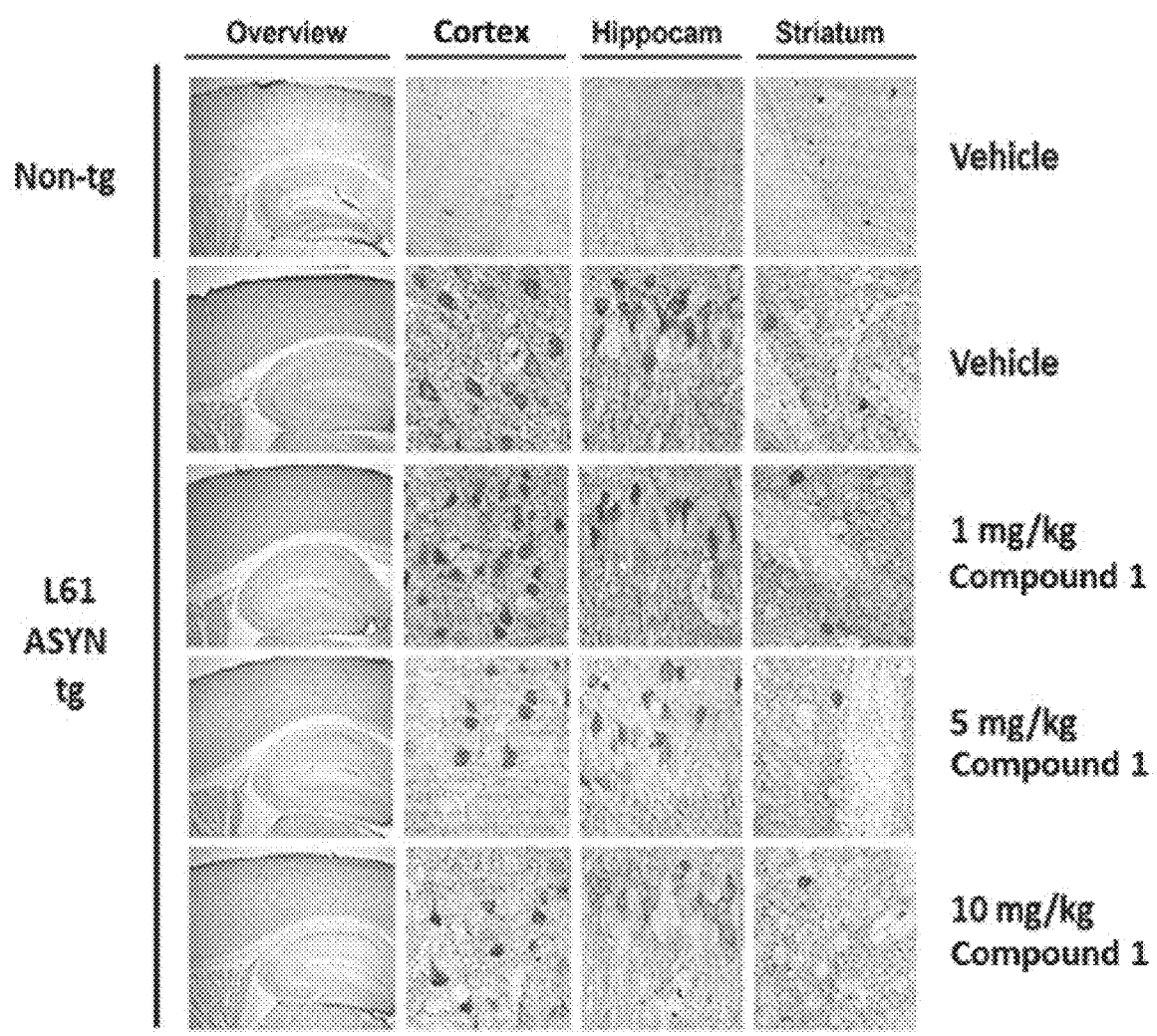
FIG. 8 shows the total alpha-synuclein deposits in representative images of cross-sections of the cortex, hippocampus, and striatum of L61 ASYN transgenic mice after i.p. administration of Compound 1 (1, 5, or 10 mg/kg per day) or a vehicle (5% DMSO+20% Cremphor EL+0.9% normal saline) for 1 month. Non-transgenic mice were used as a control group and were administered (i.p.) with a vehicle (5% DMSO+20% Cremphor EL+0.9% normal saline) for 1 month.

FIG. 7 shows the quantification of total alpha synuclein staining in cross-sections of the cortex, hippocampus, and striatum of L61 ASYN transgenic mice and control mice after i.p. administration of Compound 1 or vehicle for 1 month. FIG. 8 shows the IHC staining for total alpha-synuclein deposits in representative images of cross-sections of the neocortex, hippocampus, and striatum of L61 ASYN transgenic mice and control mice after i.p. administration of Compound 1 or vehicle for 1 month. The quantification and IHC staining of total alpha-synuclein were performed using known techniques (Rockenstein et al., *J Neurosci Res.* 2002, 68(5):568-78; Tanji et al., *Acta Neuropathol.* 2010, 120, 145-154; Nuber et al., *Brain.* 2013, February; 136(Pt 2):412-32). FIGS. 7A-C show that administration of Compound 1 (1, 5 or 10 mg/kg per day i.p. for 1 month) reduced total ASYN in the neuropil of (7A) cortex, (7b) hippocampus and (7C) striatum of transgenic mice compared to the vehicle control, as assessed by quantitative immunocytochemistry. As shown in FIG. 7, the reductions of cortical, hippocampal, and striatal levels of total alpha-synuclein resulting from Compound 1 administration are statistically significant. In particular, the data in FIG. 7A shows that when administered daily at 1 mg/kg, 5 mg/kg and 10 mg/kg, Compound 1 reduces the total alpha-synuclein level in cortex by 13%, 32% and 38% respectively as compared to a vehicle control. This is also seen in FIG. 8, which shows the total alpha-synuclein deposits in representative images of cross-sections of the cortex, hippocampus, and striatum of the brain tissues harvested from these mice. The staining in FIG. 8 shows that Compound 1 produces beneficial actions in reducing cortical, hippocampal and striatal levels of total alpha-synuclein.

Figure 9A:
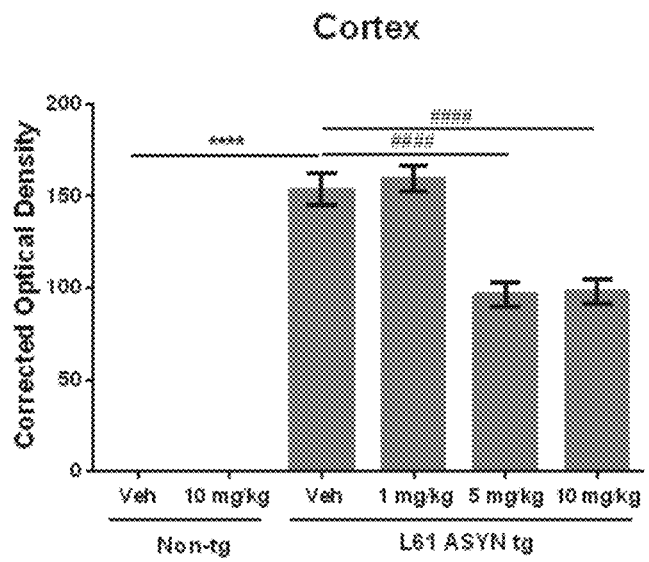
FIGS. 9A-C show the optical density of insoluble alpha-synuclein deposits (PK+resistant) in the cortex, hippocampus, and striatum of L61 ASYN transgenic mice after i.p. administration of Compound 1 (1, 5, or 10 mg/kg per day) or a vehicle (5% DMSO+20% Cremphor EL+0.9% normal saline) for 1 month. Non-transgenic mice were used as a control group and were administered (i.p.) with Compound 1 (10 mg/kg per day) or a vehicle (5% DMSO+20% Cremphor EL+0.9% normal saline) for 1 month.
Figure 9B:
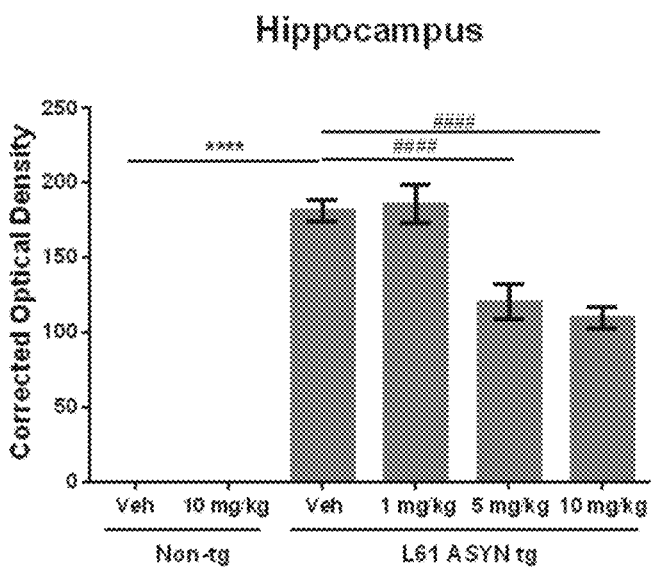
Figure 9C:
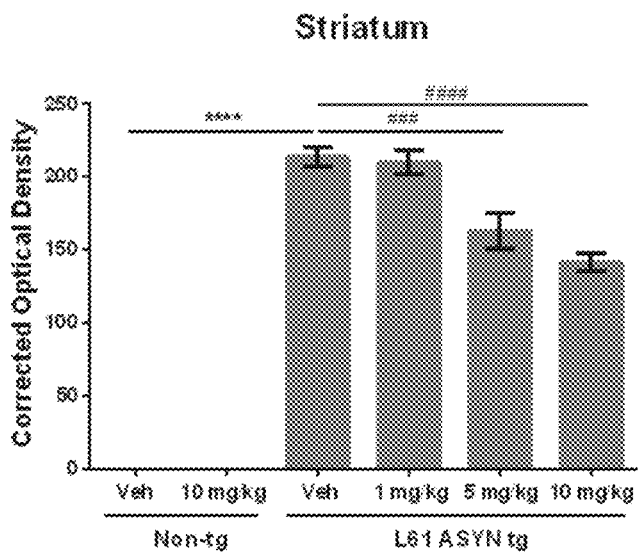
Figure 10:
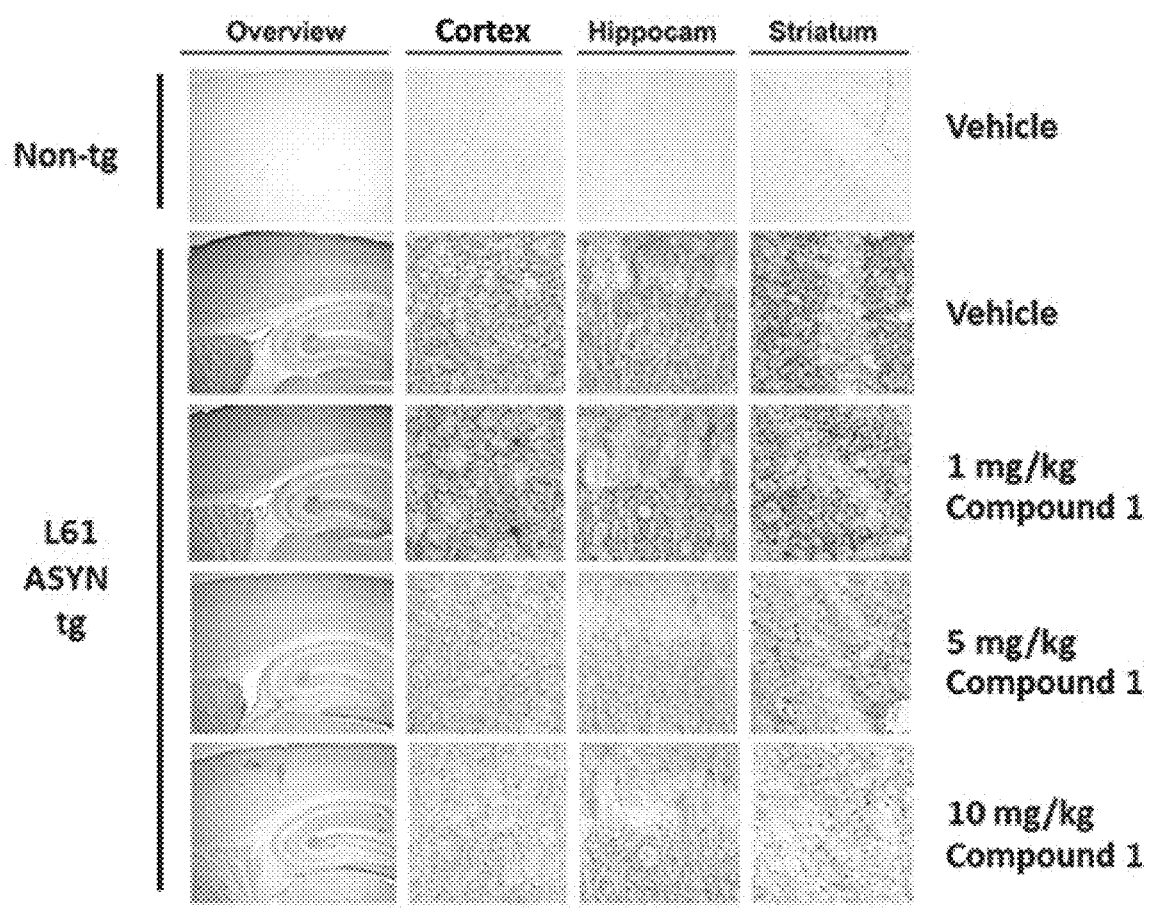
FIG. 10 shows the insoluble alpha-synuclein deposits (PK+resistant) in representative images of cross-sections of the neocortex, hippocampus, and striatum of L61 ASYN transgenic mice after i.p. administration of Compound 1 (1, 5, or 10 mg/kg per day) or a vehicle (5% DMSO+20% Cremphor EL+0.9% normal saline) for 1 month. Non-transgenic mice were used as a control group and were administered (i.p.) with a vehicle (5% DMSO+20% Cremphor EL+0.9% normal saline) for 1 month.

FIG. 9 shows the quantification of PK-resistant alpha synuclein staining in cross-sections of the cortex, hippocampus, and striatum of L61 ASYN transgenic mice and control mice after i.p. administration of Compound 1 or vehicle for 1 month. FIG. 10 shows the IHC staining for PK-resistant alpha-synuclein deposits in representative images of cross-sections of the cortex, hippocampus, and striatum of L61 ASYN transgenic mice and control mice after i.p. administration of Compound 1 or vehicle for 1 month. The quantification and IHC staining of PK-resistant alpha-synuclein were performed using known techniques (Rockenstein et al., *J Neurosci Res.* 2002, 68(5):568-78; Tanji et al., *Acta Neuropathol.* 2010, 120, 145-154; Nuber et al., *Brain.* 2013, February; 136(Pt 2):412-32). As shown in FIGS. 9A-C and 10, administration of Compound 1 (1, 5 or 10 mg/kg per day i.p. for 1 month) also reduced the insoluble alpha-synuclein deposits (PK+resistant) in the (9A) cortex, (9B) hippocampus, and (9C) striatum of the transgenic mice. FIG. 9 shows that the reductions of cortical, hippocampal and striatal levels of PK-resistant alpha-synuclein resulting from Compound 1 administration are statistically significant. In particular, the data in FIG. 9A shows that Compound 1 when administered daily at 5 mg/kg and 10 mg/kg reduces the PK-resistant alpha synuclein levels in cortex by 37% and 36% respectively as compared to vehicle-treated mice. The staining in FIG. 10 shows that Compound 1 produces beneficial actions in reducing cortical, hippocampal and striatal levels of PK-resistant alpha-synuclein.

Figure 11A:
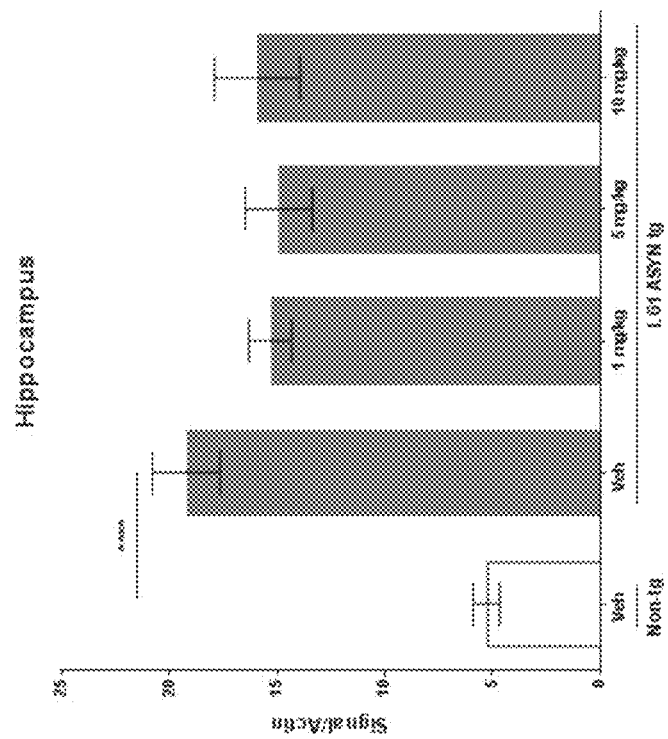
FIGS. 11A-B show the biochemical evaluation of brain levels of monomeric ASYN in the frontal cortex and hippocampus of L61 ASYN transgenic mice after i.p. administration of Compound 1 (1, 5, or 10 mg/kg per day) or a vehicle (5% DMSO+20% Cremphor EL+0.9% normal saline) for 1 month. Non-transgenic mice were used as a control group and were administered (i.p.) with a vehicle (5% DMSO+20% Cremphor EL+0.9% normal saline) for 1 month.
Figure 11B:
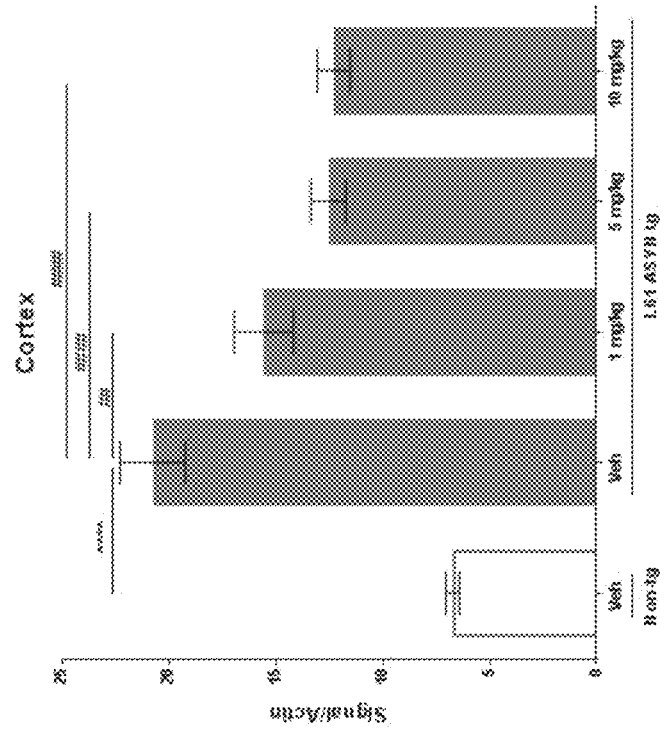
Figure 12A:
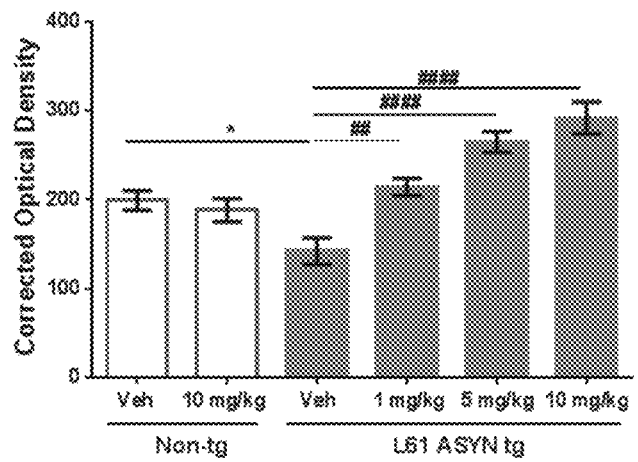
FIGS. 12A-C show the optical density of microtubule-associated protein 1A/1B-light chain 3 (LC3) in the cortex, hippocampus, and striatum of L61 ASYN transgenic mice after i.p. administration of Compound 1 (1, 5, or 10 mg/kg per day) or a vehicle (5% DMSO+20% Cremphor EL+0.9% normal saline) for 1 month. Non-transgenic mice were used as a control group and were administered (i.p.) with Compound 1 (10 mg/kg per day) or a vehicle (5% DMSO+20% Cremphor EL+0.9% normal saline) for 1 month.
Figure 12B:
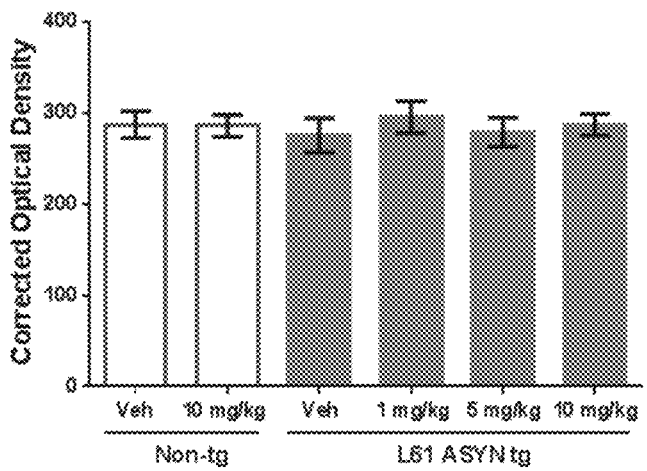
Figure 12C:
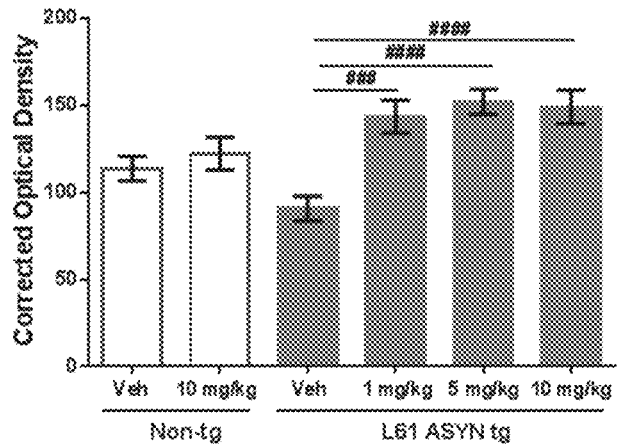
Figure 13:
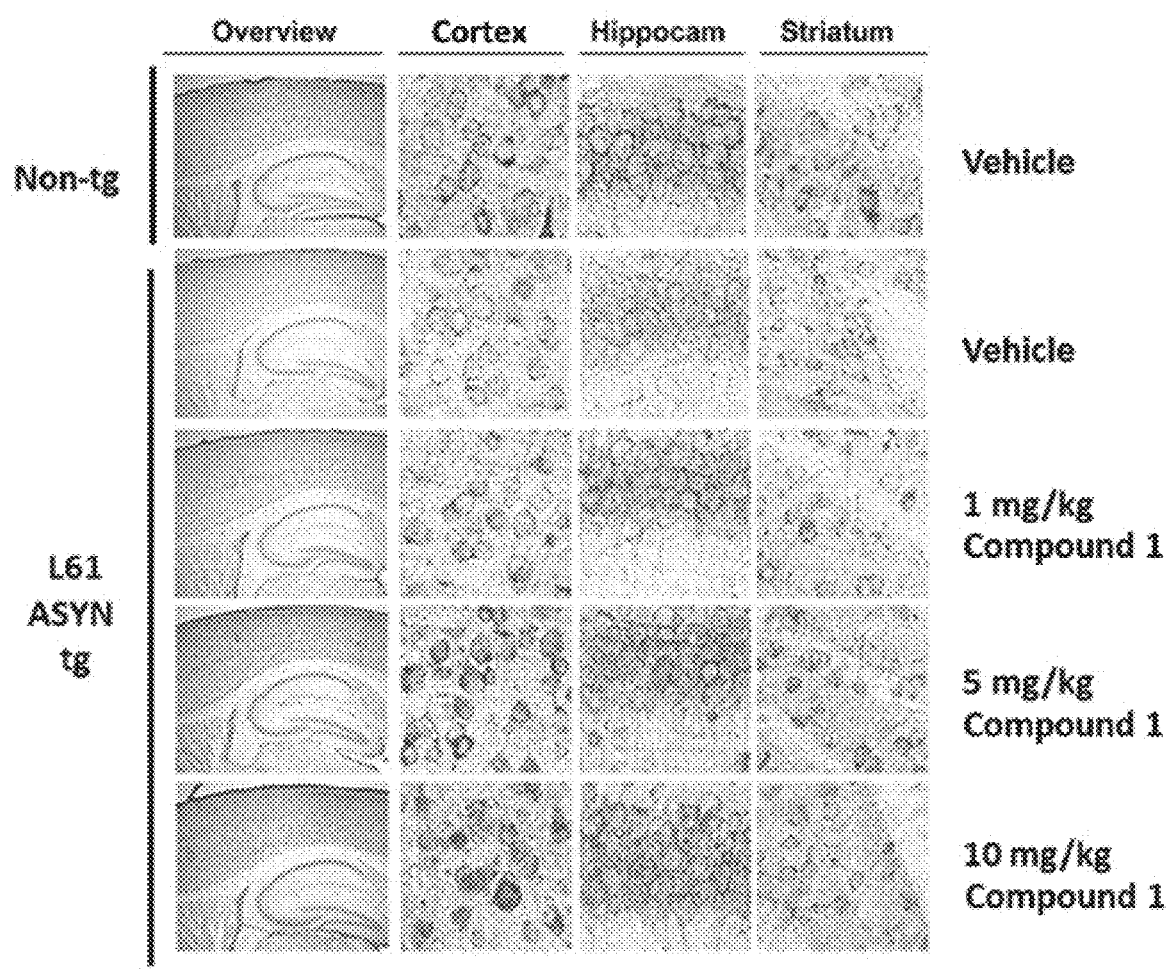
FIG. 13 shows the levels of LC3 immunolabeling via IHC in representative images of cross-sections of the neocortex, hippocampus, and striatum of L61 ASYN transgenic mice after i.p. administration of Compound 1 (1, 5, or 10 mg/kg per day) or a vehicle (5% DMSO+20% Cremphor EL+0.9% normal saline) for 1 month. Non-transgenic mice were used as a control group and were administered (i.p.) with a vehicle (5% DMSO+20% Cremphor EL+0.9% normal saline) for 1 month.

FIG. 11A-B show that administration of Compound 1 (1, 5 or 10 mg/kg per day i.p. for 1 month) reduced the (11A) cortical and (11B) hippocampal levels of monomeric ASYN in the cytosolic fraction of brain homogenates from L61 ASYN transgenic mice. Biochemical evaluations were conducted using a ProteinSimple© western biochemical evaluation. Briefly, samples were mixed with pre-calculated volumes of 0.1×Sample Buffer and 5×Fluorescent Master Mix to make a final sample concentration of 0.4 mg/mL in 10 μL solution for signal optimization and evaporation reduction. Approximately 0.4 μL of sample was mixed with 2 μL of 5× fluorescent Master Mix and 7.8 μL of 0.1× Sample Buffer, vortexed, spun, and heated at 95° C. for 5 min. After brief cooling, the samples, blocking reagent, wash buffer, primary antibodies, secondary antibodies, and chemiluminescent substrate were dispensed into designated wells in the manufacturer provided plate (Kit #PS-MK14, ProteinSimple). Following plate loading the separation and immunodetection was performed automatically using default settings. The Compass software (ProteinSimple, version 2.6.7) was used to generate a report that included molecular weight, area, percent area and signal to noise for each protein detected. Data for the target protein of interest was normalized to beta-actin levels and further normalized between cartridges. Data are presented here as mean values±SEM.

It is shown in FIG. 11A-B that when administered daily at 1 mg/kg, 5 mg/kg or 10 mg/kg, Compound 1 reduces the levels of monomeric ASYN in the cortex as compared to vehicle treated L61 transgenic mice, in a statistically significant manner.

FIGS. 12A-C and 13 show that administration of Compound 1 (1, 5 or 10 mg/kg per day i.p. for 1 month) increased levels of microtubule-associated protein 1A/1B-light chain 3 (LC3) immunolabeling in the (12A) cortex and (12C) striatum, but not in the (12B) hippocampus of the transgenic mice.

ii. Effects of Compound 1 on Motor Performance

The effects of Compound 1 on the motor performance deficits (grip strength) and a marker of neuroinflammation (Translocator Protein (18 kDa)) were assessed in both L61 ASYN transgenic and non-transgenic mice in a 3 month administration study.

Compound 1 was injected into L61 ASYN transgenic mice and non-transgenic control mice (i.p., once daily) at doses of 5 and 10 mg/kg for 3 months (79 total mice, n=14-17 mice per treatment group). The vehicle control consisted of a solution containing 5% DMSO+20% Cremphor EL+0.9% normal saline. The baseline grip strength of mice was evaluated prior to starting treatments for the 3 month study, and then re-evaluated following 70 days of treatment with vehicle or Compound 1 (5 or 10 mg/kg, i.p. daily).

Figure 14:
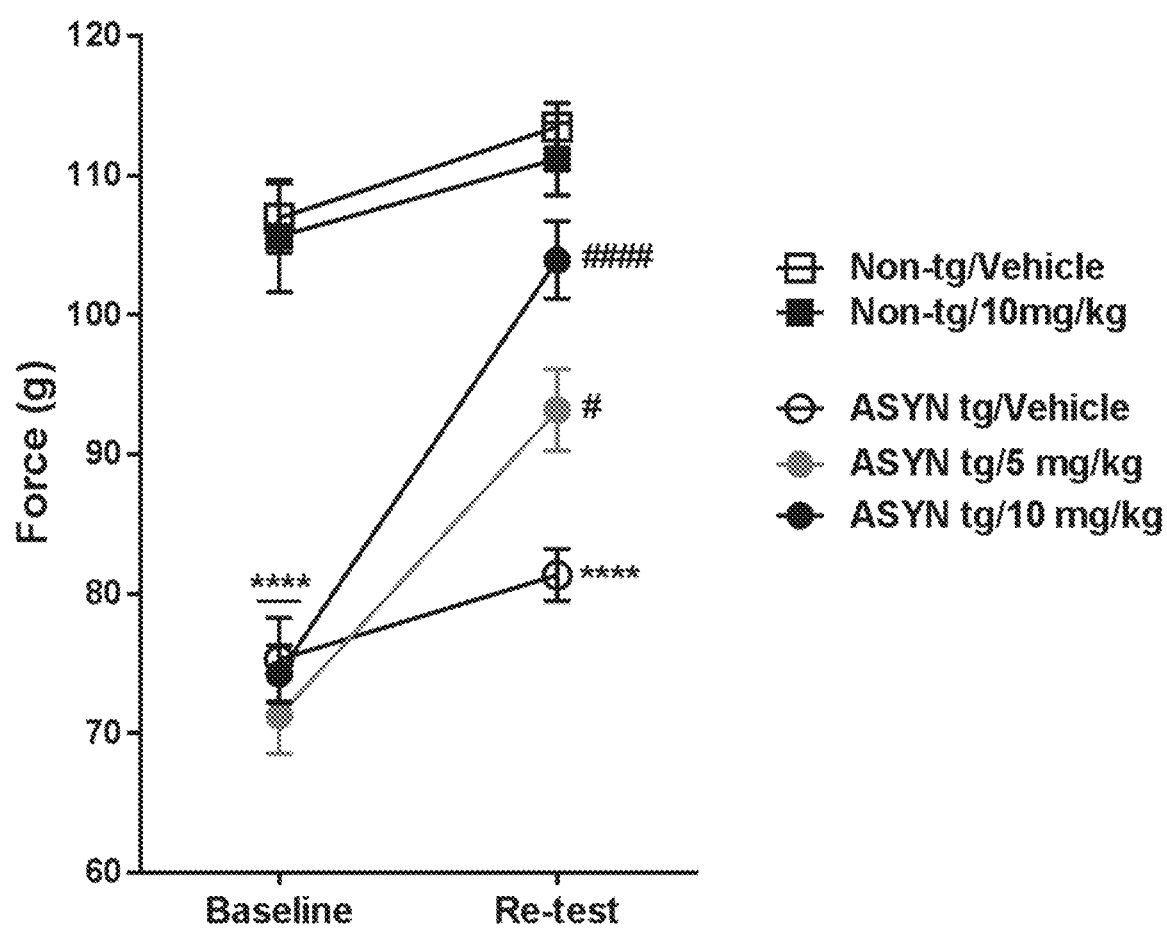
FIG. 14 shows the grip strength evaluation of L61 ASYN transgenic mice after administration with Compound 1 (5 or 10 mg/kg) or a vehicle (5% DMSO+20% Cremphor EL+0.9% normal saline) for 3 months. Non-transgenic mice were used as a control group and were administered (i.p.) with Compound 1 (10 mg/kg per day) or a vehicle (5% DMSO+20% Cremphor EL+0.9% normal saline) for 3 months.

As shown in FIG. 14, administration of Compound 1 (5 or 10 mg/kg, i.p. daily) for the 3 month study produced beneficial effects on transgenic motor deficit phenotype present in L61 ASYN transgenic mice. At baseline, there was a statistically significant grip strength deficit in transgenic mice compared to non-transgenic mice. Treatment with Compound 1 (5 & 10 mg/kg) improved L61 ASYN transgenic grip strength deficits. After 70 days of treatment, transgenic mice treated with Compound 1 at both 5 mg/kg and 10 mg/kg showed higher grip strengths than vehicle-treated transgenic mice in a statistically significant manner.

iii. Effects of Compound 1 on Neuroinflammation Marker TSPO

Neuroinflammation is associated with increased expression of the 18-kDa translocator protein (TSPO), which is a marker for inflammation and is present on the mitochondria of activated microglia, astroglia and macrophages (Crawshaw and Robertson 2017). The effects of Compound 1 on the levels of Translocator Protein (18 kDa) (TSPO) were assessed in both L61 ASYN transgenic and non-transgenic mice in the aforementioned 3 month administration study. At the end of the study, the mice were sacrificed, and immunofluorescence (IF) detection of TSPO were assessed in the harvested brain tissues.

Figure 15A:
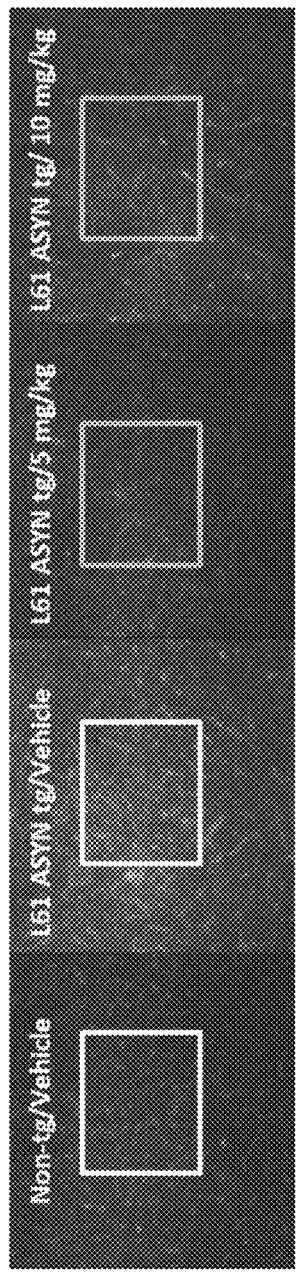
FIG. 15A shows the levels of Translocator Protein (18 kDa) (TSPO) in representative images of cross-sections of the frontal cortex of L61 ASYN transgenic mice after administration with Compound 1 (5 or 10 mg/kg) or a vehicle (5% DMSO+20% Cremphor EL+0.9% normal saline) for 3 months. Non-transgenic mice were used as a control group and were administered (i.p.) with Compound 1 (10 mg/kg per day—data not shown) or a vehicle (5% DMSO+20% Cremphor EL+0.9% normal saline) for 3 months.
Figure 15B:
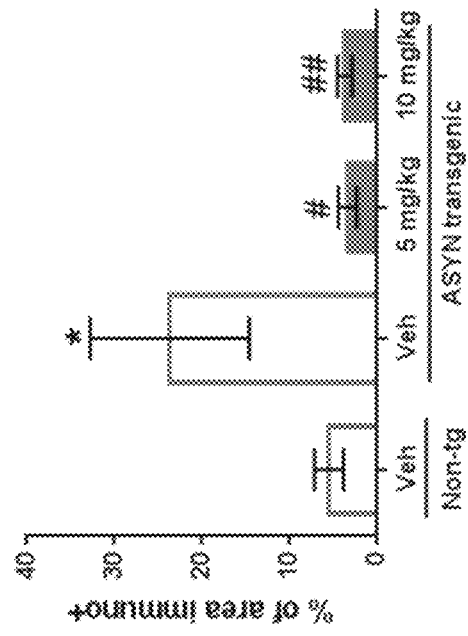
FIG. 15B shows the quantification of the TSPO images from FIG. 15A.

FIGS. 15A-B show the levels of TSPO immunolabeling in representative cross-sections of the cortex of the mice. As shown in FIGS. 15A and 15B, administration of Compound 1 (5 and 10 mg/kg, i.p. daily) significantly decreased the levels of TPSPO in L61 ASYN transgenic mice compared to the vehicle control. FIG. 15A shows representative TSPO immunostaining in the cortex of L61 transgenic mice injected daily with Compound 1 versus vehicle control. FIG. 15B shows the quantification of TPSO staining from representative cortical sections. The harvested brain tissues were fixed (drop fixed in 4% paraformaldehyde), sectioned using a vibratome, and representative sections were assessed for TSPO with standard immunofluorescence (IF) staining. Briefly, the right hemibrain was post-fixed in phosphate-buffered 4% PFA (pH 7.4) at 4° C. for 48 and then serially sectioned into 40 uM thick coronal sections using a vibratome. Sections were free-floated and incubated overnight at 4° C. Immunolabeling studies of TSPO were conducted using knockout validated rabbit monoclonal anti-TSPO antibody (1:500; ab199779; abcam, Temecula, Calif., USA) pre-conjugated to Alexa Fluor 488 secondary antibody. Immunolabeling, imaging and analysis was performed on blindcoded sections from Line 61 transgenic and non-transgenic mice. Slides were imaged using a EVOS Auto FL imaging system (ThermoFisher Scientific, Waltham, Mass., USA) with a 10× objective (EVOS PlanFL PH2 LWD; AMEP4681). Digitized images were analyzed using Halo (Indica Labs, Corrales, N. Mex., USA) image analysis software package by placing an ROI frame within the neocortex (standardized frame placed on all images). A thresholding algorithm was defined and then applied equally to all images to determine the percentage of cortex ROI TSPO immunolabeled. The results of the analysis were then exported for graphing and statistical analysis.

Representative IF images in FIG. 15A show that when administered daily at 5 mg/kg or 10 mg/kg, Compound 1 produced beneficial actions in reducing cortical levels of TSPO, as visualized by reduced IF staining intensity. Furthermore, the quantification in FIG. 15B shows that Compound 1 at 5 mg/kg or 10 mg/kg reduces the TSPO level in a statistically significant manner as compared to vehicle-treated mice.

iv. Effects of Compound 1 on Neuroinflammation Marker GFAP

Neuroinflammation is also associated with increased expression of glial fibrillary acidic protein (GFAP) in activated astrocytes, which is induced by a variety of molecules including pro-inflammatory mediators released from activated microglia (Saijo et al. 2009). Increased expression of glial fibrillary acidic protein (GFAP) represents astroglial activation and gliosis during neurodegeneration. (Brahmachari et al., 2006). The effects of Compound 1 on GFAP expression were assessed in both L61 ASYN transgenic and non-transgenic mice in a 1 month administration study. After 30 days, the mice were sacrificed, and IHC detection of GFAP was assessed in the harvested brain tissues.

Figure 16:
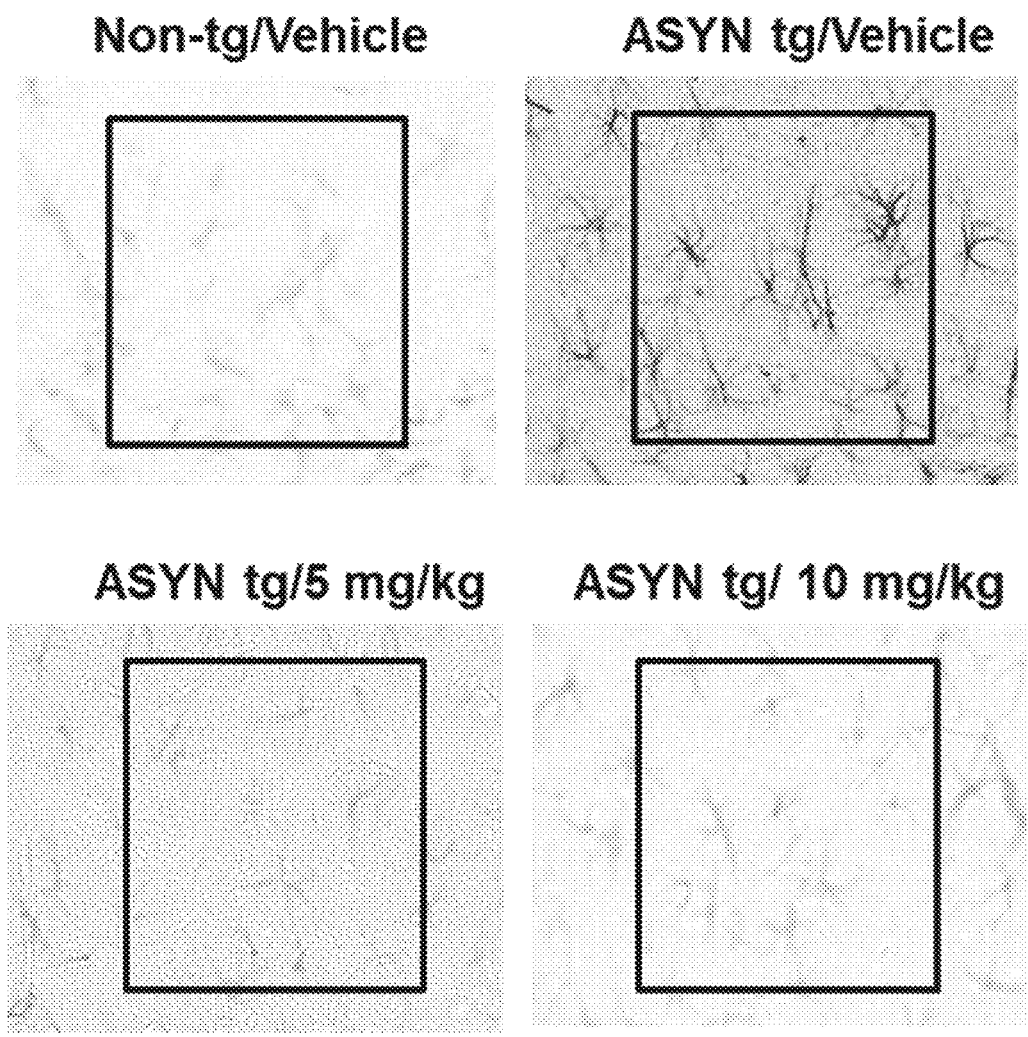
FIG. 16 shows the IHC staining for GFAP in representative images of the hippocampus of L61 ASYN transgenic mice after i.p. administration of Compound 1 (1, 5, or 10 mg/kg per day) or a vehicle (5% DMSO+20% Cremphor EL+0.9% normal saline) for 1 months. Non-transgenic mice were used as a control group and were administered (i.p.) with Compound 1 (10 mg/kg per day—data not shown) or a vehicle (5% DMSO+20% Cremphor EL+0.9% normal saline) for 3 months.
Figure 17:
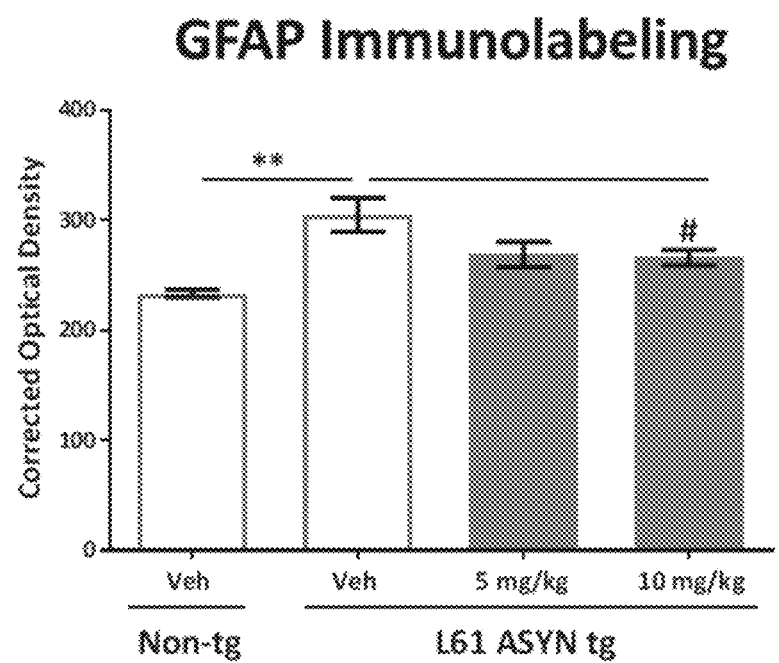
FIG. 17 shows the optical density in IHC staining for GFAP in the hippocampus of L61 ASYN transgenic mice after i.p. administration of Compound 1 (1, 5, or 10 mg/kg per day) or a vehicle (5% DMSO+20% Cremphor EL+0.9% normal saline) for 3 months. Non-transgenic mice were used as a control group and were administered (i.p.) with Compound 1 (10 mg/kg per day—data not shown) or a vehicle (5% DMSO+20% Cremphor EL+0.9% normal saline) for 1 months.

FIG. 16 shows representative GFAP immunostaining in sections containing hippocampus in L61 transgenic mice injected daily with Compound 1 versus vehicle control. FIG. 17 shows the quantification of the described GFAP staining from representative brain sections. The harvested brain tissues from treated mice were fixed (drop fixed in 4% PFA) and then sectioned into 40 micro thick sections using a vibratome. The representative sections containing the hippocampus were assessed for GFAP with standard immunohistochemistry staining. The general methods used for GFAP immunostaining follow those described in Rockenstein et al., *J Neurosci Res.* 2002, 68(5):568-78. Representative IHC images in FIG. 16 show that when administered daily at 5 mg/kg or 10 mg/kg, Compound 1 produces beneficial actions in reducing cortical levels of GFAP, as visualized by reduced IHC staining intensity. Furthermore, the quantification in FIG. 17 shows that at the 10 mg/kg dose, Compound 1 reduces the cortical GFAP levels in a statistically significant manner.

v. Effects of Compound 1 on Dopaminergic (DAT) Transporter Immunolabeling Levels In Parkinson's disease, uncontrolled neuroinflammation caused by the synergic activation of microglia and astroyctes ultimately contributes to the enhanced death of DA neurons in striatum during neurodegeneration.

Figure 18:
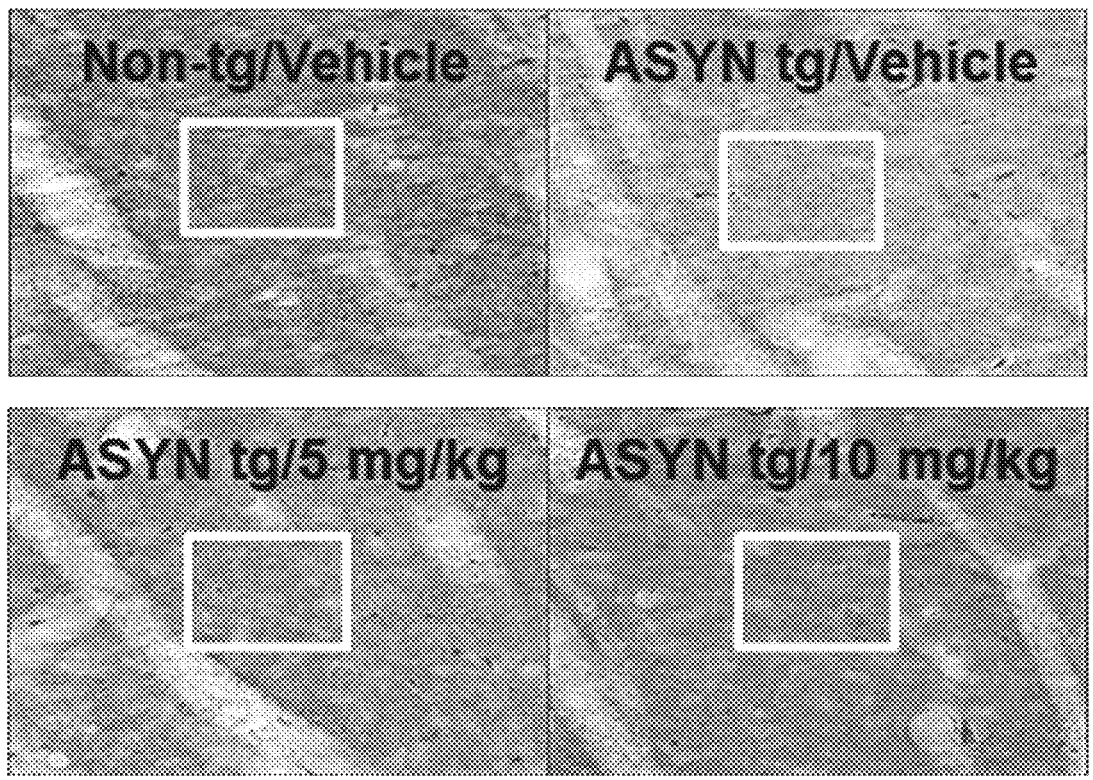
FIG. 18 shows IHC staining of DAT in representative images of cross-sections of the striatum of L61 ASYN transgenic mice after administration with Compound 1 (5 or 10 mg/kg) or a vehicle (5% DMSO+20% Cremphor EL+0.9% normal saline) for 3 months. Non-transgenic mice were used as a control group and were administered (i.p.) with Compound 1 (10 mg/kg per day—data not shown) or a vehicle (5% DMSO+20% Cremphor EL+0.9% normal saline—data not shown) for 3 months.
Figure 19:
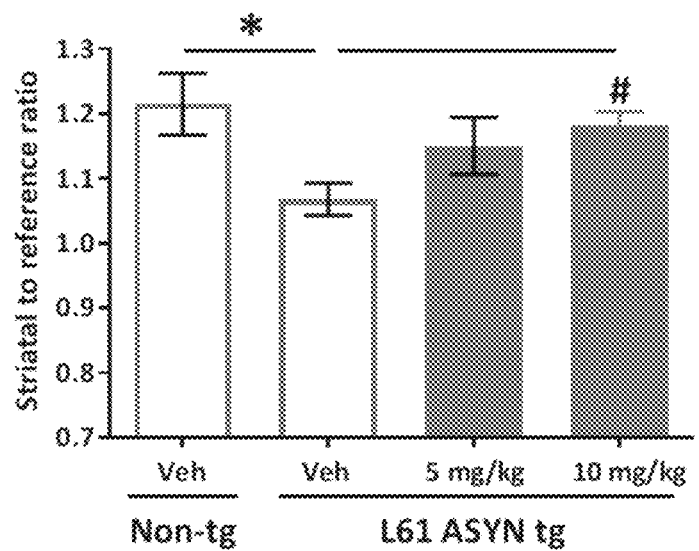
FIG. 19 shows the striatal-to-reference ratio from optical density of IHC staining of DAT in representative images of cross-sections of the striatum and reference region (cortex) of L61 ASYN transgenic mice after administration with Compound 1 (5 or 10 mg/kg) or a vehicle (5% DMSO+20% Cremphor EL+0.9% normal saline) for 3 months. Non-transgenic mice were used as a control group and were administered (i.p.) with Compound 1 (10 mg/kg per day) or a vehicle (5% DMSO+20% Cremphor EL+0.9% normal saline) for 1 month.

FIG. 18 shows representative dopaminergic (DAT) immunostaining in sections corresponding to the striatum in L61 transgenic mice injected daily with Compound 1 versus vehicle control. FIG. 19 shows the quantification of the described DAT staining from level matched sagittal sections containing striatum and of the cortex as a reference binding region. The harvested brain tissues were drop fixed using 4% PFA and sectioned on a vibratome, and representative sections corresponding to the striatum and cerebellum were assessed for DAT with IHC staining.

Immunolabeling studies of DAT were conducted using a monoclonal antibody (1:500; MAB369; Millipore, Temecula, Calif.) and a biotinylated secondary antibody (1:100; BA4000, Vector Labs) and analysis was performed on blindcoded sections from Line 61 transgenic and non-transgenic mice. Slides were digitized using a high resolution automated Nanozoomer slide scanner (Hamamatsu Corp.). Digitized images were analyzed using Halo (Indica Labs) image analysis software package by placing an ROI frame within the dorsal striatum and another within a separate reference brain region (for normalization of DAT signal). A thresholding algorithm was defined and then applied equally to all images to determine the average optical density of DAT immunolabeling across each ROI. The results of the analysis were then exported for graphing and statistical analysis and the striatal DAT:cortical (reference region) DAT optical densities ratio was calculated for each subject.

Representative IF images in FIG. 18 show that when administered daily at 5 mg/kg or 10 mg/kg, Compound 1 produces beneficial actions in restoring striatal levels of DAT, as visualized by increased immunofluorescence intensity as compared to vehicle-treated L61 mice. Quantification of DAT density was carried out by calculating the immunofluorescence in striatal sections against that in cerebellum sections to derive a striatal-to-reference ratio. The quantification in FIG. 19 shows that Compound 1 at the 10 mg/kg dose reduces the GFAP levels in a statistically significant manner.

vi. Effects of Compound 1 on Neuroinflammation and Amyloid Beta Plaques

Neuroinflammation is associated with increased expression of the 18-kDa translocator protein (TSPO), which is present on the mitochondria of activated microglia, astroglia and macrophages (Crawshaw and Robertson 2017). The effects of Compound 1 on TSPO expression were assessed in both L41 APP transgenic and non-transgenic mice in a 1 month administration study. L41 APP transgenic mice (36 total mice, n=8-11 mice per treatment group) were injected (i.p.) daily with 5 mg/kg of Compound 1 or a vehicle control (5% DMSO+20% Cremphor EL+0.9% normal saline) for 3 months. Non-transgenic mice (18 total mice, n=8-11 mice per treatment group) were used as a control and were injected daily (i.p.) with 10 mg/kg of Compound 1 (data not shown) or a vehicle control (5% DMSO+20% Cremphor EL+0.9% normal saline) for 1 month. After 30 days, the mice were sacrificed, and immunofluoresence (IF) detection of TSPO were assessed in the harvested brain tissues.

Figure 20:
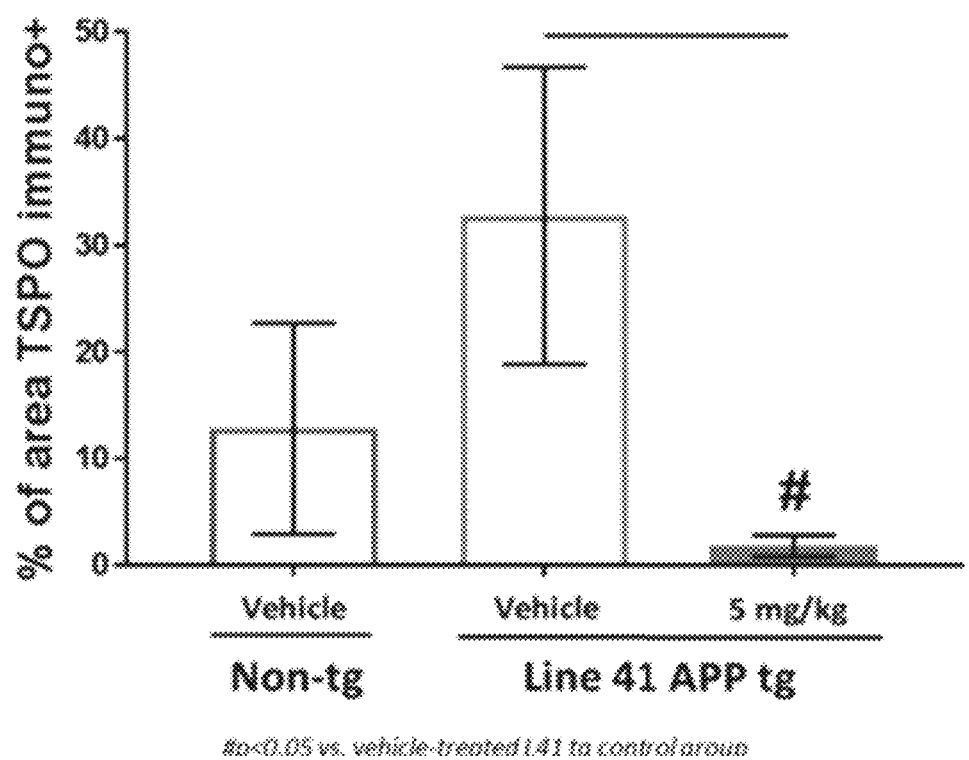
FIG. 20 shows quantitation in TSPO immunofluorescence staining in representative brain sections of L41 APP transgenic mouse after daily i.p. injections of vehicle or Compound 1 at 5 mg/kg or vehicle for 70 days. Data for non-transgenic mouse administered with daily ip injections of vehicle was also shown.

FIG. 20 shows the quantification of TPSO staining from representative brain sections. The harvested brain tissues were drop fixed using 4% PFA and sectioned on a vibratome, and representative sections corresponding to the neuropil of cortex were assessed for TSPO with standard immunofluorescence (IF) staining. The results show that when administered daily at 5 mg/kg, Compound 1 produced beneficial actions in reducing cortical levels of TSPO, as visualized by reduced IF staining intensity. Furthermore, the quantification in FIG. 20 shows that when administered daily at 5 mg/kg, Compound 1 reduces the TSPO level in a statistically significant manner as compared to vehicle-treated Line 41 mice.

vii. Effects of Compound 1 on Amyloid Beta Plaques

As described earlier, Line 41 transgenic mice express high levels of the mutant hAPP751 and develop mature plaques in the cortex, hippocampus, thalamus and olfactory region of mouse brain. The effects of Compound 1 on Amyloid beta plaque formation were assessed in both L41 APP transgenic and non-transgenic mice in a 1 month administration study. After 30 days, the mice were sacrificed, and immunofluorescence (IF) detection of amyloid beta were assessed in the harvested brain tissues.

Figure 21:
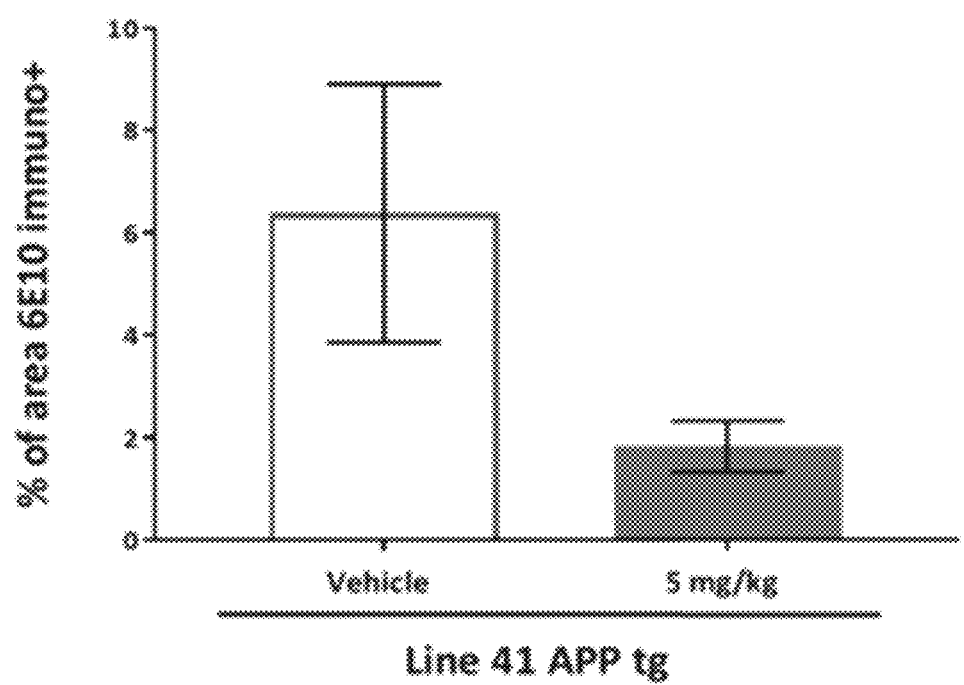
FIG. 21 shows quantitation in immunofluorescence staining of amyloid beta using 6E10 antibodies in representative brain sections of L41 APP transgenic mouse after daily i.p. injections of vehicle or Compound 1 at 5 mg/kg or vehicle for 70 days. Data for non-transgenic mouse administered with daily i.p. injections of vehicle was also shown.

FIG. 21 shows the quantification of amyloid beta staining in L41 transgenic mice injected daily with Compound 1 versus vehicle control. The harvested brain tissues were drop fixed using 4% PFA and sectioned on a vibratome, and representative sections containing the neuropil of cortex, hippocampus and striatum were assessed for amyloid beta with standard IHC staining.

On approximately day 30, all subjects were euthanized within 2 hours of the last treatment and brain and other samples were collected. Brains were removed and divided sagitally. The right hemibrain was post-fixed in phosphate-buffered 4% PFA (pH 7.4) at 4° C. for 48 hours for neuropathological analysis. Drop fixed hemibrains were then serially sectioned into 40 uM thick coronal sections using a vibratome. Sections were free-floated and incubated overnight at 4° C. with primary antibodies. To confirm the specificity of primary antibodies, control experiments were performed in which sections were incubated overnight in the absence of primary antibody (deleted), preimmune serum, or primary antibody preadsorbed for 48 h with 20-fold excess of the corresponding peptide.

Immunolabeling studies of β-amyloid pathology were conducted using a purified anti-b-amyloid 1-16 antibody (1:500; 6E10 clone, reactive to amino acid residue 1-16 of j-amyloid and APP; #SIG-39320; Covance Research Products, Inc., Dedham, Mass., USA). Following incubations with primary antibodies, sections were then incubated with biotinylated secondary antibodies (1:200, Vector Laboratories, Burlingame, Calif.) and visualized using an avidin-biotin (ABC) kit (Vector Laboratories, Burlingame, Calif.) with diaminobenzidine tetrahydrochloride (DAB; Sigma-Aldrich, St. Louis, Mo.) as the chromogen.

Prepared slides were imaged at 40× using a high-resolution Hamamatsu Nanozoomer™ scanner located in the Microscopy Core in the UCSD Department of Neurosciences. Digital images were then transferred to Neuropore and analyzed using the Halo® imaging software package (Indica Labs, Corrales, N. Mex.). The same standardized regional mask (region of interest (ROI), with equal dimensions for equal analysis of area) was imported onto each image and positioned over the dorsal striatum. A window for thresholding was defined using representative images from the vehicle control groups, saved, and then applied to all images via a batch processing algorithm. Data are presented as percent (%) area of ROI immunopositive for each marker.

Images were evaluated for specimen and imaging problems and any issues were noted prior to unblinding of samples and statistical analyses.

The results show that when administered daily at 5 mg/kg, Compound 1 produced beneficial actions in reducing cortical levels of amyloid beta, as visualized by reduced IF staining intensity. Furthermore, the quantification in FIG. 20 shows that when administered daily at 5 mg/kg, Compound 1 reduces the amyloid beta level in a statistically significant manner as compared to vehicle-treated Line 41 mice.

For all Figures, all data are presented as the group means±standard error of mean (****$p<0.0001$ or *$p<0.05$ denotes a statistically significant baseline or vehicle-treated phenotype compared to vehicle-treated non-transgenic control group; #$p<0.05$, ##$p<0.01$, ###$p<0.001$, or ####$p<0.0001$ denotes a statistically significant treatment effect in Compound 1-treated transgenic groups versus the vehicle-treated transgenic control group).

The invention claimed is:

1. A pharmaceutical composition comprising (a) at least one compound of Formula (I),

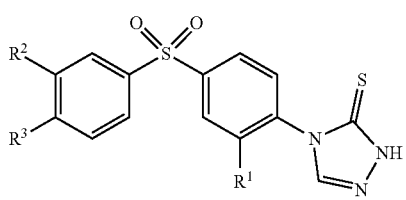

(I)

wherein
$R^1$, $R^2$, and $R^3$ are each independently hydrogen, hydroxy, halogen, optionally substituted $C_{1-4}$ alkyl, optionally substituted $C_{1-4}$ alkoxy, —CN, —C(O)$R^x$, —C(O)O$R^x$, —S(O)$_2 R^x$, or —N$R^y R^z$;
$R^x$, $R^y$, and $R^z$ are each independently H or optionally substituted $C_{1-4}$ alkyl, or $R^y$ and $R^z$ taken together with the nitrogen to which they are attached form an optionally substituted monocyclic heterocycloalkyl ring;
or a pharmaceutically acceptable salt thereof, and
(b) a pharmaceutically acceptable excipient,
wherein the pharmaceutically acceptable excipient is selected from the group consisting of a polymeric agent, carboxymethyl cellulose (CMC), hydroxypropyl cellulose (HPC), hydroxyethyl cellulose (HEC), hydroxypropylmethyl cellulose (HPMC), gelatin, gelatin hydrolysate, sucrose, dextrose, polyvinylpyrrolidone (PVP), polyethyleneglycol (PEG), vinyl pyrrolidone copolymers, pregelatinized starch, sorbitol, glucose, Kollidon, and polyacrylates.

2. The pharmaceutical composition of claim 1, wherein the pharmaceutically acceptable excipient is selected from the group consisting of hydroxypropylmethyl cellulose (HPMC), polyvinylpyrrolidone (PVP), and Kollidon.

3. The pharmaceutical composition of claim 1, wherein the pharmaceutical composition is in the form of a spray dry dispersion (SDD).

4. The composition of claim 1, wherein $R^1$ is hydrogen.

5. The composition of claim 1, wherein $R^1$ is —OCH$_2$CH$_2$—O—CH$_2$CH$_3$ or —OCH$_2$CH$_2$OCH$_3$.

6. The composition of claim 1, wherein $R^1$ is —NHCH$_2$CH$_2$OH or —N(CH$_2$CH$_3$)$_2$.

7. The composition of claim 1, wherein $R^1$ is morpholinyl, 4-methyl-piperazin-1-yl, piperidinyl, or pyrrolidinyl.

8. The composition of claim 1, wherein $R^2$ is hydrogen, $C_{1-4}$ alkyl, or substituted $C_{1-4}$ alkyl.

9. The composition of claim 1, wherein $R^2$ is CF$_3$.

10. The composition of claim 1, wherein $R^2$ is methyl.

11. The composition of claim 1, wherein $R^2$ is optionally substituted $C_{1-4}$ alkoxy, —CN, or —N$R^y R^z$.

12. The composition of claim 1, wherein $R^2$ is —N(CH$_3$)$_2$.

13. The composition of claim 1, wherein $R^2$ is morpholinyl.

14. The composition of claim 1, wherein $R^2$ is methoxy, —OCH$_2$CH$_2$—O—CH$_2$CH$_3$, or —OCH$_2$CH$_2$OCH$_3$.

15. The composition of claim 1, wherein $R^3$ is halogen.

16. The composition of claim 1, wherein $R^3$ is chloro.

17. The composition of claim 1, wherein $R^3$ is hydrogen.

18. The composition of claim 1, wherein $R^3$ is methyl.

19. The composition of claim 1, wherein $R^3$ is —CN.

20. The composition of claim 1, wherein $R^3$ is morpholinyl.

21. The composition of claim 1, wherein $R^3$ is $C_{1-4}$ alkoxy.

22. The composition of claim 1, wherein the compound is selected from the group consisting of

| Compound No. | Structure | Name |
|---|---|---|
| 1 | 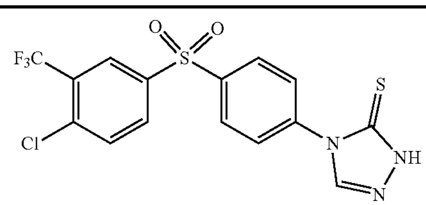 | 4-(4-((4-chloro-3-(trifluoromethyl)phenyl)sulfonyl)phenyl)-2,4-dihydro-3H-1,2,4-triazole-3-thione; |
| 2 | 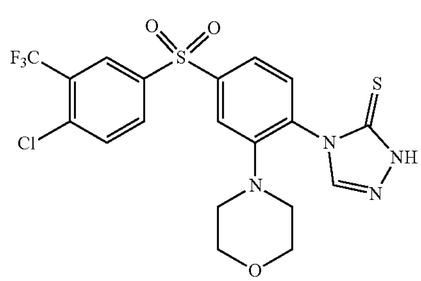 [SMILES: O=S(=O)(c1ccc(-n2cn[nH]c2=S)c(N2CCOCC2)c1)c1ccc(Cl)c(C(F)(F)F)c1] | 4-(4-((4-chloro-3-(trifluoromethyl)phenyl)sulfonyl)-2-morpholinophenyl)-2,4-dihydro-3H-1,2,4-triazole-3-thione; |

| Compound No. | Structure | Name |
|---|---|---|
| 3 | 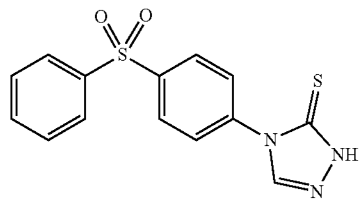 [SMILES: O=S(=O)(c1ccccc1)c1ccc(-n2cn[nH]c2=S)cc1] | 4-(4-(phenylsulfonyl)phenyl)-2,4-dihydro-3H-1,2,4-triazole-3-thione; |
| 4 | 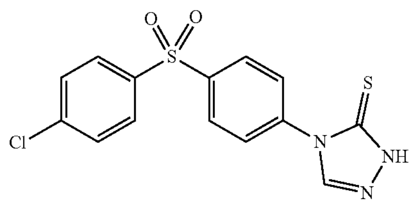 [SMILES: O=S(=O)(c1ccc(Cl)cc1)c1ccc(-n2cn[nH]c2=S)cc1] | 4-(4-((4-chlorophenyl)sulfonyl)phenyl)-2,4-dihydro-3H-1,2,4-triazole-3-thione; |
| 5 | 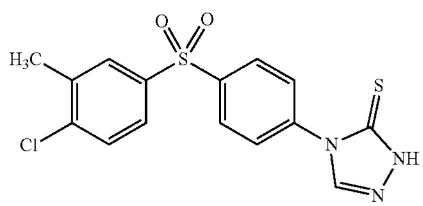 [SMILES: Cc1cc(S(=O)(=O)c2ccc(-n3cn[nH]c3=S)cc2)ccc1Cl] | 4-(4-((4-chloro-3-methylphenyl)sulfonyl)phenyl)-2,4-dihydro-3H-1,2,4-triazole-3-thione; |
| 6 | 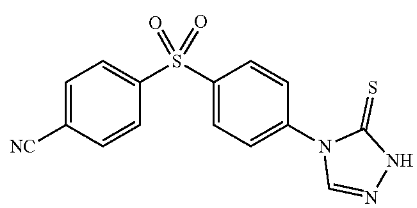 [SMILES: N#Cc1ccc(S(=O)(=O)c2ccc(-n3cn[nH]c3=S)cc2)cc1] | 4-((4-(5-thioxo-1,5-dihydro-4H-1,2,4-triazol-4-yl)phenyl)sulfonyl)benzonitrile; |
| 7 | 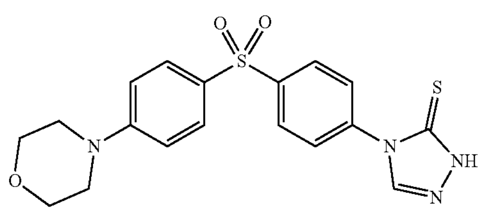 [SMILES: O=S(=O)(c1ccc(N2CCOCC2)cc1)c1ccc(-n2cn[nH]c2=S)cc1] | 4-(4-((4-morpholinophenyl)sulfonyl)phenyl)-2,4-dihydro-3H-1,2,4-triazole-3-thione; |
| 8 | 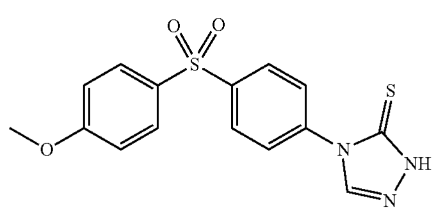 [SMILES: COc1ccc(S(=O)(=O)c2ccc(-n3cn[nH]c3=S)cc2)cc1] | 4-(4-((4-methoxyphenyl)sulfonyl)phenyl)-2,4-dihydro-3H-1,2,4-triazole-3-thione; |
| 9 | 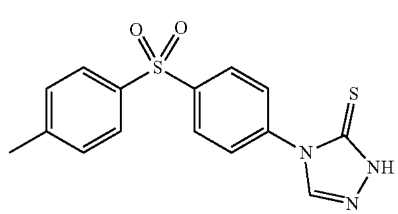 [SMILES: Cc1ccc(S(=O)(=O)c2ccc(-n3cn[nH]c3=S)cc2)cc1] | 4-(4-tosylphenyl)-2,4-dihydro-3H-1,2,4-triazole-3-thione; |

| Compound No. | Structure | Name |
|---|---|---|
| 10 | 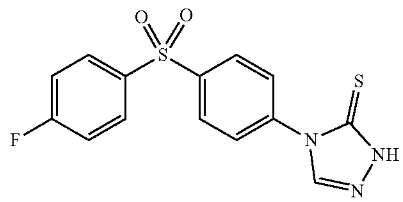 [SMILES: O=S(=O)(c1ccc(F)cc1)c1ccc(-n2cn[nH]c2=S)cc1] | 4-(4-((4-fluorophenyl)sulfonyl)phenyl)-2,4-dihydro-3H-1,2,4-triazole-3-thione; |
| 11 | 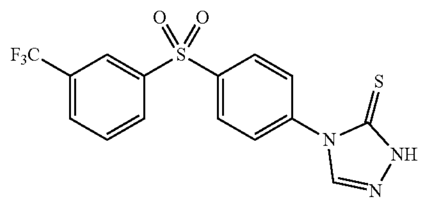 | 4-(4-((3-(trifluoromethyl)phenyl)sulfonyl)phenyl)-2,4-dihydro-3H-1,2,4-triazole-3-thione; |
| 12 | 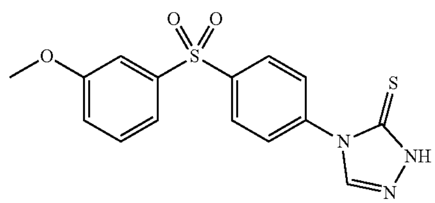 [SMILES: COc1cccc(S(=O)(=O)c2ccc(-n3cn[nH]c3=S)cc2)c1] | 4-(4-((3-methoxyphenyl)sulfonyl)phenyl)-2,4-dihydro-3H-1,2,4-triazole-3-thione; |
| 13 | 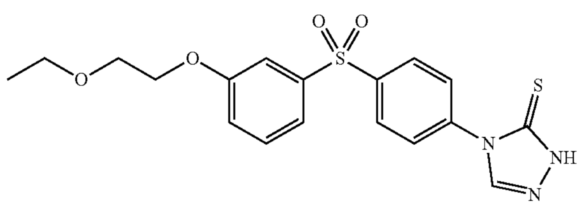 [SMILES: CCOCCOc1cccc(S(=O)(=O)c2ccc(-n3cn[nH]c3=S)cc2)c1] | 4-(4-((3-(2-ethoxyethoxy)phenyl)sulfonyl)phenyl)-2,4-dihydro-3H-1,2,4-triazole-3-thione; |
| 14 | 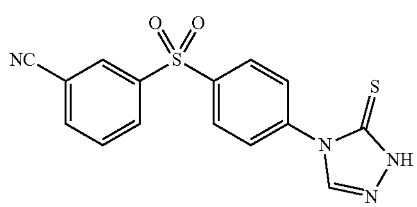 [SMILES: N#Cc1cccc(S(=O)(=O)c2ccc(-n3cn[nH]c3=S)cc2)c1] | 3-((4-(5-thioxo-1,5-dihydro-4H-1,2,4-triazol-4-yl)phenyl)sulfonyl)benzonitrile; |
| 15 | 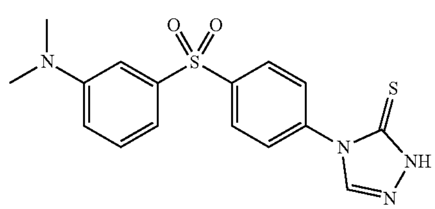 [SMILES: CN(C)c1cccc(S(=O)(=O)c2ccc(-n3cn[nH]c3=S)cc2)c1] | 4-(4-((3-(dimethylamino)phenyl)sulfonyl)phenyl)-2,4-dihydro-3H-1,2,4-triazole-3-thione; |
| 16 | 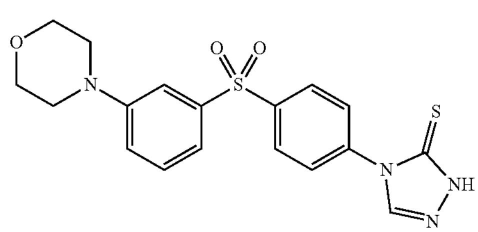 [SMILES: O=S(=O)(c1ccc(-n2cn[nH]c2=S)cc1)c1cccc(N2CCOCC2)c1] | 4-(4-((3-morpholinophenyl)sulfonyl)phenyl)-2,4-dihydro-3H-1,2,4-triazole-3-thione; |

-continued

| Compound No. | Structure | Name |
|---|---|---|
| 17 | 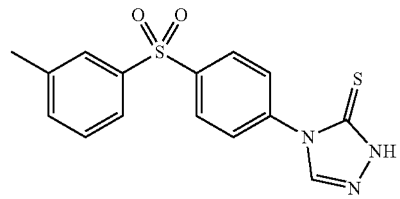 [SMILES: Cc1cccc(S(=O)(=O)c2ccc(-n3cn[nH]c3=S)cc2)c1] | 4-(4-(m-tolylsulfonyl)phenyl)-2,4-dihydro-3H-1,2,4-triazole-3-thione; |
| 18 | 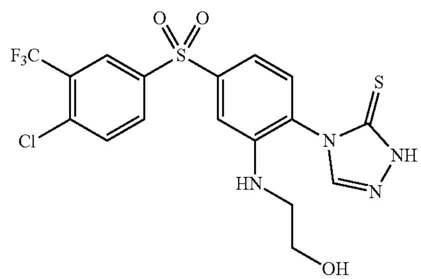 [SMILES: O=S(=O)(c1ccc(-n2cn[nH]c2=S)c(NCCO)c1)c1ccc(Cl)c(C(F)(F)F)c1] | 4-(4-((4-chloro-3-(trifluoromethyl)phenyl)sulfonyl)-2-((2-hydroxyethyl)amino)phenyl)-2,4-dihydro-3H-1,2,4-triazole-3-thione; |
| 19 | 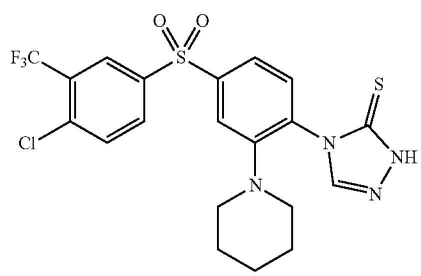 | 4-(4-((4-chloro-3-(trifluoromethyl)phenyl)sulfonyl)-2-(piperidin-1-yl)phenyl)-2,4-dihydro-3H-1,2,4-triazole-3-thione; |
| 20 | 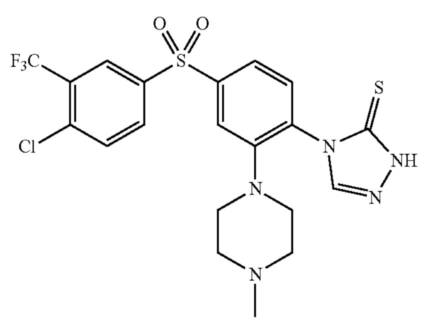 [SMILES: CN1CCN(c2cc(S(=O)(=O)c3ccc(Cl)c(C(F)(F)F)c3)ccc2-n2cn[nH]c2=S)CC1] | 4-(4-((4-chloro-3-(trifluoromethyl)phenyl)sulfonyl)-2-(4-methylpiperazin-1-yl)phenyl)-2,4-dihydro-3H-1,2,4-triazole-3-thione; |
| 21 | 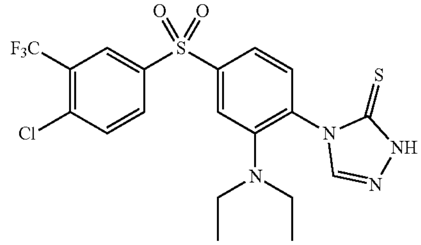 | 4-(4-((4-chloro-3-(trifluoromethyl)phenyl)sulfonyl)-2-(diethylamino)phenyl)-2,4-dihydro-3H-1,2,4-triazole-3-thione; |

-continued

| Compound No. | Structure | Name |
|---|---|---|
| 22 | 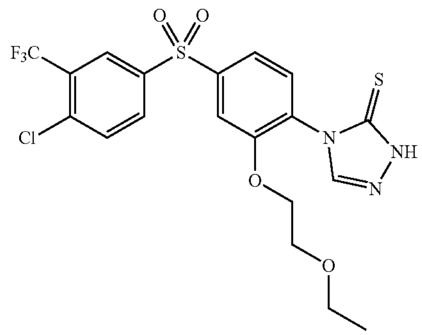 [SMILES: CCOCCOc1cc(S(=O)(=O)c2ccc(Cl)c(C(F)(F)F)c2)ccc1-n1cn[nH]c1=S] | 4-(4-((4-chloro-3-(trifluoromethyl)phenyl)sulfonyl)-2-(2-ethoxyethoxy)phenyl)-2,4-dihydro-3H-1,2,4-triazole-3-thione; |
| 23 | 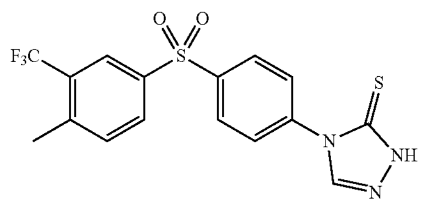 | 4-(4-((4-methyl-3-(trifluoromethyl)phenyl)sulfonyl)phenyl)-2,4-dihydro-3H-1,2,4-triazole-3-thione; |
| 24 | 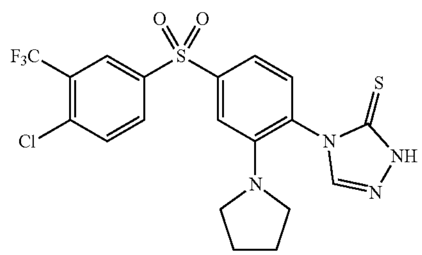 [SMILES: O=S(=O)(c1ccc(-n2cn[nH]c2=S)c(N2CCCC2)c1)c1ccc(Cl)c(C(F)(F)F)c1] | 4-(4-((4-chloro-3-(trifluoromethyl)phenyl)sulfonyl)-2-(pyrrolidin-1-yl)phenyl)-2,4-dihydro-3H-1,2,4-triazole-3-thione; and |
| 25 | | 4-(4-((3-(2-methoxyethoxy)phenyl)sulfonyl)phenyl)-2,4-dihydro-3H-1,2,4-triazole-3-thione, | or a pharmaceutically acceptable salt thereof.

23. The composition of claim 1, wherein the compound is:

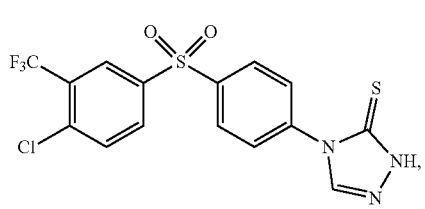 [SMILES: O=S(=O)(c1ccc(-n2cn[nH]c2=S)cc1)c1ccc(Cl)c(C(F)(F)F)c1]

or a pharmaceutically acceptable salt thereof.

24. The composition of claim 1, wherein the compound is:

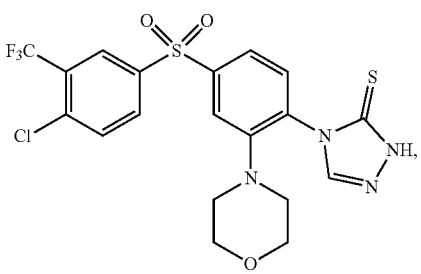 [SMILES: O=S(=O)(c1ccc(-n2cn[nH]c2=S)c(N2CCOCC2)c1)c1ccc(Cl)c(C(F)(F)F)c1]

or a pharmaceutically acceptable salt thereof.

* * * * *